(12) United States Patent
Fritsche et al.

(10) Patent No.: US 10,357,540 B2
(45) Date of Patent: Jul. 23, 2019

(54) IMMUNOTHERAPY AGAINST SEVERAL TUMORS INCLUDING GASTROINTESTINAL AND GASTRIC CANCER

(71) Applicant: IMMATICS BIOTECHNOLOGIES GMBH, Tuebingen (DE)

(72) Inventors: Jens Fritsche, Dusslingen (DE); Toni Weinschenk, Aichwald (DE); Steffen Walter, Houston, TX (US); Peter Lewandrowski, Tuebingen-Hirschau (DE); Harpreet Singh, Houston, TX (US)

(73) Assignee: Immatics Biotechnologies GmbH, Tuebingen (DE)

( * ) Notice: Subject to any disclaimer, the term of this patent is extended or adjusted under 35 U.S.C. 154(b) by 0 days.

(21) Appl. No.: 15/639,506

(22) Filed: Jun. 30, 2017

(65) Prior Publication Data

US 2018/0125929 A1 May 10, 2018

Related U.S. Application Data

(60) Continuation of application No. 14/615,539, filed on Feb. 6, 2015, now Pat. No. 9,717,774, which is a division of application No. 13/051,665, filed on Mar. 18, 2011, now Pat. No. 9,101,585.

(60) Provisional application No. 61/315,704, filed on Mar. 19, 2010.

(30) Foreign Application Priority Data

Mar. 19, 2010 (GB) .................................... 1004551.6

(51) Int. Cl.
| | |
|---|---|
| A61K 38/04 | (2006.01) |
| C07K 7/06 | (2006.01) |
| A61K 38/17 | (2006.01) |
| A61K 39/00 | (2006.01) |
| G01N 33/50 | (2006.01) |
| A61P 35/00 | (2006.01) |

(52) U.S. Cl.
CPC ...... *A61K 38/1709* (2013.01); *A61K 39/0011* (2013.01); *A61P 35/00* (2018.01); *C07K 7/06* (2013.01); *G01N 33/505* (2013.01); *A61K 2039/5158* (2013.01); *A61K 2039/572* (2013.01); *A61K 2039/585* (2013.01); *C07K 2319/00* (2013.01)

(58) Field of Classification Search
CPC ....... A61K 38/04; A61K 39/0011; C07K 7/06
USPC .................................................... 424/185.1
See application file for complete search history.

(56) References Cited

U.S. PATENT DOCUMENTS

| | | | |
|---|---|---|---|
| 7,994,276 B2 | 8/2011 | Singh et al. | |
| 8,119,139 B2 | 2/2012 | Weinschenk et al. | |
| 8,669,063 B2 * | 3/2014 | Weinschenk ......... | G01N 33/574 435/7.1 |
| 9,389,235 B2 * | 7/2016 | Weinschenk ......... | G01N 33/574 |
| 9,671,404 B2 * | 6/2017 | Singh ............... | G01N 33/57419 |
| 2004/0236091 A1 | 11/2004 | Chicz et al. | |
| 2007/0037204 A1 | 2/2007 | Aburatani et al. | |
| 2009/0004213 A1 | 1/2009 | Singh et al. | |
| 2009/0136528 A1 | 5/2009 | Singh et al. | |
| 2011/0318380 A1 * | 12/2011 | Brix .................... | A61K 39/0011 424/193.1 |
| 2013/0045191 A1 | 2/2013 | Weinschenk et al. | |

FOREIGN PATENT DOCUMENTS

| | | |
|---|---|---|
| EP | 1 568 373 A2 | 8/2005 |
| EP | 2172211 A1 | 4/2010 |
| WO | 03/100432 A2 | 12/2003 |
| WO | 02/36614 A2 | 5/2005 |
| WO | 2007/005635 A2 | 1/2007 |
| WO | 2009/015841 A1 | 2/2009 |
| WO | 2009/045115 A1 | 4/2009 |
| WO | 2010/037395 A2 | 4/2010 |

OTHER PUBLICATIONS

Shah, M., et al. "Inhibition of Siah2 ubiquitin ligase by vitamin K3 (menadione) attenuates hypoxia and MAPK signaling and blocks melanoma tumorigenesis." Pigment Cell Melanoma Res 22.6 (2009): 799-808.

Yasui, W., et al. "Increased expression of p34cdc2 and its kinase activity in human gastric and colonic carcinomas." Int J Cancer 53.1 (1993): 36-41.

Yee, C., et al. "Adoptive T cell therapy using antigen-specific CD8+ T cell clones for the treatment of patients with metastatic melanoma: in vivo persistence, migration, and antitumor effect of transferred T cells." Proc.Natl.Acad.Sci.U.S.A 99.25 (2002): 16168-73.

(Continued)

*Primary Examiner* — Yan Xiao
(74) *Attorney, Agent, or Firm* — McBee Moore Woodward & Vanik IP, LLC

(57) ABSTRACT

A method of treating a patient who has gastric cancer, gastrointestinal cancer, colorectal cancer, pancreatic cancer, lung cancer, and/or renal cancer includes administering to said patient a composition containing a population of activated T cells that selectively recognize cells in the patient that aberrantly express a peptide. A pharmaceutical composition contains activated T cells that selectively recognize cells in a patient that aberrantly express a peptide, and a pharmaceutically acceptable carrier, in which the T cells bind to the peptide in a complex with an MHC class I molecule, and the composition is for treating the patient who has gastric cancer, gastrointestinal cancer, colorectal cancer, pancreatic cancer, lung cancer, and/or renal cancer. A method of treating a patient who has cancer includes administering to said patient a composition comprising a peptide in the form of a pharmaceutically acceptable salt, thereby inducing a T-cell response to the cancer.

15 Claims, 4 Drawing Sheets

Specification includes a Sequence Listing.

(56) References Cited

OTHER PUBLICATIONS

Yin, S., et al. "CD133 positive hepatocellular carcinoma cells possess high capacity for tumorigenicity." Int.J Cancer 120.7 (2007): 1444-50.

Yokozaki, H., W. Yasui, and E. Tahara. "Genetic and epigenetic changes in stomach cancer." Int Rev.Cytol. 204 (2001): 49-95.

Yuan, W., et al. "Expression of EphA2 and E-cadherin in gastric cancer: correlated with tumor progression and lymphogenous metastasis." Pathol.Oncol Res 15.3 (2009): 473-78.

Yuan, W. J., et al. "Over-expression of EphA2 and EphrinA-1 in human gastric adenocarcinoma and its prognostic value for post-operative patients." Dig.Dis.Sci. 54.11 (2009): 2410-17.

Zaremba, S., et al. "Identification of an enhancer agonist cytotoxic T lymphocyte peptide from human carcinoembryonic antigen." Cancer Res. 57.20 (1997): 4570-77.

Zhang, X., R. M. Kedl, and J. Xiang. "CD40 ligation converts TGF-beta-secreting tolerogenic CD4-8-dendritic cells into IL-12-secreting immunogenic ones." Biochem.Biophys.Res Commun. 379.4 (2009): 954-58.

Zhang, X. L., et al. "Comparative study on overexpression of HER2/neu and HER3 in gastric cancer." World J Surg 33.10 (2009): 2112-18.

Zhao, C., et al. "Hedgehog signalling is essential for maintenance of cancer stem cells in myeloid leukaemia." Nature (2009).

Zheng, H., et al. "Cell surface targeting of heat shock protein gp96 induces dendritic cell maturation and antitumor immunity." J Immunol. 167.12 (2001): 6731-35.

Zheng, H., et al. "MUC6 down-regulation correlates with gastric carcinoma progression and a poor prognosis: an immunohistochemical study with tissue microarrays." J Cancer Res Clin Oncol 132.12 (2006): 817-23.

Zheng, H. C., et al. "Overexpression of GRP78 and GRP94 are markers for aggressive behavior and poor prognosis in gastric carcinomas." Hum.Pathol. 39.7 (2008): 1042-49.

Zhou, G., et al. "2D differential in-gel electrophoresis for the identification of esophageal scans cell cancer-specific protein markers." Mol.Cell Proteomics. 1.2 (2002): 117-24.

Zhou, L., et al. "TGF-beta-induced Foxp3 inhibits T(H)I7 cell differentiation by antagonizing RORgammat function." Nature 453. 7192 (2008): 236-40.

Zhu, K. J., et al. "Imiquimod inhibits the differentiation but enhances the maturation of human monocyte-derived dendritic cells." Int Immunopharmacol. 9.4 (2009): 412-17.

Dutoit et al.,Brain, 2012, 135: 1042-1054.

Roitt et al., 1998, Immunolog, 4th ed, Mosby, London, pp. 113-114.

Holmes (Expert Opinion on Investigation Drugs 2001: 10: 511-519).

Khong et al. (J. Immunol. Jan. 15, 2002; 168 (2):951-956).

Lu et al. (Cancer Research 62: 5807-5812, 2002).

Celis (J of Clinical Investigation, 2002, 110: 1765-1768).

Suri et al., "Identification of naturally processed peptides bound to the class I MHC molecule H-2-Kd of normal and TAP-deficient cells," 2005, Wiley-VCH Verlag GmbH & Co. KGaG, Weinheim, European Journal of Immunology.

Markiewicz et al., "IL-12-CTL Synapse Formation and Induces Self-Reactivity," The Journal of Immunology, 2009, vol. 82, No. 3, pp. 1351-1361.

Stevanovic S. et al., "Generating data for databases—the peptide repertoire of HLA molecules," Immunoinformatics: Bioinformatic Strategies for Better Understanding of Immune Function: Novartis Foundation Symposium, 2003, 254, vol. 254, pp. 143-164.

Bergwelt-Baildon Von M.S. et al., "T-Call Responses to Cyclin B1 Are Not Restricted to p53-Overexpressing Tumors" Clinical Cancer Research, 2009, vol. 15, No. 22, p. 7106.

Greiner J. et al., "Identification and characterization of epitopes of the receptor for hyaluronic acid-mediated motility (RHAMM/ CD168) recognized by CD8+ T cells of HLA-A2 positive patients with acute myeloid leukemia," Blood, 2005, vol. 106, pp. 938-945.

Winzierl A. O. et al., "Features of TAP-independent MHC class I ligands revealed by quantitative mass spectrometry," European Journal of Immunology, 2008, 38:1503-1510, Wiley-VCH Verlag GmbH & Co. KGaG, Gene symbol TPX2.

Eurasian Office Action dated Apr. 15, 2013, issued in Application No. 201201306126.

International Search Report for PCT/EP2011/053863 dated Jun. 16, 2011.

International Preliminary Report on Patentability and Written Opinion Based on International Application No. PCT/EP2011/053863 dated Oct. 4, 2012.

Weinschenk et al., "Integrated Functional Genomics Approach for the Design of Patient-Individual Antitumor Vaccines" Cancer Research; American Association for Cancer Research, US, vol. 62, No. 20, Oct. 15, 2002, pp. 5818-5827.

Immatics Company Fact Sheet; Feb. 1, 2009, Retrieved From the Internet: URL: www.immatics.com/index.php?action=download &id=421 [Retrieved on May 27, 2011].

Bioregio Stern: "Immatics Biotechnologies Stellt Naechste Generation Der Xpresident-Plattform Vor"; Jun. 17, 2009: Retrieved From the Internet: URL:http://www.bioregio-stern.de/de/aktuelles/details_ nachrichten.php?of_id=4169 [Retrieved on May 25, 2011].

Feb. 17, 2010; Retrieved From the Internet: URL: http://silico. wordpress.com/2010/02/17/immatics-signs-collaboration-agreement-with-cancer-research-uk/ [Retrieved on May 26, 2011].

Immatics Biotechnologies Significantly Improves Xpresident Technology Platform; Immatics Press Release [Online] Jun. 17, 2009; Retrieved From the Internet: URL http://www.immatics.com/index. php?pages=76*modaction=detail&modid=213&modid2=2009.

Bikeye et al.; "ASPM-Associated Stem Cell Proliferation Is Involved in Malignant Progression of Gliomas and Constitutes an Attractive Therapeutic Target"; Cancer Cell International, Biomed Central, London, GB, vol. 10; No. 1; Jan. 11, 2011; p. 1.

Chanock, S. J., et al. "HLA-A, -B, -Cw, -DQAI and -DRBI Alleles in a Caucasian Population from Bethesda, USA." Hum. Immunol. 65 (2004): 1211-23.

Ahmed, A. U., et al. "Effect of disrupting seven-in-absentia homolog 2 function on lung cancer cell growth." J Natl. Cancer Inst. 100.22 (2008): 1606-29.

Allison, J. P. and M. F. Krummel. "The Yin and Yang of T cell costimulation." Science 270.5238 (1995): 932-33.

Altmeyer, A., et al. "Tumor-specific cell surface expression of the-KDEL containing, endoplasmic reticular heat shock protein gp96." Int J Cancer 69.4 (1996): 340-49.

Appay, V., et al. "Decreased specific CDS+ T cell cross-reactivity of antigen recognition following vaccination with Melan-A peptide." Eur.J Immunol. 36.7 (2006): 1805-14.

Banerjee, S. K., et al. "Expression of cdc2 and cyclin BI in Helicobacter pylori-associated gastric MALT and MALT lymphoma : relationship to cell death, proliferation, and transformation." Am J Pathol. 156.1 (2000): 217-25.

Bartman, A. E., et al. "Aberrant expression of MUC5AC and MUC6 gastric mucin genes in colorectal polyps." Int J Cancer 80.2 (1999): 210-18.

Basu, S., et al. "Necrotic but not apoptotic cell death releases heat shock proteins, which deliver a partial maturation signal to dendritic cells and activate the NF-kappa B pathway." Int Immunol. 12.11 (2000): 1539-46.

Bauer, B., S. Bartfeld, and T. F. Meyer. "H. pylori selectively blocks EGFR endocytosis via the non-receptor kinase c-Abl and CagA." Cell Microbial. 11.1 (2009): 156-69.

Benatti, P., et al. "A balance between NF-Y and p53 governs the pro- and anti-apoptotic transcriptional response." Nucleic Acids Res 36.5 (2008): 1415-28.

Bertolini, G., et al. "Highly tumorigenic lung cancer CD133+ cells display stem-like features and are spared by cisplatin treatment." Proc Natl.Acad.Sci.U.S.A 106.38 (2009): 16281-86.

Bierie, B. and H. L. Moses. "TGF-beta and cancer." Cytokine Growth Factor Rev. 17.1-2 (2006): 29-40.

Bitoun, E. and K. E. Davies. "The robotic mouse: unravelling the function of AF4 in the cerebellum." Cerebellum. 4.4 (2005): 250-60.

(56) References Cited

OTHER PUBLICATIONS

Bolhassani, A. and S. Rafati. "Heat-shock proteins as powerful weapons in vaccine development." Expert.Rev. Vaccines. 7.8 (2008): 1185-99.

Borset, M., et al. "The role of hepatocyte growth factor and its receptor c-Met in multiple myeloma and other blood malignancies." Leak.Lymphoma 32.3-4 (1999): 249-56.

Bradbury, P. A., et al. "Matrix metalloproteinase 1, 3 and 12 polymorphisms and esophageal adenocarcinoma risk and prognosis." Carcinogenesis 30.5 (2009): 793-98.

Brown, C. E., et al. "Recognition and killing of brain tumor stem-like initiating cells by CD8+ cytolytic T cells." Cancer Research 69.23 (2009): 8886-93.

Bruckdorfer, T., 0. Marder, and F. Albericio. "From production of peptides in milligram amounts for research to multi-tons quantities for drugs of the future." Curr.Pharm.Biotechnol. 5.1 (2004): 29-43.

Brunsvig, P. F., et al. "Telomerase peptide vaccination: a phase 1/11 study in patients with non-small cell lung cancer." Cancer Immunol. Immunother. 55.12 (2006): 1553-64.

Cabanes, D., et al. "Gp96 is a receptor for a novel Listeria monocytogenes virulence factor, Vip, a surface protein." EMBO J 24.15 (2005): 2827-38.

Calzado, M. A., et al. "An inducible autoregulatory loop between HIPK2 and Siah2 at the apex of the hypoxic response." Nat.Cell Biol. 11.1 (2009): 85-91.

Castelli, C., et al. "Heat shock proteins: biological functions and clinical application as personalized vaccines for human cancer." Cancer Immunol.Immunother. 53.3 (2004): 227-33.

Castriconi, R., et al. "Both CD133+ and C." Eur.J Immunol. 37.11 (2007): 3190-96.

Chen, C. H., et al. "Inhibition of heregulin signaling by an aptamer that preferentially binds to the oligomeric form of human epidermal growth factor receptor-3." Proc Natl.Acad.Sci.U.S.A 100.16 (2003): 9226-31.

Chen, Z. and J. J. O'Shea. "Regulation of IL-17 production in human lymphocytes." Cytokine 41.2 (2008): 71-78.

Cho, S. 0., et al. "Helicobacter pylori in a Korean Isolate Expressed Proteins Differentially in Human Gastric Epithelial Cells." Dig.Dis. Sci. (2009).

Christianson, J. C., et al. "OS-9 and GRP94 deliver mutant alphal-antitrypsin to the Hrdl-SEL1L ubiquitin ligase complex for ERAD." Nat.Cell Biol. 10.3 (2008): 272-82.

Cisek, L. J. and J. L. Corden. "Phosphorylation of RNA polymerase by the murine homologue of the cell-cycle control protein cdc2." Nature 339.6227 (1989): 679-84.

Colombetti, S., et al. "Prolonged TCR/CD28 engagement drives IL-2-independent T cell clonal expansion through signaling mediated by the mammalian target of rapamycin." J Immunol. 176.5 (2006): 2730-38.

Confalonieri, S., et al. "Alterations of ubiquitin ligases in human cancer and their association with the natural history of the tumor." Oncogene 28.33 (2009): 2959-68.

Corso, S., et al. "Silencing the MET oncogene leads to regression of experimental tumors and metastases." Oncogene 27.5 (2008): 684-93.

Cox, C. V., et al. "Expression of CD133 on leukemia-initiating cells in childhood ALL." Blood 113.14 (2009): 3287-96.

Cunha-Ferreira, I., et al. "The SCF/Slimb ubiquitin ligase limits centrosome amplification through degradation of SAK/PLK4." Curr. Biol. 19.1 (2009): 43-49.

DeLuca, J. G., et al. "Heel and nuf2 are core components of the kinetochore outer plate essential for organizing microtubule attachment sites." Mol.Biol.Cell 16.2 (2005): 519-31.

Deng, H., et al. "Matrix metalloproteinase 11 depletion inhibits cell proliferation in gastric cancer cells." Biochem. Biophys.Res Commun. 326.2 (2005): 274-81.

Dengjel, J., et al. "Unexpected Abundance of HLA Class II Presented Peptides in Primary Renal Cell Carcinomas." Clin Cancer Res. 12.14 (2006): 4163-70.

Deremer, D. L., C. Ustun, and K. Natarajan. "Nilotinib: a second-generation tyrosine kinase inhibitor for the treatment of chronic myelogenous leukemia." Clin Ther. 30.11 (2008): 1956-75.

Di Renzo, M. F., et al. "Overexpression and amplification of the met/HGF receptor gene during the progression of colorectal cancer." Clio.Cancer Res. 1.2 (1995): 147-54.

Dong, G., et al. "Hepatocyte growth factor/scatter factor-induced activation of MEK and PI3K signal pathways contributes to expression of proangiogenic cytokines interleukin-8 and vascular endothelial growth factor in head and neck squamous cell carcinoma." Cancer Res. 61.15 (2001): 5911-18.

Dudley, M. E., et al. "Cancer regression and autoimmunity in patients after clonal repopulation with antitumor lymphocytes." Science 298.5594 (2002): 850-54.

Dudley, M. E., et al. "Adoptive cell transfer therapy following non-myeloablative but lymphodepleting chemotherapy for the treatment of patients with refractory metastatic melanoma." J.Clin. Oncol. 23.10 (2005): 2346-57.

Duong, C., et al. "Pretreatment gene expression profiles can be used to predict response to neoadjuvant chemoradiotherapy in esophageal cancer." Ann Surg Oncol 14.12 (2007): 3602-09.

Egland, K. A., et al. "High expression of a cytokeratin-associated protein in many cancers." Proc Natl.Acad.Sci.U.S.A 103.15 (2006): 5929-34.

Eramo, A., et al. "Identification and expansion of the tumorigenic lung cancer stem cell population." Cell Death Differ 15.3 (2008): 504-14.

Esashi, F., et al. "CDK-dependent phosphorylation of BRCA2 as a regulatory mechanism for recombinational repair." Nature 434.7033 (2005): 598-604.

Escobar, M. A., et al. "Profiling of nuclear extract proteins from human neuroblastoma cell lines: the search for fingerprints." J Pediatr.Surg 40.2 (2005): 349-58.

Ferracini, R., et al. "The Met/HGF receptor is over-expressed in human osteosarcomas and is activated by either a paracrine or an autocrine circuit." Oncogene 10.4 (1995): 739-49.

Fischer, J., et al. "Duplication and overexpression of the mutant allele of the MET proto- oncogene in multiple hereditary papillary renal cell tumours." Oncogene 17.6 (1998): 733-39.

Flanagan, J. M., et al. "Genomics screen in transformed stem cells reveals RNASEH2A, PPAP2C, and ADARB1 as putative anticancer drug targets." Mol.Cancer Ther. 8.1 (2009): 249-60.

Fong, L., et al. "Altered peptide ligand vaccination with Flt3 ligand expanded dendritic cells for tumor immunotherapy." Proc.Natl.Acad. Sci.U.S.A 98.15 (2001): 8809-14.

Frasor, J., et al. "Estrogen down-regulation of the corepressor N-CoR: mechanism and implications for estrogen derepression of N-CoR-regulated genes." Proc Natl.Acad.Sci.U.S.A 102.37 (2005): 13153-57.

Frew, I. J., et al. "Generation and analysis of Siah2 mutant mice." Mol.Cell Biol. 23.24 (2003): 9150-61.

Fu, Y. and A. S. Lee. "Glucose regulated proteins in cancer progression, drug resistance and immunotherapy." Cancer Biol. Ther. 5.7 (2006): 741-44.

Forge, K. A., et al. "Suppression of Ras-mediated tumorigenicity and metastasis through inhibition of the Met receptor tyrosine kinase." Proc.Natl.Acad.Sci.U.S.A 98.19 (2001): 10722-27.

Forge, K. A., Y. W. Zhang, and G. F. Vande Woode. "Met receptor tyrosine kinase: enhanced signaling through adapter proteins." Oncogene 19.49 (2000): 5582-89.

Gattinoni, L., et al. "Adoptive immunotherapy for cancer: building on success." Nat.Rev.Immunol. 6.5 (2006): 383-93.

Gherardi, E. and M. Stoker. "Hepatocyte growth factor—scatter factor: mitogen, motogen, and met." Cancer Cells 3.6 (1991): 227-32.

Glen, A., et al. "iTRAQ-facilitated proteomic analysis of human prostate cancer cells identifies proteins associated with progression." J Proteome.Res 7.3 (2008): 897-907.

Gnjatic, S., et al. "NY-C0-58/KIF2C is overexpressed in a variety of solid tumors and induces frequent T cell responses in patients with colorectal cancer." Int J Cancer (2009).

(56) References Cited

OTHER PUBLICATIONS

Guo, W. C., et al. "Expression and its clinical significance of heat shock protein gp96 in human osteosarcoma." Neoplasma 57.1 (2010): 62-67.
Habelhah, H., et al. "Stress-induced decrease in TRAF2 stability is mediated by Siah2." EMBO J 21.21 (2002): 5756-65.
Hamamoto, A., et al. "Aberrant expression of the gastric mucin MUC6 in human pulmonary adenocarcinoma xenografts." Int J Oncol 26.4 (2005): 891-96.
Harada, T., et al. "Genome-wide analysis of pancreatic cancer using microarray-based techniques." Pancreatology. 9.1-2 (2009): 13-24.
Harper, L. J., et al. "Stem cell patterns in cell lines derived from head and neck squamous cell carcinoma." J Oral Pathol.Med 36.10 (2007): 594-603.
Hayama, S., et al. "Activation of CDCA1-KNTC2, members of centromere protein complex, involved in pulmonary carcinogenesis." Cancer Research 66.21 (2006): 10339-48.
Heike, M., et al. "Expression of stress protein gp96, a tumor rejection antigen, in human colorectal cancer." Int J Cancer 86.4 (2000): 489-93.
Hodorova, I., et al. "Gp96 and its different expression in breast carcinomas." Neoplasma 55.1 (2008): 31-35.
Horton, R. A., et al. "A substrate for deubiquitinating enzymes based on time-resolved fluorescence resonance energy transfer between terbium and yellow fluorescent protein." Anal.Biochem. 360.1 (2007): 138-43.
House, C. M., A. Moller, and D. D. Bowtell. "Siah proteins: novel drug targets in the Ras and hypoxia pathways." Cancer Research 69.23 (2009): 8835-38.
Howard, E. W., et al. "Decreased adhesiveness, resistance to anoikis and suppression of GRP94 are integral to the survival of circulating tumor cells in prostate cancer." Clin Exp.Metastasis 25.5 (2008): 497-508.
Hu, G. and E. R. Fearon. "Siah-1 N-terminal RING domain is required for proteolysis function, and C-terminal sequences regulate oligomerization and binding to target proteins." Mol.Cell Biol. 19.1 (1999): 724-32.
Huang, Y., et al. "Characterization of GPR56 protein and its suppressed expression in human pancreatic cancer cells." Mol.Cell Biochem. 308.1-2 (2008): 133-39.
Jansen, M. P., et al. "Downregulation of S1AH2, an ubiquitin E3 ligase, is associated with resistance to endocrine therapy in breast cancer." Breast Cancer Res Treat. 116.2 (2009): 263-71.
Jia, H. L., et al. "Gene expression profiling reveals potential biomarkers of human hepatocellular carcinoma." Clinical Cancer Research 13.4 (2007): 1133-39.
Jucker, M., et al. "The Met/hepatocyte growth factor receptor (HGFR) gene is overexpressed in some cases of human leukemia and lymphoma." Leak.Res. 18.1 (1994): 7-16.
Jung, G., J. A. Ledbetter, and H. J. Muller-Eberhard. "Induction of cytotoxicity in resting human T lymphocytes bound to tumor cells by antibody heteroconjugates." Proc Natl Acad Sci US A 84.13 (1987): 4611-15.
Jung, H. M., S. J. Choi, and J. K. Kim. "Expression profiles of SV40-immortalization—associated genes upregulated in various human cancers." J Cell Biochem. 106.4 (2009): 703-13.
Kaneko, N., et al. "siRNA-mediated knockdown against CDCAI and KNTC2, both frequently overexpressed in colorectal and gastric cancers, suppresses cell proliferation and induces apoptosis." Biochem. Biophys.Res Commun. 390.4 (2009): 1235-40.
Kang, H. M., et al. "Effects of Helicobacter pylori Infection on gastric mucin expression." : J Clin Gastroenterol. 42.1 (2008): 29-35.
Ko, M. A., et al. "Plk4 haploinsufficiency causes mitotic infidelity and carcinogenesis." Nat.Genet. 37.8 (2005): 883-88.
Kobayashi, M., et al. "Activation of ErbB3-PI3-kinase pathway is correlated with malignant phenotypes of adenocarcinomas." Oncogene 22.9 (2003): 1294-301.
Koochekpour, S., et al. "Met and hepatocyte growth factor/scatter factor expression in human gliomas." Cancer Res. 57.23 (1997): 5391-98.
Korzeniewski, N., et al. "Cullin 1 functions as a centrosomal suppressor of centriole multiplication by regulating polo-like kinase 4 protein levels." Cancer Research 69.16 (2009): 6668-75.
Hayashi, M., et al. "High expression of HER3 is associated with a decreased survival in gastric cancer." Clinical Cancer Research 14.23 (2008): 7843-49.
Krieg, A. M. "Therapeutic potential of Toll-like receptor 9 activation." Nat.Rev.Drug Discov. 5.6 (2006): 471-84.
Kunimoto, K., et al. "Involvement of IQGAP3, a regulator of Ras/ERK-related cascade, in hepatocyte proliferation in mouse liver regeneration and development." J Cell Physiol 220.3 (2009): 621-31.
Kuriyama, R., et al. "Gamma-tubulin-containing abnormal centrioles are induced by insufficient Plk4 in human HCT116 colorectal cancer cells." J Cell Sci. 122.Pt 12 (2009): 2014-23.
Lee, H. S., et al. "MUCI, MUC2, MUC5AC, and MUC6 expressions in gastric carcinomas: their roles as prognostic indicators." Cancer 92.6 (2001): 1427-34.
Leivo, I., et al. "Characterization of gene expression in major types of salivary gland carcinomas with epithelial differentiation." Cancer Genet.Cytogenet. 156.2 (2005): 104-13.
Lemmel, C., et al. "Differential quantitative analysis of MHC ligands by mass spectrometry using stable isotope labeling." Nat. Biotechnol. 22.4 (2004): 450-54.
Li, G., et al. "Downregulation of E-cadherin and Desmoglein 1 by autocrine hepatocyte growth factor during melanoma development." Oncogene 20.56 (2001): 8125-35.
Lim, S. 0., et al. "Expression of heat shock proteins (HSP27, HSP60, HSP70, HSP90, GRP78, GRP94) in hepatitis B virus-related hepatocellular carcinomas and dysplastic nodules." World J Gastroenterol. 11.14 (2005): 2072-79.
Lin, W., et al. "Tyrosine kinases and gastric cancer." Oncogene 19.49 (2000): 5680-89.
Liu, B. and Z. Li. "Endoplasmic reticulum HSP90b1 (gp96, grp94) optimizes B-cell function via chaperoning integrin and TLR but not immunoglobulin." Blood 112.4 (2008): 1223-30.
Liu, S. Y., et al. "Requirement of MMP-3 in anchorage-independent growth of oral squamous cell carcinomas." J Oral Pathol.Med 36.7 (2007): 430-35.
Lochter, A., et al. "The significance of matrix metalloproteinases during early stages of tumor progression." Ann N.Y. Acad.Sci. 857 (1998): 180-93.
Lund, C. V., et al. "Zinc finger transcription factors designed for bispecific coregulation of ErbB2 and ErbB3 receptors: insights into ErbB receptor biology." Mol.Cell Biol. 25.20 (2005): 9082-91.
Ma, S., et al. "Identification and characterization of tumorigenic liver cancer stem/progenitor cells." Gastroenterology 132.1 (2007): 2542-56.
MacLeod, R. J., M. Hayes, and I. Pacheco. "Wnt5a secretion stimulated by the extracellular calcium-sensing receptor inhibits defective Wnt signaling in colon cancer cells." Am J Physiol Gastrointest.Liver Physiol 293.1 (2007): G403-G411.
Macmillan, J.C., et al."Comparative expression of the mitotic regulators SAK and PLK in colorectal cancer." Ann Surg Oncol 8.9 (2001): 729-40.
Maney, T., et al. "The kinetochore of higher eucaryotes: a molecular view." Int Rev.Cytol. 194 (2000): 67-131.
Martin, C. M., et al. "Gene expression profiling in cervical cancer: identification of novel markers for disease diagnosis and therapy." Methods Mol.Biol. 511 (2009): 333-59.
Matsukita, S., et al. "Expression of mucins (MUCI, MUC2, MUC5AC and MUC6) in mucinous carcinoma of the breast: comparison with invasive ductal carcinoma." Histopathology 42.1 (2003): 26-36.
Maulik, G., et al. "Role of the hepatocyte growth factor receptor, c-Met, in oncogenesis and potential for therapeutic inhibition." Cytokine Growth Factor Rev. 13.1 (2002): 41-59.
Mizrak, D., M. Brittan, and M. Alison. "CD133: molecule of the moment." J Pathol. 214.1 (2008): 3-9.

(56) References Cited

OTHER PUBLICATIONS

Montesano, R., et al. "Differential effects of hepatocyte growth factor isoforms on epithelial and endothelial tubulogenesis." Cell Growth Differ. 9.5 (1998): 355-65.

Monzani, E., et al. "Melanoma contains CD133 and ABCG2 positive cells with enhanced tumourigenic potential." Eur.J Cancer 43.5 (2007): 935-46.

Moore, A. and L. Wordeman. "The mechanism, function and regulation of depolymerizing kinesins during mitosis." Trends Cell Biol. 14.10 (2004): 537-46.

Morgan, R. A., et al. "Cancer Regression in Patients After Transfer of Genetically Engineered Lymphocytes." Science (2006).

Mori, M., et al. "HLA gene and haplotype frequencies in the North American population: the National Marrow Donor Program Donor Registry." Transplantation 64.7 (1997): 1017-27.

Murray, G. I., et al. "Matrix metalloproteinases and their inhibitors in gastric cancer." Gut 43.6 (1998): 791-97.

Murshid, A., J. Gong, and S. K. Calderwood. "Heat-shock proteins in cancer vaccines: agents of antigen cross-presentation." Expert. Rev.Vaccines. 7.7 (2008): 1019-30.

Nakaigawa, N., et al. "Inactivation of von Hippel-Lindau gene induces constitutive phosphorylation of MET protein in clear cell renal carcinoma." Cancer Res. 66.7 (2006): 3699-705.

Nakamura, Y., et al. "Clinicopathological and biological significance of mitotic centromere—associated kinesin overexpression in human gastric cancer." Br.J Cancer 97.4 (2007): 543-49.

Nakayama, K., J. Qi, and Z. Ronai. "The ubiquitin ligase Siah2 and the hypoxia response." Mol.Cancer Res 7.4 (2009): 443-51.

Naldini, L., et al. "Hepatocyte growth factor (HGF) stimulates the tyrosine kinase activity of the receptor encoded by the proto-oncogene c-MET." Oncogene 6.4 (1991): 501-04.

Nguyen, Q. N., et al. "Light controllable siRNAs regulate gene suppression and phenotypes in cells." Biochim. Biophys.Acta 1758.3 (2006): 394-403.

Nishio, K., et al. "Crystal structure of the de-ubiquitinating enzyme UCH37 (human UCH-L5) catalytic domain." Biochem.Biophys. Res Commun. 390.3 (2009): 855-60.

Nojima, H., et al. "IQGAP3 regulates cell proliferation through the Ras/ERK signalling cascade." Nat.Cell Biol. 10.8 (2008):971-78.

Nomura H., et al. "Enhanced production of matrix metalloproteinases and activation of matrix metalloproteinase 2 (gelatinase A) in human gastric carcinomas." Int J Cancer 69.1 (1996): 9-16.

Nomura, H., et al. "Network-based analysis of calcium-binding protein genes identifies Grp94 as a target in human oral carcinogenesis." Br.J Cancer 97.6 (2007): 792-801.

Ohnuma, S., et al. "Cancer-associated splicing variants of the CDCAI and MSMB genes expressed in cancer cell lines and surgically resected gastric cancer tissues." Surgery 145.1 (2009): 57-68.

Park, Y. H., et al. "Capecitabine in combination with Oxaliplatin (XELOX) as a first-line therapy for advanced gastric cancer." Cancer Chemother.Pharmacol. (2007).

Pascolo, S., et al. "The non-classical HLA class I molecule HFE does not influence the NK-like activity contained in fresh human PBMCs and does not interact with NK cells." Int.Immunol. 17.2 (2005): 117-22.

Peel, N., et al. "Overexpressing centriole-replication proteins in vivo induces centriole overduplication and de novo formation." Curr.Biol. 17.10 (2007): 834-43.

Pereira, M. B., et al. "Immunohistochemical study of the expression of MUC5AC and MUC6 in breast carcinomas and adjacent breast tissues." J Clin Pathol. 54.3 (2001): 210-13.

Pietra, G., et al. "Natural killer cells kill human melanoma cells with characteristics of cancer stem cells." Int Immunol. 21.7 (2009): 793-801.

Poller, D. N., et al. "Production and characterization of a polyclonal antibody to the c-erbB-3 protein: examination of c-erbB-3 protein expression in adenocarcinomas." J Pathol. 168.3 (1992): 275-80.

Pons, E., C. C. Uphoff, and H. G. Drexler. "Expression of hepatocyte growth factor and its receptor c-met in human leukemia-lymphoma cell lines." Leak.Res. 22.9 (1998): 797-804.

Ponzetto, C., et al. "A novel recognition motif for phosphatidylinositol 3-kinase binding mediates its association with the hepatocyte growth factor/scatter factor receptor." Mol.Cell Biol. 13.8 (1993): 4600-08.

Poppe, M., et al. "Phosphorylation of Helicobacter pylori CagA by c-Abl leads to cell motility." Oncogene 26.24 (2007): 3462-72.

Pytel, D., et al. "Tyrosine kinase blockers: new hope for successful cancer therapy." Anticancer Agents Med Chem. 9.1 (2009): 66-76.

Qi, J., et al. "The ubiquitin ligase Siah2 regulates tumorigenesis and metastasis by HIF-dependent and-independent pathways." Proc Natl.Acad.Sci.U.S.A 105.43 (2008): 16713-18.

Qian, C. N., et al. "Met protein expression level correlates with survival in patients with late-stage nasopharyngeal carcinoma." Cancer Res. 62.2 (2002): 589-96.

Qian, Z., et al. "Cytogenetic and genetic pathways in therapy-related acute myeloid leukemia." Chem.Biol.Interact. (2009).

Ramirez, R., et al. "Over-expression of hepatocyte growth factor/scatter factor (HGF/SF) and the HGF/SF receptor (cMET) are associated with a high risk of metastasis and recurrence for children and young adults with papillary thyroid carcinoma." Clin Endocrinol. (OxO 53.5 (2000): 635-44.

Rammensee, H. G., et al. "SYFPEITHI: database for MHC ligands and peptide motifs." Immunogenetics 50.3-4 (1999): 213-19.

Rammensee, H. G., J. Bachmann, and S. Stevanovic. MHC Ligands and Peptide Motifs. Springer-Verlag, Heidelberg, Germany, 1997.

Rappa, G., 0. Fodstad, and A. Lorico. "The stem cell-associated antigen CD133 (Prominin-1) is a molecular therapeutic target for metastatic melanoma." Stem Cells 26.12 (2008): 3008-17.

Richardson, G. D., et al. "CD133, a novel marker for human prostatic epithelial stem cells." J Cell Sci.117.Pt 16 (2004):3539-45.

Rini, B. I., et al. "Combination immunotherapy with prostatic acid phosphatase pulsed antigen-presenting cells (provenge) plus bevacizumab in patients with serologic progression of prostate cancer after definitive local therapy." Cancer 107.1 (2006): 67-74.

Rodrigues-Martins, A., et al. "Revisiting the role of the mother centriole in centriole biogenesis." Science 316.5827 (2007):1046-50.

Rosenberg, S. A., et al. "A progress report on the treatment of 157 patients with advanced cancer using lymphokine-activated killer cells and interleukin-2 or high-dose interleukin-2 alone." N.Engl. J.Med. 316.15 (1987): 889-97.

Rosenberg, S. A., et al. "Use of tumor-infiltrating lymphocytes and interleukin-2 in the immunotherapy of patients with metastatic melanoma. A preliminary report." N.Engl.J Med 319.25 (1988): 1676-80.

Rott, R., et al. "Monoubiquitylation of alpha-synuclein by seven in absentia homolog (SIAH) promotes its aggregation in dopaminergic cells." J Biol.Chem. 283.6 (2008): 3316-28.

Rotella, S., et al. "Cells with characteristics of cancer stem/progenitor cells express the CD133 antigen in human endometrial tumors." Clinical Cancer Research 15.13 (2009): 4299-311.

Saiki, R. K., et al. "Primer-directed enzymatic amplification of DNA with a thermostable DNA polymerase." Science 239.4839 (1988): 487-91.

Samant, G. V. and P. W. Sylvester. "gamma-Tocotrienol inhibits ErbB3-dependent PI3K/Akt mitogenic signalling in neoplastic mammary epithelial cells." Cell Prolif. 39.6 (2006): 563-74.

Sanidas, E. E., et al. "Expression of the c-erbB-3 gene product in gastric cancer." Int J Cancer 54.6 (1993): 935-40.

Scott, G. K., et al. "Coordinate suppression of ERBB2 and ERBB3 by enforced expression of micro-RNA miR-125a or miR-125b." J Biol.Chem. 282.2 (2007): 1479-86.

Sergina, N. V., et al. "Escape from HER-family tyrosine kinase inhibitor therapy by the kinase-inactive HER3." Nature 445.7126 (2007): 437-41.

Shapiro, G. I. "Cyclin-dependent kinase pathways as targets for cancer treatment." J Clin Oncol 24.11 (2006): 1770-83.

Sherman-Baust, C. A., et al. "Remodeling of the extracellular matrix through overexpression of collagen VI contributes to cisplatin resistance in ovarian cancer cells." Cancer Cell 3.4 (2003): 377-86.

(56) References Cited

OTHER PUBLICATIONS

Sheu, M. L., S. H. Liu, and K. H. Lan. "Honokiol induces calpain-mediated glucose—regulated protein-94 cleavage and apoptosis in human gastric cancer cells and reduces tumor growth." PLoS.One. 2.10 (2007): e1096.
Shimo, A., et al. "Involvement of kinesin family member 2C/mitotic centromere-associated kinesin overexpression in mammary carcinogenesis." Cancer Sci. 99.1 (2008): 62-70.
Singh, S. K., et al. "Identification of a cancer stem cell in human brain tumors." Cancer Res. 63.18 (2003): 5821-28.
Singh, S. K., et al. "Identification of human brain tumour initiating cells." Nature 432.7015 (2004): 396-401.
Sithanandam, G. and L. M. Anderson. "The ERBB3 receptor in cancer and cancer gene therapy." Cancer Gene Ther. 15.7 (2008): 413-48.
Sithanandam, G., et al. "Inactivation of ErbB3 by siRNA promotes apoptosis and attenuates growth and invasiveness of human lung adenocarcinoma cell line A549." Oncogene 24.11 (2005): 1847-59.
Skawran, B. et al. "Gene expression profiling in hepatocellular carcinoma: upregulation of genes in amplified a chromosome regions." Mod.Pathol. 21.5 (2008): 505-16.
Slesak, B., et al. "Expression of epidermal growth factor receptor family proteins (EGFR, c-erbB-2 and c-erbB-3) in gastric cancer and chronic gastritis." Anticancer Res 18.4A (1998): 2727-32.
Small, E. J., et al. "Placebo-controlled phase III trial of immunologic therapy with sipuleucel-T (APC8015) in patients with metastatic, asymptomatic hormone refractory prostate cancer." J Clin Oncol. 24.19 (2006): 3089-94.
Smith, L. M., et al. "CD133/prominin-1 is a potential therapeutic target for antibody-drug conjugates in hepatocellular and gastric cancers." Br.J Cancer 99.1 (2008): 100-09.
Smith, M. J., et al. "Analysis of differential gene expression in colorectal cancer and stroma using fluorescence-activated cell sorting purification." Br.J Cancer 100.9 (2009): 1452-64.
Smogorzewska, A., et al. "Identification of the FANCI protein, a monoubiquitinated FANCD2 paralog required for DNA repair." Cell 129.2 (2007): 289-301.
Staehler, M., Stenzl, A., Dietrich, P. Y., Eisen, T., Haferkamp, A., Beck, J., Mayer, A., Walter, S., Singh-Jasuja, H., and Stief, C. A phase I study to evaluate safety, immunogenicity and anti-tumor activity of the multi-peptide vaccine IMA901 in renal cell carcinoma patients (RCC). Journal of Clinical Oncology, 2007 ASCO Annual Meeting Proceedings Part I vol. 25, No. 18S (Jun. 20 Supplement), 2007: 5098. Jun. 20, 2007. Ref Type: Abstract.
Stemmann, O., et al. "Dual inhibition of sister chromatid separation at metaphase." Cell 107.6 (2001): 715-26.
Suetsugu, A., et al. "Characterization of CD133+ hepatocellular carcinoma cells as cancer stem/progenitor cells." Biochem.Biophys. Res.Commun. 351.4 (2006): 820-24.
Suva, M. L., et al. "Identification of Cancer Stem Cells in Ewing's Sarcoma." Cancer Research (2009).
Swallow, C. J., et al. "Sak/Plk4 and mitotic fidelity." Oncogene 24.2 (2005): 306-12.
Tajima, Y., et al. "Gastric and intestinal phenotypic marker expression in early differentiated-type tumors of the stomach: clinicopathologic significance and genetic background." Clinical Cancer Research 12.21 (2006): 6469-79.
Szczepanowski, M., et al. "Regulation of repp86 stability by human Siah2." Biochem.Biophys.Res Commun. 362.2 (2007): 485-90.
Takaishi, S., et al. "Identification of gastric cancer stem cells using the cell surface marker CD44." Stem Cells 27.5 (2009): 1006-20.
Takayama, H., et al. "Diverse tumorigenesis associated with aberrant development in mice overexpressing hepatocyte growth factor/scatter factor." Proc.Natl.Acad.Sci.U.S.A 94.2 (1997): 701-06.
Teofili, L., et al. "Expression of the c-met proto-oncogene and its ligand, hepatocyte growth factor, in Hodgkin disease." Blood 97.4 (2001): 1063-69.
Thorsen, K., et al. "Alternative splicing in colon, bladder, and prostate cancer identified by exon array analysis." Mol. Cell Proteomics. 7.7 (2008): 1214-24.
Tirino, V., et al. "The role of CD133 in the identification and characterisation of tumour-initiating cells in non-small-cell lung cancer." Eur.J Cardiothorac.Surg 36.3 (2009): 446-53.
Topol, L., et al. "Wnt-5a inhibits the canonical Wnt pathway by promoting GSK-3-independent beta-catenin degradation." J Cell Biol. 162.5 (2003): 899-908.
Toribara, N. W., et al. "Human gastric mucin. Identification of a unique species by expression cloning." J Biol.Chem. 268.8 (1993): 5879-85.
Tsan, M. F. and B. Gao. "Heat shock protein and innate immunity." Cell Mol.Immunol. 1.4 (2004): 274-79.
Todaro, M., et al. "Colon cancer stem cells dictate tumor growth and resist cell death by production of interleukin-4." Cell Stem Cell 1.4 (2007): 389-402.
Tuck, A. B., et al. "Coexpression of hepatocyte growth factor and receptor (Met) in human breast carcinoma." Am.J. Pathol. 148.1 (1996): 225-32.
Vairaktaris, E., et al. "Association of -1171 promoter polymorphism of matrix metalloproteinase-3 with increased risk for oral cancer." Anticancer Res 27.6B (2007): 4095-100.
Vandenbroeck, K., E. Martens, and I. Alloza. "Multi-chaperone complexes regulate the folding of interferon-gamma in the endoplasmic reticulum." Cytokine 33.5 (2006): 264-73.
Walter, S., et al. "Cutting edge: predetermined avidity of human CD8 T cells expanded on calibrated MHC/anti-CD28-coated microspheres." J.Immunol. 171.10 (2003): 4974-78.
Wang, Q., et al. "Overexpression of endoplasmic reticulum molecular chaperone GRP94 and GRP78 in human lung cancer tissues and its significance." Cancer Detect.Prev. 29.6 (2005): 544-51.
Wang, R., et al. "Activation of the Met receptor by cell attachment induces and sustains hepatocellular carcinomas in transgenic mice." J.Cell Biol. 153.5 (2001): 1023-34.
Wang, R. Q. and D. C. Fang. "Effects of Helicobacter pylori infection on mucin expression in gastric carcinoma and pericancerous tissues." J Gastroenterol.Hepatol. 21.2 (2006): 425-31.
Wang, S., et al. "IQGAP3, a novel effector of Rac1 and Cdc42, regulates neurite outgrowth." J Cell Sci. 120.Pt 4 (2007): 567-77.
Wang, X., et al. "Immunolocalisation of heat shock protein 72 and glycoprotein 96 in colonic adenocarcinoma." Acta Histochem. 110.2 (2008): 117-23.
Wang, X. P., et al. "Expression and significance of heat shock protein 70 and glucose-regulated protein 94 in human esophageal carcinoma." World J Gastroenterol. 11.3 (2005): 429-32.
Wang, X. P., et al. "Correlation between clinicopathology and expression of heat shock protein 70 and glucose-regulated protein 94 in human colonic adenocarcinoma." World J Gastroenterol. 11.7 (2005): 1056-59.
Wang, X. P., Q. X. Wang, and X. P. Ying. "Correlation between clinicopathology and expression of heat shock protein 72 and glycoprotein 96 in human gastric adenocarcinoma." Tohoku J Exp.Med 212.1 (2007): 35-41.
Weinschenk, T., et al. "Integrated functional genomics approach for the design of patient-individual antitumor vaccines." Cancer Res. 62.20 (2002): 5818-27.
White, C. D., M. D. Brown, and D. B. Sacks. "IQGAPs in cancer: a family of scaffold proteins underlying tumorigenesis." FEBS Lett. 583.12 (2009): 1817-24.
Wicks, S. J., et al. "Reversible ubiquitination regulates the Smad/TGF-beta signalling pathway." Biochem.Soc Trans. 34.Pt 5 (2006): 761-63.
Wicks, S. J., et al. "The deubiquitinating enzyme UCH37 interacts with Smads and regulates TGF-beta signalling." Oncogene 24.54 (2005): 8080-84.
Yajima, S., et al. "Expression profiling of fecal colonocytes for RNA-based screening of colorectal cancer." Int J Oncol 31.5 (2007): 1029-37.
Yang, L., et al. "IL-21 and TGF-beta are required for differentiation of human T(H)17 cells." Nature (2008).
Yang, S., et al. "Molecular basis of the differences between normal and tumor tissues of gastric cancer." Biochim. Biophys.Acta 1772.9 (2007): 1033-40.

(56) References Cited

OTHER PUBLICATIONS

Yao, D. F., et al. "Abnormal expression of HSP gp96 associated with HBV replication in human hepatocellular carcinoma." Hepatobiliary. Pancreat.Dis.Int 5.3 (2006): 381-86.

* cited by examiner

Fig. 1, cont'd:
C
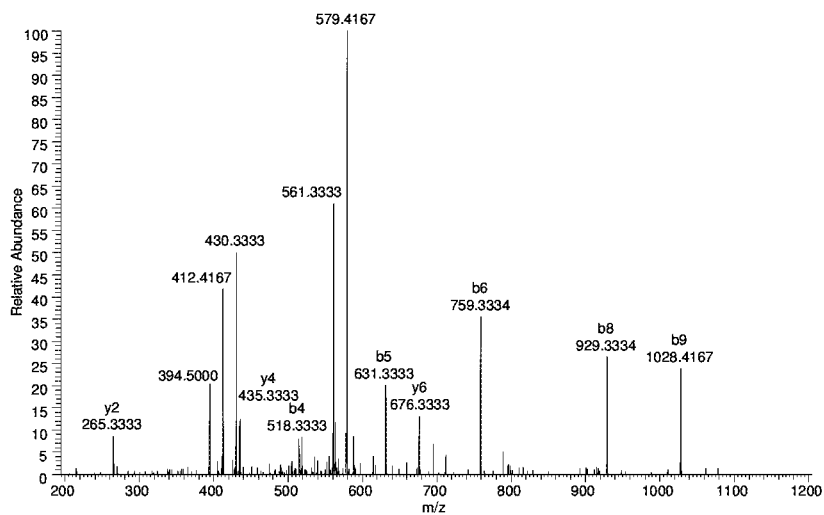
D
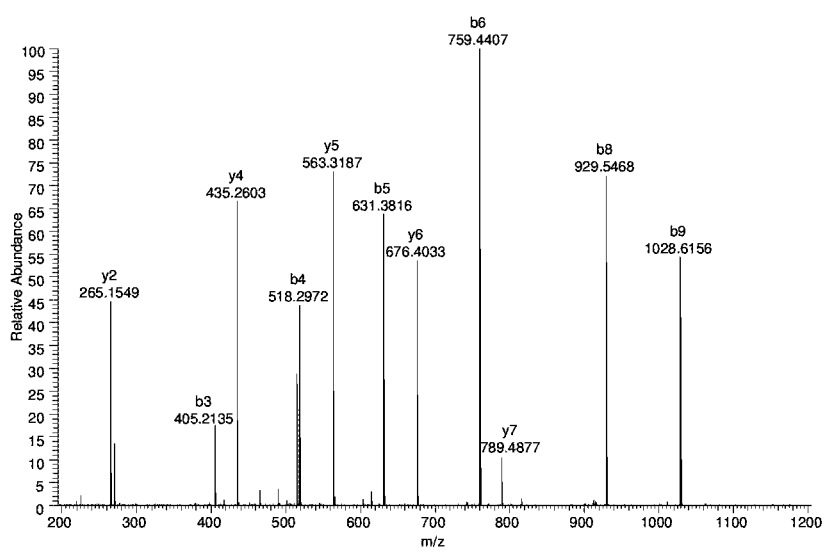

a)

b)

SEQUENCE LISTING

```
<160> NUMBER OF SEQ ID NOS: 95

<210> SEQ ID NO 1
<211> LENGTH: 10
<212> TYPE: PRT
<213> ORGANISM: Homo sapiens

<400> SEQUENCE: 1

Leu Tyr Gln Ile Leu Gln Gly Ile Val Phe
1               5                   10

<210> SEQ ID NO 2
<211> LENGTH: 9
<212> TYPE: PRT
<213> ORGANISM: Homo sapiens

<400> SEQUENCE: 2

Ser Tyr Asn Pro Leu Trp Leu Arg Ile
1               5

<210> SEQ ID NO 3
<211> LENGTH: 9
<212> TYPE: PRT
<213> ORGANISM: Homo sapiens

<400> SEQUENCE: 3

Asn Tyr Leu Pro Phe Ile Met Glu Leu
1               5

<210> SEQ ID NO 4
<211> LENGTH: 9
<212> TYPE: PRT
<213> ORGANISM: Homo sapiens

<400> SEQUENCE: 4

Ser Tyr Ile Asp Val Leu Pro Glu Phe
1               5

<210> SEQ ID NO 5
<211> LENGTH: 9
<212> TYPE: PRT
<213> ORGANISM: Homo sapiens
```

```
<400> SEQUENCE: 5

Ser Tyr Ile Ile Asp Pro Leu Asn Leu
1               5

<210> SEQ ID NO 6
<211> LENGTH: 10
<212> TYPE: PRT
<213> ORGANISM: Homo sapiens

<400> SEQUENCE: 6

Val Trp Ser Asp Val Thr Pro Leu Thr Phe
1               5                   10

<210> SEQ ID NO 7
<211> LENGTH: 9
<212> TYPE: PRT
<213> ORGANISM: Homo sapiens

<400> SEQUENCE: 7

Asn Tyr Leu Leu Tyr Val Ser Asn Phe
1               5

<210> SEQ ID NO 8
<211> LENGTH: 9
<212> TYPE: PRT
<213> ORGANISM: Homo sapiens

<400> SEQUENCE: 8

Val Tyr Thr Thr Ser Tyr Gln Gln Ile
1               5

<210> SEQ ID NO 9
<211> LENGTH: 9
<212> TYPE: PRT
<213> ORGANISM: Homo sapiens

<400> SEQUENCE: 9

His Tyr Lys Pro Thr Pro Leu Tyr Phe
1               5

<210> SEQ ID NO 10
<211> LENGTH: 10
<212> TYPE: PRT
<213> ORGANISM: Homo sapiens

<400> SEQUENCE: 10

Tyr Tyr Asn Ala Ala Gly Phe Asn Lys Leu
1               5                   10

<210> SEQ ID NO 11
<211> LENGTH: 9
<212> TYPE: PRT
<213> ORGANISM: Homo sapiens

<400> SEQUENCE: 11

Ala Tyr Leu Val Tyr Thr Asp Arg Leu
1               5

<210> SEQ ID NO 12
<211> LENGTH: 9
<212> TYPE: PRT
<213> ORGANISM: Homo sapiens
```

```
<400> SEQUENCE: 12

Phe Tyr Ile Ser Pro Val Asn Lys Leu
1               5

<210> SEQ ID NO 13
<211> LENGTH: 9
<212> TYPE: PRT
<213> ORGANISM: Homo sapiens

<400> SEQUENCE: 13

Val Tyr Gly Ile Arg Leu Glu His Phe
1               5

<210> SEQ ID NO 14
<211> LENGTH: 9
<212> TYPE: PRT
<213> ORGANISM: Homo sapiens

<400> SEQUENCE: 14

Thr Tyr Gly Asn Leu Leu Asp Tyr Leu
1               5

<210> SEQ ID NO 15
<211> LENGTH: 9
<212> TYPE: PRT
<213> ORGANISM: Homo sapiens

<400> SEQUENCE: 15

Asn Tyr Glu Glu Thr Phe Pro His Ile
1               5

<210> SEQ ID NO 16
<211> LENGTH: 9
<212> TYPE: PRT
<213> ORGANISM: Homo sapiens

<400> SEQUENCE: 16

Arg Tyr Leu Trp Ala Thr Val Thr Ile
1               5

<210> SEQ ID NO 17
<211> LENGTH: 9
<212> TYPE: PRT
<213> ORGANISM: Homo sapiens

<400> SEQUENCE: 17

Val Tyr Phe Ser Lys Ser Glu Gln Leu
1               5

<210> SEQ ID NO 18
<211> LENGTH: 9
<212> TYPE: PRT
<213> ORGANISM: Homo sapiens

<400> SEQUENCE: 18

Val Phe Ile Phe Lys Gly Asn Gln Phe
1               5

<210> SEQ ID NO 19
<211> LENGTH: 9
<212> TYPE: PRT
<213> ORGANISM: Homo sapiens
```

<400> SEQUENCE: 19

Arg Phe Leu Ser Gly Ile Ile Asn Phe
1               5

<210> SEQ ID NO 20
<211> LENGTH: 9
<212> TYPE: PRT
<213> ORGANISM: Homo sapiens

<400> SEQUENCE: 20

Gln Tyr Ala Ser Arg Phe Val Gln Leu
1               5

<210> SEQ ID NO 21
<211> LENGTH: 9
<212> TYPE: PRT
<213> ORGANISM: Homo sapiens

<400> SEQUENCE: 21

Lys Tyr Leu Thr Val Lys Asp Tyr Leu
1               5

<210> SEQ ID NO 22
<211> LENGTH: 9
<212> TYPE: PRT
<213> ORGANISM: Homo sapiens

<400> SEQUENCE: 22

Val Tyr Asn Pro Thr Pro Asn Ser Leu
1               5

<210> SEQ ID NO 23
<211> LENGTH: 9
<212> TYPE: PRT
<213> ORGANISM: Homo sapiens

<400> SEQUENCE: 23

Ser Tyr Leu Gln Ala Ala Asn Ala Leu
1               5

<210> SEQ ID NO 24
<211> LENGTH: 9
<212> TYPE: PRT
<213> ORGANISM: Homo sapiens

<400> SEQUENCE: 24

Phe Tyr Gln Pro Lys Ile Gln Gln Phe
1               5

<210> SEQ ID NO 25
<211> LENGTH: 9
<212> TYPE: PRT
<213> ORGANISM: Homo sapiens

<400> SEQUENCE: 25

Tyr Tyr Lys Asn Ile Gly Leu Gly Phe
1               5

<210> SEQ ID NO 26
<211> LENGTH: 9
<212> TYPE: PRT
<213> ORGANISM: Homo sapiens

```
<400> SEQUENCE: 26

Ala Tyr Ala Ile Ile Lys Glu Glu Leu
1               5

<210> SEQ ID NO 27
<211> LENGTH: 9
<212> TYPE: PRT
<213> ORGANISM: Homo sapiens

<400> SEQUENCE: 27

Leu Tyr Pro Glu Val Phe Glu Lys Phe
1               5

<210> SEQ ID NO 28
<211> LENGTH: 10
<212> TYPE: PRT
<213> ORGANISM: Homo sapiens

<400> SEQUENCE: 28

Lys Tyr Asn Asp Thr Phe Trp Lys Glu Phe
1               5                   10

<210> SEQ ID NO 29
<211> LENGTH: 10
<212> TYPE: PRT
<213> ORGANISM: Homo sapiens

<400> SEQUENCE: 29

Val Phe Asp Thr Ala Ile Ala His Leu Phe
1               5                   10

<210> SEQ ID NO 30
<211> LENGTH: 9
<212> TYPE: PRT
<213> ORGANISM: Homo sapiens

<400> SEQUENCE: 30

Val Tyr Pro Asn Trp Ala Ile Gly Leu
1               5

<210> SEQ ID NO 31
<211> LENGTH: 9
<212> TYPE: PRT
<213> ORGANISM: Homo sapiens

<400> SEQUENCE: 31

Val Tyr Lys Val Val Gly Asn Leu Leu
1               5

<210> SEQ ID NO 32
<211> LENGTH: 9
<212> TYPE: PRT
<213> ORGANISM: Homo sapiens

<400> SEQUENCE: 32

Val Tyr Ile Glu Lys Asn Asp Lys Leu
1               5

<210> SEQ ID NO 33
<211> LENGTH: 10
<212> TYPE: PRT
<213> ORGANISM: Homo sapiens
```

```
<400> SEQUENCE: 33

Ile Tyr Asn Gly Lys Leu Phe Asp Leu Leu
1               5                   10

<210> SEQ ID NO 34
<211> LENGTH: 9
<212> TYPE: PRT
<213> ORGANISM: Homo sapiens

<400> SEQUENCE: 34

Gln Tyr Ile Asp Lys Leu Asn Glu Leu
1               5

<210> SEQ ID NO 35
<211> LENGTH: 11
<212> TYPE: PRT
<213> ORGANISM: Homo sapiens

<400> SEQUENCE: 35

Met Tyr Met Thr Val Ser Ile Ile Asp Arg Phe
1               5                   10

<210> SEQ ID NO 36
<211> LENGTH: 9
<212> TYPE: PRT
<213> ORGANISM: Homo sapiens

<400> SEQUENCE: 36

Arg Tyr Leu Pro Gln Cys Ser Tyr Phe
1               5

<210> SEQ ID NO 37
<211> LENGTH: 9
<212> TYPE: PRT
<213> ORGANISM: Homo sapiens

<400> SEQUENCE: 37

Ile Tyr Ala Pro Lys Leu Gln Glu Phe
1               5

<210> SEQ ID NO 38
<211> LENGTH: 9
<212> TYPE: PRT
<213> ORGANISM: Homo sapiens

<400> SEQUENCE: 38

Ile Tyr Pro Asp Ala Ser Leu Leu Ile
1               5

<210> SEQ ID NO 39
<211> LENGTH: 9
<212> TYPE: PRT
<213> ORGANISM: Homo sapiens

<400> SEQUENCE: 39

Val Tyr Leu Leu Asn Ser Thr Thr Leu
1               5

<210> SEQ ID NO 40
<211> LENGTH: 9
<212> TYPE: PRT
<213> ORGANISM: Homo sapiens
```

```
<400> SEQUENCE: 40

Ile Tyr Leu Glu Val Ile His Asn Leu
1               5

<210> SEQ ID NO 41
<211> LENGTH: 9
<212> TYPE: PRT
<213> ORGANISM: Homo sapiens

<400> SEQUENCE: 41

Ala Tyr Pro Thr Val Lys Phe Tyr Phe
1               5

<210> SEQ ID NO 42
<211> LENGTH: 9
<212> TYPE: PRT
<213> ORGANISM: Homo sapiens

<400> SEQUENCE: 42

Ile Phe Ser Lys Ile Val Ser Leu Phe
1               5

<210> SEQ ID NO 43
<211> LENGTH: 9
<212> TYPE: PRT
<213> ORGANISM: Homo sapiens

<400> SEQUENCE: 43

Tyr Tyr Tyr Val Gly Phe Ala Tyr Leu
1               5

<210> SEQ ID NO 44
<211> LENGTH: 9
<212> TYPE: PRT
<213> ORGANISM: Homo sapiens

<400> SEQUENCE: 44

Arg Tyr Leu Glu Gly Thr Ser Cys Ile
1               5

<210> SEQ ID NO 45
<211> LENGTH: 11
<212> TYPE: PRT
<213> ORGANISM: Homo sapiens

<400> SEQUENCE: 45

Thr Tyr Leu Pro Thr Asn Ala Ser Leu Ser Phe
1               5                   10

<210> SEQ ID NO 46
<211> LENGTH: 9
<212> TYPE: PRT
<213> ORGANISM: Homo sapiens

<400> SEQUENCE: 46

Ser Tyr Ala Thr Leu Leu His Val Leu
1               5

<210> SEQ ID NO 47
<211> LENGTH: 9
<212> TYPE: PRT
<213> ORGANISM: Homo sapiens
```

<400> SEQUENCE: 47

Asp Tyr Thr Ile Gly Phe Gly Lys Phe
1               5

<210> SEQ ID NO 48
<211> LENGTH: 9
<212> TYPE: PRT
<213> ORGANISM: Homo sapiens

<400> SEQUENCE: 48

Ser Tyr Asn Val Thr Ser Val Leu Phe
1               5

<210> SEQ ID NO 49
<211> LENGTH: 9
<212> TYPE: PRT
<213> ORGANISM: Homo sapiens

<400> SEQUENCE: 49

Ser Tyr Leu Glu Leu Val Lys Ser Leu
1               5

<210> SEQ ID NO 50
<211> LENGTH: 9
<212> TYPE: PRT
<213> ORGANISM: Homo sapiens

<400> SEQUENCE: 50

Ser Tyr Gln Lys Val Ile Glu Leu Phe
1               5

<210> SEQ ID NO 51
<211> LENGTH: 9
<212> TYPE: PRT
<213> ORGANISM: Homo sapiens

<400> SEQUENCE: 51

Leu Tyr Leu Glu Asn Ile Asp Glu Phe
1               5

<210> SEQ ID NO 52
<211> LENGTH: 9
<212> TYPE: PRT
<213> ORGANISM: Homo sapiens

<400> SEQUENCE: 52

Val Tyr Ile Ser Ser Leu Ala Leu Leu
1               5

<210> SEQ ID NO 53
<211> LENGTH: 11
<212> TYPE: PRT
<213> ORGANISM: Homo sapiens

<400> SEQUENCE: 53

Arg Tyr Leu Pro Lys Gly Phe Leu Asn Gln Phe
1               5                   10

<210> SEQ ID NO 54
<211> LENGTH: 9
<212> TYPE: PRT
<213> ORGANISM: Homo sapiens

```
<400> SEQUENCE: 54

Tyr Tyr Lys Asn Ile Gly Leu Gly Phe
1               5

<210> SEQ ID NO 55
<211> LENGTH: 9
<212> TYPE: PRT
<213> ORGANISM: Homo sapiens

<400> SEQUENCE: 55

Val Tyr Thr Thr Met Ala Glu His Phe
1               5

<210> SEQ ID NO 56
<211> LENGTH: 9
<212> TYPE: PRT
<213> ORGANISM: Homo sapiens

<400> SEQUENCE: 56

Asp Tyr Ala Tyr Leu Arg Glu His Phe
1               5

<210> SEQ ID NO 57
<211> LENGTH: 10
<212> TYPE: PRT
<213> ORGANISM: Homo sapiens

<400> SEQUENCE: 57

Leu Tyr Ile Gln Thr Asp His Leu Phe Phe
1               5                   10

<210> SEQ ID NO 58
<211> LENGTH: 10
<212> TYPE: PRT
<213> ORGANISM: Homo sapiens

<400> SEQUENCE: 58

Thr Tyr Lys Tyr Val Asp Ile Asn Thr Phe
1               5                   10

<210> SEQ ID NO 59
<211> LENGTH: 9
<212> TYPE: PRT
<213> ORGANISM: Homo sapiens

<400> SEQUENCE: 59

Tyr Phe Ile Ser His Val Leu Ala Phe
1               5

<210> SEQ ID NO 60
<211> LENGTH: 9
<212> TYPE: PRT
<213> ORGANISM: Homo sapiens

<400> SEQUENCE: 60

Val Tyr Thr Lys Val Ser Ala Tyr Leu
1               5

<210> SEQ ID NO 61
<211> LENGTH: 9
<212> TYPE: PRT
<213> ORGANISM: Homo sapiens
```

```
<400> SEQUENCE: 61

Val Tyr Lys Glu Thr Cys Ile Ser Phe
1               5

<210> SEQ ID NO 62
<211> LENGTH: 9
<212> TYPE: PRT
<213> ORGANISM: Homo sapiens

<400> SEQUENCE: 62

Ala Leu Tyr Asp Ser Val Ile Leu Leu
1               5

<210> SEQ ID NO 63
<211> LENGTH: 9
<212> TYPE: PRT
<213> ORGANISM: Homo sapiens

<400> SEQUENCE: 63

Lys Ile Gln Glu Ile Leu Thr Gln Val
1               5

<210> SEQ ID NO 64
<211> LENGTH: 9
<212> TYPE: PRT
<213> ORGANISM: Homo sapiens

<400> SEQUENCE: 64

Leu Ala Asp Glu Thr Leu Leu Lys Val
1               5

<210> SEQ ID NO 65
<211> LENGTH: 9
<212> TYPE: PRT
<213> ORGANISM: Homo sapiens

<400> SEQUENCE: 65

Ala Met Ser Ser Lys Phe Phe Leu Val
1               5

<210> SEQ ID NO 66
<211> LENGTH: 9
<212> TYPE: PRT
<213> ORGANISM: Homo sapiens

<400> SEQUENCE: 66

Tyr Val Tyr Gln Asn Asn Ile Tyr Leu
1               5

<210> SEQ ID NO 67
<211> LENGTH: 9
<212> TYPE: PRT
<213> ORGANISM: Homo sapiens

<400> SEQUENCE: 67

Val Leu Glu Asp Leu Glu Val Thr Val
1               5

<210> SEQ ID NO 68
<211> LENGTH: 9
<212> TYPE: PRT
<213> ORGANISM: Homo sapiens
```

```
<400> SEQUENCE: 68

Phe Leu Leu Asp Gly Ser Ala Asn Val
1               5

<210> SEQ ID NO 69
<211> LENGTH: 9
<212> TYPE: PRT
<213> ORGANISM: Homo sapiens

<400> SEQUENCE: 69

Asn Leu Leu Asp Leu Asp Tyr Glu Leu
1               5

<210> SEQ ID NO 70
<211> LENGTH: 9
<212> TYPE: PRT
<213> ORGANISM: Homo sapiens

<400> SEQUENCE: 70

Phe Leu Ile Asp Ser Ser Glu Gly Val
1               5

<210> SEQ ID NO 71
<211> LENGTH: 9
<212> TYPE: PRT
<213> ORGANISM: Homo sapiens

<400> SEQUENCE: 71

Ala Leu Asp Glu Gly Asp Ile Ala Leu
1               5

<210> SEQ ID NO 72
<211> LENGTH: 11
<212> TYPE: PRT
<213> ORGANISM: Homo sapiens

<400> SEQUENCE: 72

Ala Leu Asn Glu Glu Ala Gly Arg Leu Leu Leu
1               5                   10

<210> SEQ ID NO 73
<211> LENGTH: 9
<212> TYPE: PRT
<213> ORGANISM: Homo sapiens

<400> SEQUENCE: 73

Ile Leu Ser Pro Thr Val Val Ser Ile
1               5

<210> SEQ ID NO 74
<211> LENGTH: 9
<212> TYPE: PRT
<213> ORGANISM: Homo sapiens

<400> SEQUENCE: 74

Lys Leu Leu Thr Glu Val His Ala Ala
1               5

<210> SEQ ID NO 75
<211> LENGTH: 9
<212> TYPE: PRT
<213> ORGANISM: Homo sapiens
```

```
<400> SEQUENCE: 75

Ala Leu Val Gln Asp Leu Ala Lys Ala
1               5

<210> SEQ ID NO 76
<211> LENGTH: 9
<212> TYPE: PRT
<213> ORGANISM: Homo sapiens

<400> SEQUENCE: 76

Ile Leu Gln Asp Arg Leu Asn Gln Val
1               5

<210> SEQ ID NO 77
<211> LENGTH: 9
<212> TYPE: PRT
<213> ORGANISM: Homo sapiens

<400> SEQUENCE: 77

Thr Leu Asp Pro Arg Ser Phe Leu Leu
1               5

<210> SEQ ID NO 78
<211> LENGTH: 9
<212> TYPE: PRT
<213> ORGANISM: Homo sapiens

<400> SEQUENCE: 78

Thr Leu Asp Asp Leu Leu Leu Tyr Ile
1               5

<210> SEQ ID NO 79
<211> LENGTH: 11
<212> TYPE: PRT
<213> ORGANISM: Homo sapiens

<400> SEQUENCE: 79

Ser Leu Leu Ala Gln Asn Thr Ser Trp Leu Leu
1               5                   10

<210> SEQ ID NO 80
<211> LENGTH: 9
<212> TYPE: PRT
<213> ORGANISM: Homo sapiens

<400> SEQUENCE: 80

Ser Leu Ala Glu Val Asn Thr Gln Leu
1               5

<210> SEQ ID NO 81
<211> LENGTH: 9
<212> TYPE: PRT
<213> ORGANISM: Homo sapiens

<400> SEQUENCE: 81

Ala Leu Asp Gly Phe Val Met Val Leu
1               5

<210> SEQ ID NO 82
<211> LENGTH: 9
<212> TYPE: PRT
<213> ORGANISM: Homo sapiens
```

```
<400> SEQUENCE: 82

Gly Val Asp Asp Ala Phe Tyr Thr Leu
1               5

<210> SEQ ID NO 83
<211> LENGTH: 9
<212> TYPE: PRT
<213> ORGANISM: Homo sapiens

<400> SEQUENCE: 83

Tyr Val Asp Pro Val Ile Thr Ser Ile
1               5

<210> SEQ ID NO 84
<211> LENGTH: 9
<212> TYPE: PRT
<213> ORGANISM: Homo sapiens

<400> SEQUENCE: 84

Tyr Leu Leu Ser Tyr Ile Gln Ser Ile
1               5

<210> SEQ ID NO 85
<211> LENGTH: 9
<212> TYPE: PRT
<213> ORGANISM: Homo sapiens

<400> SEQUENCE: 85

Gln Ile Asp Asp Val Thr Ile Lys Ile
1               5

<210> SEQ ID NO 86
<211> LENGTH: 10
<212> TYPE: PRT
<213> ORGANISM: Homo sapiens

<400> SEQUENCE: 86

Tyr Leu Tyr Gly Gln Thr Thr Thr Tyr Leu
1               5                   10

<210> SEQ ID NO 87
<211> LENGTH: 9
<212> TYPE: PRT
<213> ORGANISM: Homo sapiens

<400> SEQUENCE: 87

Lys Leu Asp Glu Thr Gly Asn Ser Leu
1               5

<210> SEQ ID NO 88
<211> LENGTH: 9
<212> TYPE: PRT
<213> ORGANISM: Homo sapiens

<400> SEQUENCE: 88

Arg Leu Asp Asp Leu Lys Met Thr Val
1               5

<210> SEQ ID NO 89
<211> LENGTH: 9
<212> TYPE: PRT
<213> ORGANISM: Homo sapiens
```

```
<400> SEQUENCE: 89

Leu Thr Asp Glu Ile Leu Thr Tyr Val
1               5

<210> SEQ ID NO 90
<211> LENGTH: 9
<212> TYPE: PRT
<213> ORGANISM: Homo sapiens

<400> SEQUENCE: 90

Ile Leu Ile Asp Trp Leu Val Gln Val
1               5

<210> SEQ ID NO 91
<211> LENGTH: 10
<212> TYPE: PRT
<213> ORGANISM: Homo sapiens

<400> SEQUENCE: 91

Val Leu Tyr Gly Pro Asp Val Pro Thr Ile
1               5                   10

<210> SEQ ID NO 92
<211> LENGTH: 11
<212> TYPE: PRT
<213> ORGANISM: Homo sapiens

<400> SEQUENCE: 92

Ser Ile Phe Gly Glu Asp Ala Leu Ala Asn Val
1               5                   10

<210> SEQ ID NO 93
<211> LENGTH: 9
<212> TYPE: PRT
<213> ORGANISM: Homo sapiens

<400> SEQUENCE: 93

Lys Leu Leu Glu Tyr Ile Glu Glu Ile
1               5

<210> SEQ ID NO 94
<211> LENGTH: 9
<212> TYPE: PRT
<213> ORGANISM: Homo sapiens

<400> SEQUENCE: 94

Lys Ile Leu Glu Asp Val Val Gly Val
1               5

<210> SEQ ID NO 95
<211> LENGTH: 10
<212> TYPE: PRT
<213> ORGANISM: Homo sapiens

<400> SEQUENCE: 95

Lys Ile Phe Asp Glu Ile Leu Val Asn Ala
1               5                   10
```

IMMUNOTHERAPY AGAINST SEVERAL TUMORS INCLUDING GASTROINTESTINAL AND GASTRIC CANCER

RELATED APPLICATIONS

This application is continuation of U.S. application Ser. No. 14/615,539, filed Feb. 6, 2015, which is divisional of U.S. application Ser. No. 13/051,665 (now U.S. Pat. No. 9,101,585), filed Mar. 18, 2011, which claims priority to U.S. Provisional Patent Application 61/315,704, filed Mar. 19, 2010, and UK patent application GB1004551.6, filed on Mar. 19, 2010, the entire contents of which are hereby incorporated by reference.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2332.03(a)), a Sequence Listing in the form of an ASCII-compliant text file (entitled "Sequence_Listing_2912919-023007_ST25.txt" created on Jun. 23, 2017, and 14,757 bytes in size) is submitted concurrently with the instant application, and the entire contents of the Sequence Listing are incorporated herein by reference.

FIELD OF THE INVENTION

The present invention relates to peptides, nucleic acids and cells for use in immunotherapeutic methods. In particular, the present invention relates to the immunotherapy of cancer. The present invention furthermore relates to tumor-associated epitopes recognized by CD8+ T cells, alone or in combination with other tumor-associated peptides that serve as active pharmaceutical ingredients of vaccine compositions that stimulate anti-tumor immune responses. The present invention relates to 33 novel peptide sequences and their variants derived from HLA class I molecules of human tumor cells that can be used in vaccine compositions for eliciting anti-tumor immune responses, particularly cytotoxic T cell (CTL) responses.

BACKGROUND OF THE INVENTION

Gastric cancer is a disease in which malignant cells form in the lining of the stomach. Stomach or gastric cancer can develop in any part of the stomach and may spread throughout the stomach and to other organs; particularly the esophagus, lungs and the liver. Stomach cancer is the fourth most common cancer worldwide with 930,000 cases diagnosed in 2002. It is a disease with a high death rate (~800,000 per year) making it the second most common cause of cancer death worldwide after lung cancer. It is more common in men and occurs more often in Asian countries and in developing countries. (http://www.who.int/mediacentre/factsheets/fs297/en/.)

It represents roughly 2% (25,500 cases) of all new cancer cases yearly in the United States, but it is more common in other countries. It is the leading cancer type in Korea, with 20.8% of malignant neoplasms. In Japan gastric cancer remains the most common cancer for men. Each year in the United States, about 13,000 men and 8,000 women are diagnosed with stomach cancer. Most are over 70 years old. Stomach cancer is the fourth most common cancer worldwide, after cancers of the lung, breast, and colon and rectum. Furthermore, stomach cancer remains the second most common cause of death from cancer. The American Cancer Society estimates that in 2007 there were an estimated one million new cases, nearly 70% of them in developing countries, and about 800,000 deaths (http://www.cancer.org/downloads/STT/Global_Facts_and Figures_2007_rev2.pdf.)

Tremendous geographic variation exists in the incidence of this disease around the world. Rates of the disease are highest in Asia and parts of South America and lowest in North America. The highest death rates are recorded in Chile, Japan, South America, and the former Soviet Union.

Gastric cancer is often diagnosed at an advanced stage, because screening is not performed in most of the world, except in Japan (and in a limited fashion in Korea) where early detection is often achieved. Thus, it continues to pose a major challenge for healthcare professionals. Risk factors for gastric cancer are *Helicobacter pylori* (*H. pylori*) infection, smoking, high salt intake, and other dietary factors. A few gastric cancers (1% to 3%) are associated with inherited gastric cancer predisposition syndromes. E-cadherin mutations occur in approximately 25% of families with an autosomal dominant predisposition to diffuse type gastric cancers. This subset of gastric cancer has been termed hereditary diffuse gastric cancer.12 It may be useful to provide genetic counseling and to consider prophylactic gastrectomy in young, asymptomatic carriers of germ-line truncating The wall of the stomach is made up of 3 layers of tissue: the mucosal (innermost) layer, the muscularis (middle) layer, and the serosal (outermost) layer. Gastric cancer begins in the cells lining the mucosal layer and spreads through the outer layers as it grows. Four types of standard treatment are used. Treatment for gastric cancer may involve surgery, chemotherapy, radiation therapy or chemoradiation. Surgery is the primary treatment for gastric cancer. The goal of surgery is to accomplish a complete resection with negative margins (R0 resection). However, approximately 50% of patients with locoregional gastric cancer cannot undergo an R0 resection. R1 indicates microscopic residual cancer (positive margins); and R2 indicates gross (macroscopic) residual cancer but not distant disease. Patient outcome depends on the initial stage of the cancer at diagnosis (NCCN Clinical Practice Guidelines in Oncology™).

The 5-year survival rate for curative surgical resection ranges from 30-50% for patients with stage II disease and from 10-25% for patients with stage III disease. These patients have a high likelihood of local and systemic relapse. Metastasis occurs in 80-90% of individuals with stomach cancer, with a six month survival rate of 65% in those diagnosed in early stages and less than 15% of those diagnosed in late stages.

Thus, there remains a need for new efficacious and safe treatment option for gastric cancer, prostate carcinoma, oral cavity carcinomas, oral squamous carcinoma (OSCC), acute myeloid leukemia (AML), *H. pylori*-induced MALT lymphoma, colon carcinoma/colorectal cancer, glioblastoma, non-small-cell lung cancer (NSCLC), cervical carcinoma, human breast cancer, prostate cancer, colon cancer, pancreatic cancers, pancreatic ductal adenocarcinoma, ovarian cancer, hepatocellular carcinoma, liver cancer, brain tumors of different phenotypes, leukemias such as acute lymphoblastic leukemia (ALL), lung cancer, Ewing's sarcoma, endometrial cancer, head and neck squamous cell carcinoma, epithelial cancer of the larynx, oesophageal carcinoma, oral carcinoma, carcinoma of the urinary bladder, ovarian carcinomas, renal cell carcinoma, atypical meningioma, papillary thyroid carcinoma, brain tumors, salivary duct carcinoma, cervical cancer, extranodal T/NK-cell lymphomas, Non-Hodgkins Lymphoma and malignant solid tumors of the lung and breast and other tumors enhancing the well-being of the patients without using chemotherapeutic agents or other agents which may lead to severe side effects.

The present invention incorporates peptides which stimulate the immune system and act as anti-tumor-agents in a non-invasive fashion.

SUMMARY OF THE INVENTION

Stimulation of an immune response is dependent upon the presence of antigens recognised as foreign by the host immune system. The discovery of the existence of tumour associated antigens has raised the possibility of using a host's immune system to intervene in tumour growth. Various mechanisms of harnessing both the humoral and cellular arms of the immune system are currently being explored for cancer immunotherapy.

Specific elements of the cellular immune response are capable of specifically recognising and destroying tumour cells. The isolation of cytotoxic T-cells (CTLs) from tumour-infiltrating cell populations or from peripheral blood suggests that such cells play an important role in natural immune defences against cancer. CD8-positive T-cells (TCD8+) in particular, which recognise Class I molecules of the major histocompatibility complex (MHC)-bearing peptides of usually 8 to 10 amino acid residues derived from proteins or defect ribosomal products (DRIPs) located in the cytosol, play an important role in this response. The MHC-molecules of the human are also designated as human leukocyte-antigens (HLA).

There are two classes of MHC-molecules: MHC class I molecules that can be found on most cells having a nucleus. MHC molecules are composed of an alpha heavy chain and beta-2-microglobulin (MHC class I receptors) or an alpha and a beta chain (MHC class II receptors), respectively. Their three-dimensional conformation results in a binding groove, which is used for non-covalent interaction with peptides. MHC class I present peptides that result from proteolytic cleavage of predominantly endogenous proteins, DRIPs and larger peptides. MHC class II molecules can be found predominantly on professional antigen presenting cells (APCs). They primarily present peptides of exogenous or transmembrane proteins that are taken up by APCs during the course of endocytosis, and are subsequently processed. Complexes of peptide and MHC class I molecules are recognized by CD8-positive cytotoxic T-lymphocytes bearing the appropriate T-cell receptor (TCR), whereas complexes of peptide and MHC class II molecules are recognized by CD4-positive-helper-T cells bearing the appropriate TCR. It is well known that the TCR, the peptide and the MHC are thereby present in a stoichiometric amount of 1:1:1.

For a peptide to elicit a cellular immune response, it must bind to an MHC-molecule. This process is dependent on the allele of the MHC-molecule and specific polymorphisms of the amino acid sequence of the peptide. MHC-class-I-binding peptides are usually 8-12 amino acid residues in length and usually contain two conserved residues ("anchors") in their sequence that interact with the corresponding binding groove of the MHC-molecule. In this way each MHC allele has a "binding motif" determining which peptides can bind specifically to the binding groove.

In the MHC class I dependent immune reaction, peptides not only have to be able to bind to certain MHC class I molecules being expressed by tumor cells, they also have to be recognized by T cells bearing specific T cell receptors (TCR).

The antigens that are recognized by the tumor specific CTLs, that is, their epitopes, can be molecules derived from all protein classes, such as enzymes, receptors, transcription factors, etc. which are expressed and, as compared to unaltered cells of the same origin, up-regulated in cells of the respective tumor.

The current classification of tumor associated antigens (TAAs) comprises the following major groups:

a) Cancer-testis antigens: The first TAAs ever identified that can be recognized by T cells belong to this class, which was originally called cancer-testis (CT) antigens because of the expression of its members in histologically different human tumors and, among normal tissues, only in spermatocytes/spermatogonia of testis and, occasionally, in placenta. Since the cells of testis do not express class I and II HLA molecules, these antigens cannot be recognized by T cells in normal tissues and can therefore be considered as immunologically tumor-specific. Well-known examples for CT antigens are the MAGE family members or NY-ESO-1.

b) Differentiation antigens: These TAAs are shared between tumors and the normal tissue from which the tumor arose; most are found in melanomas and normal melanocytes. Many of these melanocyte lineage-related proteins are involved in the biosynthesis of melanin and are therefore not tumor specific but nevertheless are widely used for cancer immunotherapy. Examples include, but are not limited to, tyrosinase and Melan-A/MART-1 for melanoma or PSA for prostate cancer.

c) Overexpressed TAAs: Genes encoding widely expressed TAAs have been detected in histologically different types of tumors as well as in many normal tissues, generally with lower expression levels. It is possible that many of the epitopes processed and potentially presented by normal tissues are below the threshold level for T-cell recognition, while their overexpression in tumor cells can trigger an anticancer response by breaking previously established tolerance. Prominent examples for this class of TAAs are Her-2/neu, Survivin, Telomerase or WT1.

d) Tumor specific antigens: These unique TAAs arise from mutations of normal genes (such as β-catenin, CDK4, etc.). Some of these molecular changes are associated with neoplastic transformation and/or progression. Tumor specific antigens are generally able to induce strong immune responses without bearing the risk for autoimmune reactions against normal tissues. On the other hand, these TAAs are in most cases only relevant to the exact tumor on which they were identified and are usually not shared between many individual tumors.

e) TAAs arising from abnormal post-translational modifications: Such TAAs may arise from proteins which are neither specific nor overexpressed in tumors but nevertheless become tumor associated by posttranslational processes primarily active in tumors. Examples for this class arise from altered glycosylation patterns leading to novel epitopes in tumors as for MUC1 or events like protein splicing during degradation which may or may not be tumor specific.

f) Oncoviral proteins: These TAAs are viral proteins that may play a critical role in the oncogenic process and, because they are foreign (not of human origin), they can evoke a T-cell response. Examples of such proteins are the human papilloma type 16 virus proteins, E6 and E7, which are expressed in cervical carcinoma.

For proteins to be recognized by cytotoxic T-lymphocytes as tumor-specific or -associated antigens, and to be used in a therapy, particular prerequisites must be fulfilled. The antigen should be expressed mainly by tumor cells and not or in comparably small amounts by normal healthy tissues. It is furthermore desirable, that the respective antigen is not only present in a type of tumor, but also in high concentrations (i.e. copy numbers of the respective peptide per cell). Tumor-specific and tumor-associated antigens are often derived from proteins directly involved in transformation of a normal cell to a tumor cell due to a function e.g. in cell cycle control or suppression of apoptosis. Additionally, downstream targets of the proteins directly causative for a transformation may be upregulated and thus may be indirectly tumor-associated. Such indirect tumor-associated antigens may also be targets of a vaccination approach (Singh-Jasuja H., Emmerich N. P., Rammensee H. G., Cancer Immunol. Immunother. 2004 March; 453 (3): 187-95). In both cases it is essential that epitopes are present in the amino acid sequence of the antigen, since such a peptide ("immunogenic peptide") that is derived from a tumor associated antigen should lead to an in vitro or in vivo T-cell-response.

Basically, any peptide able to bind a MHC molecule may function as a T-cell epitope. A prerequisite for the induction of an in vitro or in vivo T-cell-response is the presence of a T cell with a corresponding TCR and the absence of immunological tolerance for this particular epitope.

Therefore, TAAs are a starting point for the development of a tumor vaccine. The methods for identifying and characterizing the TAAs are based on the use of CTL that can be isolated from patients or healthy subjects, or they are based on the generation of differential transcription profiles or differential peptide expression patterns between tumors and normal tissues.

However, the identification of genes over-expressed in tumor tissues or human tumor cell lines, or selectively expressed in such tissues or cell lines, does not provide precise information as to the use of the antigens being transcribed from these genes in an immune therapy. This is because only an individual subpopulation of epitopes of these antigens are suitable for such an application since a T cell with a corresponding TCR has to be present and immunological tolerance for this particular epitope needs to be absent or minimal. It is therefore important to select only those peptides from over-expressed or selectively expressed proteins that are presented in connection with MHC molecules against which a functional T cell can be found. Such a functional T cell is defined as a T cell which upon stimulation with a specific antigen can be clonally expanded and is able to execute effector functions ("effector T cell").

T-helper cells play an important role in orchestrating the effector function of CTLs in anti-tumor immunity. T-helper cell epitopes that trigger a T-helper cell response of the TH1 type support effector functions of CD8-positive killer T cells, which include cytotoxic functions directed against tumor cells displaying tumor-associated peptide/MHC complexes on their cell surfaces. In this way tumor-associated T-helper cell peptide epitopes, alone or in combination with other tumor-associated peptides, can serve as active pharmaceutical ingredients of vaccine compositions which stimulate anti-tumor immune responses.

DETAILED DESCRIPTION OF THE INVENTION

Figure 1:
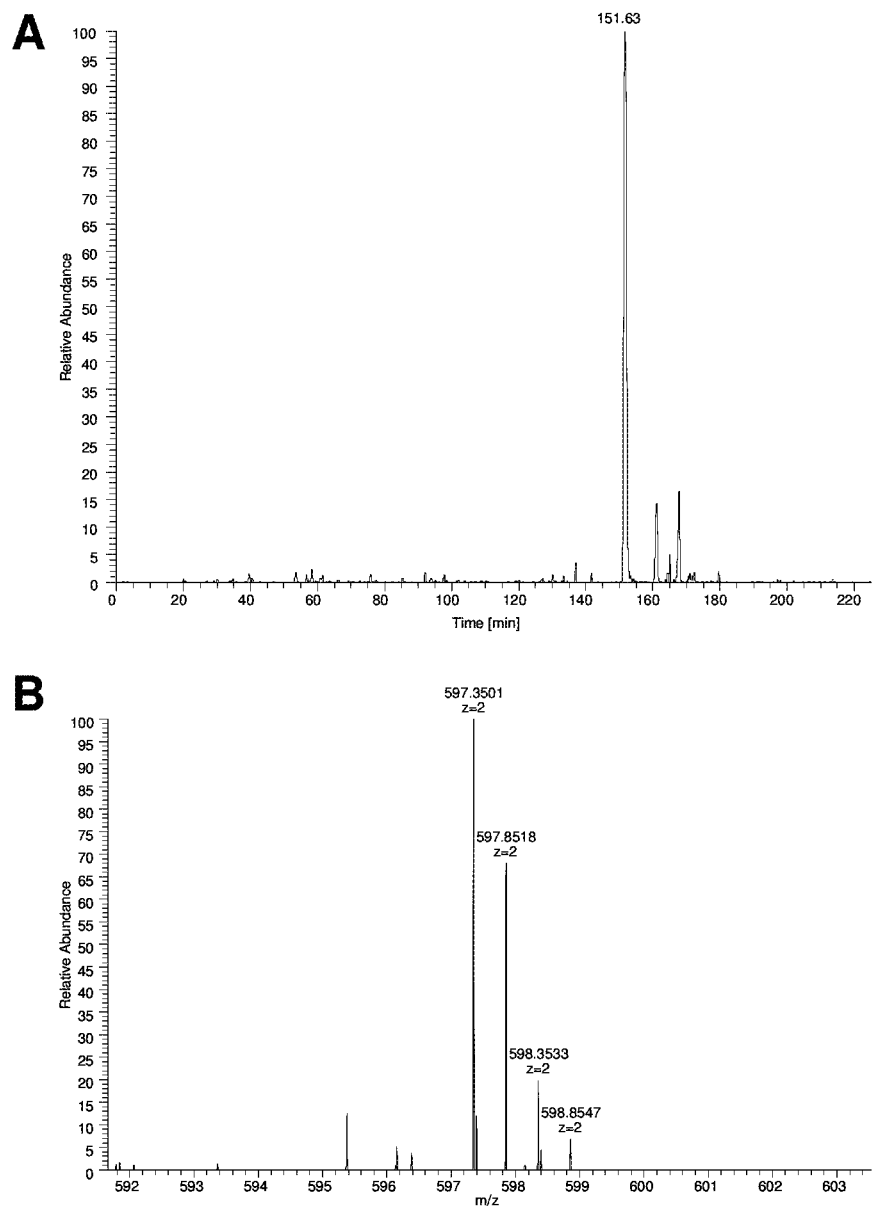
FIG. 1: Exemplary mass spectrum from CDC2-001 demonstrating its presentation on primary tumor sample GC2464. NanoESI-LCMS was performed on a peptide pool eluted from the GC sample 2464. The mass chromatogram for m/z 597.3501±0.001 Da, z=2 shows a peptide peak at the retention time 151.63 min. B) The detected peak in the mass chromatogram at 151.63 min revealed a signal of m/z 597.3501 in the MS spectrum. C) A collisionally induced decay mass spectrum from the selected precursor m/z 597.3501 recorded in the nanoESI-LCMS experiment at the given retention time confirmed the presence of CDC2-001 in the GC2464 tumor sample. D) The fragmentation pattern of the synthetic CDC2-001 reference peptide was recorded and compared to the generated natural TUMAP fragmentation pattern shown in C for sequence verification.

As used herein and except as noted otherwise, all terms are defined as given below. The term "peptide" is used herein to designate a series of amino acid residues, connected one to the other typically by peptide bonds between the alpha-amino and carbonyl groups of the adjacent amino acids. The peptides are preferably 9 amino acids in length, but can be as short as 8 amino acids in length, and as long as 10, 11, 12, 13 or 14 amino acids in length.

The term "oligopeptide" is used herein to designate a series of amino acid residues, connected one to the other typically by peptide bonds between the alpha-amino and carbonyl groups of the adjacent amino acids. The length of the oligopeptide is not critical to the invention, as long as the correct epitope or epitopes are maintained therein. The oligopeptides are typically less than about 30 amino acid residues in length, and greater than about 14 amino acids in length.

The term "polypeptide" designates a series of amino acid residues, connected one to the other typically by peptide bonds between the alpha-amino and carbonyl groups of the adjacent amino acids. The length of the polypeptide is not critical to the invention as long as the correct epitopes are maintained. In contrast to the terms peptide or oligopeptide, the term polypeptide is meant to refer to molecules containing more than about 30 amino acid residues.

A peptide, oligopeptide, protein or polynucleotide coding for such a molecule is "immunogenic" (and thus is an "immunogen" within the present invention), if it is capable of inducing an immune response. In the case of the present invention, immunogenicity is more specifically defined as the ability to induce a T-cell response. Thus, an "immunogen" would be a molecule that is capable of inducing an immune response, and in the case of the present invention, a molecule capable of inducing a T-cell response.

A T-cell "epitope" requires a short peptide that is bound to a class I MHC receptor, forming a ternary complex (MHC class I alpha chain, beta-2-microglobulin, and peptide) that can be recognized by a T cell bearing a matching T-cell receptor binding to the MHC/peptide complex with appropriate affinity. Peptides binding to MHC class I molecules are typically 8-14 amino acids in length, and most typically 9 amino acids in length.

In humans there, are three different genetic loci that encode MHC class I molecules (the MHC-molecules of the human are also designated human leukocyte antigens (HLA)): HLA-A, HLA-B, and HLA-C. HLA-A*01, HLA-A*02, and HLA-A*024 are examples of different MHC class I alleles that can be expressed from these loci.

Table 1: Expression frequencies F of HLA*A024 and the most frequent HLA*A02402 serotypes. Frequencies are deduced from haplotype frequencies Gf within the American population adapted from Mori et al. (Mori et al. 1017-27) employing the Hardy-Weinberg formula $F=1-(1-Gf)^2$. For details refer to Chanock et al. (Chanock et al. 1211-23).

| Expression frequencies of HLA*24 and A*2402 serotypes worldwide | | |
|---|---|---|
| Allele | Population | Calculated phenotype from Allele Frequency |
| A*24 | Philippines | 65% |
| A*24 | Russia Nenets | 61% |
| A*2402 | Japan | 59% |
| A*24 | Malaysia | 58% |
| A*2402 | Philippines | 54% |
| A*24 | India | 47% |
| A*24 | South Korea | 40% |
| A*24 | Sri Lanka | 37% |
| A*24 | China | 32% |
| A*2402 | India | 29% |
| A*24 | Australia West | 22% |
| A*24 | USA | 22% |
| A*24 | Russia Samara | 20% |
| A*24 | South Amerika | 20% |
| A*24 | Europa | 18% |

As used herein, reference to a DNA sequence includes both single stranded and double stranded DNA. Thus, the specific sequence, unless the context indicates otherwise, refers to the single strand DNA of such sequence, the duplex of such sequence with its complement (double stranded DNA) and the complement of such sequence. The term "coding region" refers to that portion of a gene which either naturally or normally codes for the expression product of that gene in its natural genomic environment, i.e., the region coding in vivo for the native expression product of the gene.

The coding region can be from an non-mutated ("normal"), mutated or altered gene, or can even be from a DNA sequence, or gene, wholly synthesized in the laboratory using methods well known to those of skill in the art of DNA synthesis.

The term "nucleotide sequence" refers to a heteropolymer of deoxyribonucleotides.

The nucleotide sequence coding for a particular peptide, oligopeptide, or polypeptide may be naturally occurring or they may be synthetically constructed. Generally, DNA segments encoding the peptides, polypeptides, and proteins of this invention are assembled from cDNA fragments and short oligonucleotide linkers, or from a series of oligonucleotides, to provide a synthetic gene that is capable of being expressed in a recombinant transcriptional unit comprising regulatory elements derived from a microbial or viral operon.

The term "expression product" means the polypeptide or protein that is the natural translation product of the gene and any nucleic acid sequence coding equivalents resulting from genetic code degeneracy and thus coding for the same amino acid(s).

The term "fragment", when referring to a coding sequence, means a portion of DNA comprising less than the complete coding region, whose expression product retains essentially the same biological function or activity as the expression product of the complete coding region.

The term "DNA segment" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, by using a cloning vector. Such segments are provided in the form of an open reading frame uninterrupted by internal nontranslated sequences, or introns, which are typically present in eukaryotic genes. Sequences of non-translated DNA may be present downstream from the open reading frame, where the same do not interfere with manipulation or expression of the coding regions.

The term "primer" means a short nucleic acid sequence that can be paired with one strand of DNA and provides a free 3'OH end at which a DNA polymerase starts synthesis of a deoxyribonucleotide chain.

The term "promoter" means a region of DNA involved in binding of RNA polymerase to initiate transcription.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polynucleotides, and recombinant or immunogenic polypeptides, disclosed in accordance with the present invention may also be in "purified" form. The term "purified" does not require absolute purity; rather, it is intended as a relative definition, and can include preparations that are highly purified or preparations that are only partially purified, as those terms are understood by those of skill in the relevant art. For example, individual clones isolated from a cDNA library have been conventionally purified to electrophoretic homogeneity. Purification of starting material or natural material to at least one order of magnitude, preferably two or three orders, and more preferably four or five orders of magnitude is expressly contemplated. Furthermore, a claimed polypeptide which has a purity of preferably 99.999%, or at least 99.99% or 99.9%; and even desirably 99% by weight or greater is expressly contemplated.

The nucleic acids and polypeptide expression products disclosed according to the present invention, as well as expression vectors containing such nucleic acids and/or such polypeptides, may be in "enriched form". As used herein, the term "enriched" means that the concentration of the material is at least about 2, 5, 10, 100, or 1000 times its natural concentration (for example), advantageously 0.01%, by weight, preferably at least about 0.1% by weight. Enriched preparations of about 0.5%, 1%, 5%, 10%, and 20% by weight are also contemplated. The sequences, constructs, vectors, clones, and other materials comprising the present invention can advantageously be in enriched or isolated form.

The term "active fragment" means a fragment that generates an immune response (i.e., has immunogenic activity) when administered, alone or optionally with a suitable adjuvant, to an animal, such as a mammal, for example, a rabbit or a mouse, and also including a human, such immune response taking the form of stimulating a T-cell response within the recipient animal, such as a human. Alternatively, the "active fragment" may also be used to induce a T-cell response in vitro.

As used herein, the terms "portion", "segment" and "fragment," when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. This means that any such fragment will necessarily contain as part of its amino acid sequence a segment, fragment or portion, that is substantially identical, if not exactly identical, to a sequence of SEQ ID NO: 1 to 33, which correspond to the naturally occurring, or "parent" proteins of the SEQ ID NO: 1 to 33. When used in relation to polynucleotides, these terms refer to the products produced by treatment of said polynucleotides with any of the common endonucleases.

In accordance with the present invention, the term "percent identity" or "percent identical", when referring to a sequence, means that a sequence is compared to a claimed or described sequence after alignment of the sequence to be compared (the "Compared Sequence") with the described or claimed sequence (the "Reference Sequence"). The Percent Identity is then determined according to the following formula:

Percent Identity=$100[I-(C/R)]$ wherein C is the number of differences between the Reference Sequence and the Compared Sequence over the length of alignment between the Reference Sequence and the Compared Sequence, wherein
(i) each base or amino acid in the Reference Sequence that does not have a corresponding aligned base or amino acid in the Compared Sequence and
(ii) each gap in the Reference Sequence and
(iii) each aligned base or amino acid in the Reference Sequence that is different from an aligned base or amino acid in the Compared Sequence, constitutes a difference; and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the percent identity as calculated above is about equal to or greater than a specified minimum Percent Identity then the Compared Sequence has the specified minimum percent identity to the Reference Sequence even though alignments may exist in which the herein above calculated Percent Identity is less than the specified Percent Identity.

The original peptides disclosed herein can be modified by the substitution of one or more residues at different, possibly selective, sites within the peptide chain, if not otherwise stated. Such substitutions may be of a conservative nature, for example, where one amino acid is replaced by an amino acid of similar structure and characteristics, such as where a hydrophobic amino acid is replaced by another hydrophobic amino acid. Even more conservative would be replacement of amino acids of the same or similar size and chemical nature, such as where leucine is replaced by isoleucine. In studies of sequence variations in families of naturally occurring homologous proteins, certain amino acid substitutions are more often tolerated than others, and these are often show correlation with similarities in size, charge, polarity, and hydrophobicity between the original amino acid and its replacement, and such is the basis for defining "conservative substitutions."

Conservative substitutions are herein defined as exchanges within one of the following five groups: Group 1-small aliphatic, nonpolar or slightly polar residues (Ala, Ser, Thr, Pro, Gly); Group 2-polar, negatively charged residues and their amides (Asp, Asn, Glu, Gln); Group 3-polar, positively charged residues (His, Arg, Lys); Group 4-large, aliphatic, nonpolar residues (Met, Leu, Ile, Val, Cys); and Group 5-large, aromatic residues (Phe, Tyr, Trp).

Less conservative substitutions might involve the replacement of one amino acid by another that has similar characteristics but is somewhat different in size, such as replacement of an alanine by an isoleucine residue. Highly non-conservative replacements might involve substituting an acidic amino acid for one that is polar, or even for one that is basic in character. Such "radical" substitutions cannot, however, be dismissed as potentially ineffective since chemical effects are not totally predictable and radical substitutions might well give rise to serendipitous effects not otherwise predictable from simple chemical principles.

Of course, such substitutions may involve structures other than the common L-amino acids. Thus, D-amino acids might be substituted for the L-amino acids commonly found in the antigenic peptides of the invention and yet still be encompassed by the disclosure herein. In addition, amino acids possessing non-standard R groups (i.e., R groups other than those found in the common 20 amino acids of natural proteins) may also be used for substitution purposes to produce immunogens and immunogenic polypeptides according to the present invention.

If substitutions at more than one position are found to result in a peptide with substantially equivalent or greater antigenic activity as defined below, then combinations of those substitutions will be tested to determine if the combined substitutions result in additive or synergistic effects on the antigenicity of the peptide. At most, no more than 4 positions within the peptide would simultaneously be substituted.

The term "T-cell response" means the specific proliferation and activation of effector functions induced by a peptide in vitro or in vivo. For MHC class I restricted CTLs, effector functions may be lysis of peptide-pulsed, peptide-precursor pulsed or naturally peptide-presenting target cells, secretion of cytokines, preferably Interferon-gamma, TNF-alpha, or IL-2 induced by peptide, secretion of effector molecules, preferably granzymes or perforins induced by peptide, or degranulation.

Preferably, when the CTLs specific for a peptide of SEQ IDs NO: 1 to 33 are tested against the substituted peptides, the peptide concentration at which the substituted peptides achieve half the maximal increase in lysis relative to background is no more than about 1 mM, preferably no more than about 1 μM, more preferably no more than about 1 nM, and still more preferably no more than about 100 pM, and most preferably no more than about 10 pM. It is also preferred that the substituted peptide be recognized by CTLs from more than one individual, at least two, and more preferably three individuals.

Thus, the epitopes of the present invention may be identical to naturally occurring tumor-associated or tumor-specific epitopes or may include epitopes that differ by no more than 4 residues from the reference peptide, as long as they have substantially identical antigenic activity.

Immunotherapeutic Approaches for Treatment

Stimulation of an immune response is dependent upon the presence of antigens recognized as foreign by the host immune system. The discovery of the existence of tumor associated antigens has now raised the possibility of using a host's immune system to intervene in tumor growth. Various mechanisms of harnessing both the humoral and cellular arms of the immune system are currently explored for cancer immunotherapy.

Specific elements of the cellular immune response are capable of specifically recognizing and destroying tumor cells. The isolation of cytotoxic T-cells (CTL) from tumor-infiltrating cell populations or from peripheral blood suggests that such cells play an important role in natural immune defenses against cancer. CD8-positive T-cells in particular, which recognize class I molecules of the major histocompatibility complex (MHC)-bearing peptides of usually 8 to 12 residues derived from proteins or defect ribosomal products (DRIPS) located in the cytosols, play an important role in this response. The MHC-molecules of the human are also designated as human leukocyte-antigens (HLA).

MHC class I molecules can be found on most cells having a nucleus which present peptides that result from proteolytic cleavage of mainly endogenous, cytosolic or nuclear proteins, DRIPS, and larger peptides. However, peptides derived from endosomal compartments or exogenous sources are also frequently found on MHC class I molecules. This non-classical way of class I presentation is referred to as cross-presentation in literature.

For proteins to be recognized by cytotoxic T-lymphocytes as tumor-specific or -associated antigens, and to be used in a therapy, particular prerequisites must be fulfilled. The antigen should be expressed mainly by tumor cells and not by normal healthy tissues or in comparably small amounts. It is furthermore desirable, that the respective antigen is not only present in a type of tumor, but also in high concentrations (i.e. copy numbers of the respective peptide per cell). Tumor-specific and tumor-associated antigens are often derived from proteins directly involved in transformation of a normal cell to a tumor cell due to a function e.g. in cell cycle control or apoptosis. Additionally, also downstream targets of the proteins directly causative for a transformation may be upregulated and thus be indirectly tumor-associated. Such indirectly tumor-associated antigens may also be targets of a vaccination approach. Essential is in both cases the presence of epitopes in the amino acid sequence of the antigen, since such peptide ("immunogenic peptide") that is derived from a tumor associated antigen should lead to an in vitro or in vivo T-cell-response.

Basically, any peptide able to bind a MHC molecule may function as a T-cell epitope. A prerequisite for the induction of an in vitro or in vivo T-cell-response is the presence of a T cell with a corresponding TCR and the absence of immunological tolerance for this particular epitope.

Therefore, TAAs are a starting point for the development of a tumor vaccine. The methods for identifying and characterizing the TAAs are based on the use of CTL that can be isolated from patients or healthy subjects, or they are based on the generation of differential transcription profiles or differential peptide expression patterns between tumors and normal tissues (Lemmel et al. 450-54; Weinschenk et al. 5818-27).

However, the identification of genes over-expressed in tumor tissues or human tumor cell lines, or selectively expressed in such tissues or cell lines, does not provide precise information as to the use of the antigens being transcribed from these genes in an immune therapy. This is because only an individual subpopulation of epitopes of these antigens are suitable for such an application since a T cell with a corresponding TCR has to be present and immunological tolerance for this particular epitope needs to be absent or minimal. It is therefore important to select only those peptides from over-expressed or selectively expressed proteins that are presented in connection with MHC molecules against which a functional T cell can be found. Such a functional T cell is defined as a T cell that upon stimulation with a specific antigen can be clonally expanded and is able to execute effector functions ("effector T cell").

T-helper cells play an important role in orchestrating the effector function of CTLs in anti-tumor immunity. T-helper cell epitopes that trigger a T-helper cell response of the TH1 type support effector functions of CD8-positive killer T cells, which include cytotoxic functions directed against tumor cells displaying tumor-associated peptide/MHC complexes on their cell surfaces. In this way, tumor-associated T-helper cell peptide epitopes, alone or in combination with other tumor-associated peptides, can serve as active pharmaceutical ingredients of vaccine compositions that stimulate anti-tumor immune responses.

Since both types of response, CD8 and CD4 dependent, contribute jointly and synergistically to the anti-tumor effect, the identification and characterization of tumor-associated antigens recognized by either CD8-positive CTLs (MHC class I molecule) or by CD4-positive CTLs (MHC class II molecule) is important in the development of tumor vaccines. It is therefore an object of the present invention, to provide compositions of peptides that contain peptides binding to MHC complexes of either class.

Considering the severe side-effects and expense associated with treating cancer better prognosis and diagnostic methods are desperately needed. Therefore, there is a need to identify other factors representing biomarkers for cancer in general and gastric cancer in particular. Furthermore, there is a need to identify factors that can be used in the treatment of cancer in general and gastric cancer in particular.

Furthermore there is no established therapeutic design for gastric cancer patients with biochemical relapse after radical prostatectomy, usually caused by residual tumor left in situ in the presence of locally advanced tumor growth. New therapeutic approaches that confer lower morbidity with comparable therapeutic efficacy relative to the currently available therapeutic approaches would be desirable.

The present invention provides peptides that are useful in treating gastric cancer and other tumors that overexpress the peptides of the invention. These peptides were shown by mass spectrometry to be naturally presented by HLA molecules on primary human gastric cancer samples (see example 1, and FIG. 1).

The source gene from which the peptides are derived were shown to be highly overexpressed in gastric cancer, renal cell carcinoma, colon cancer, non-small cell lung carcinoma, adenocarcinoma, prostate cancer, benign neoplasm and malignant melanoma compared with normal tissues (see example 2, and FIG. 2) demonstrating a high degree of tumor association of the peptide, i.e. these peptides are strongly presented on tumor tissue but not on normal tissues.

HLA-bound peptides can be recognized by the immune system, specifically by T lymphocytes/T cells. T cells can destroy the cells presenting the recognized HLA/peptide complex, e.g. gastric cancer cells presenting the derived peptides.

Figure 3:
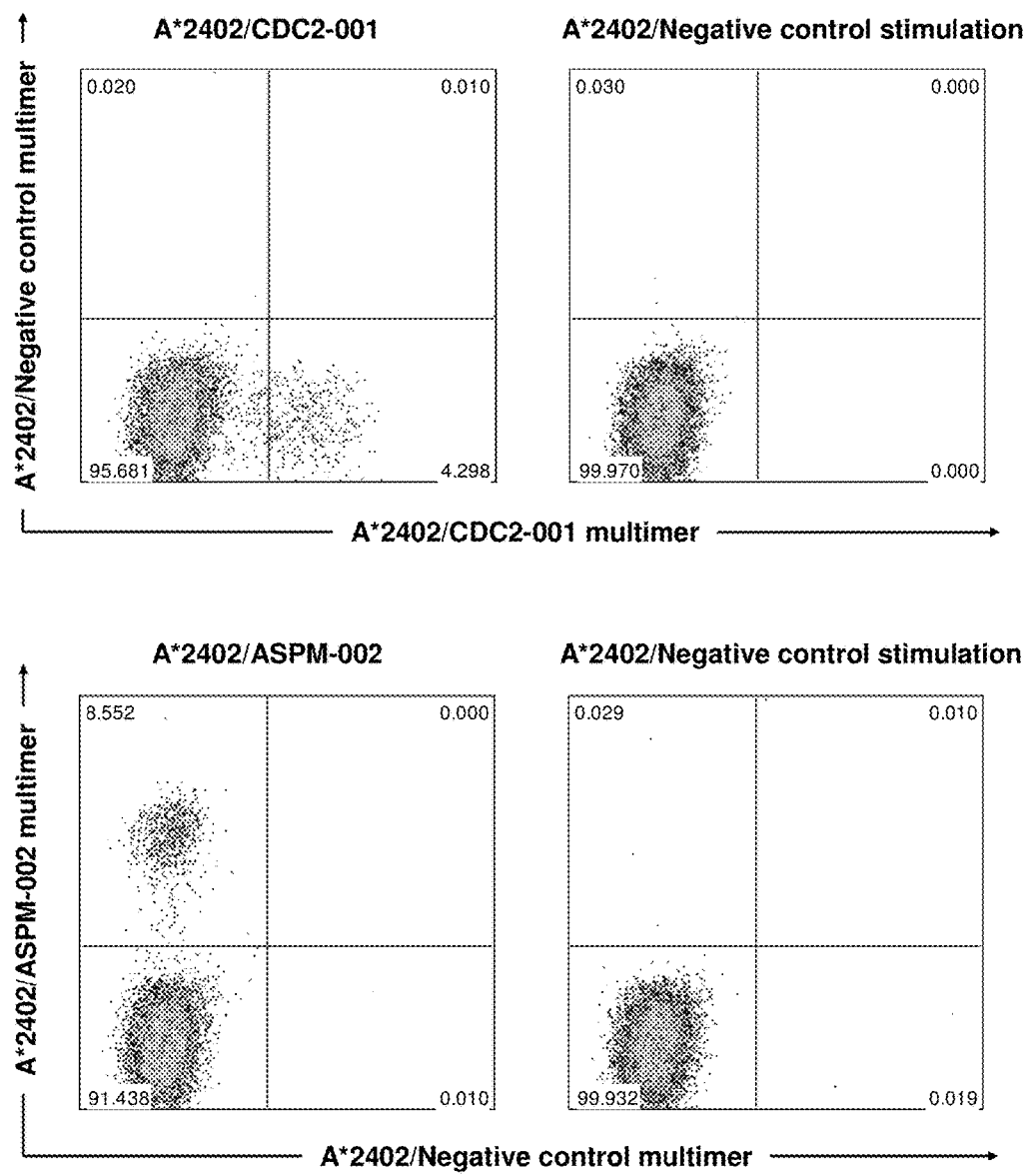
FIG. 3: Exemplary results of peptide-specific in vitro immunogenicity of class I TUMAPs. CD8+ T cells were primed using artificial APCs loaded with relevant (left panel) and irrelevant peptide (right panel), respectively. After three cycles of stimulation, the detection of peptide-reactive cells was performed by double staining with relevant plus irrelevant A*2402-multimers. Shown cells are gated on live CD8+ lymphocytes and the numbers in the plots represent percentages of multimer-positive cells.

All peptides, that were compatible with the validation platform—see example 3—, of the present invention have been shown to be capable of stimulating T cell responses (see Example 3 and FIG. 3). Thus, the peptides are useful for generating an immune response in a patient by which tumor cells can be destroyed. An immune response in a patient can be induced by direct administration of the described peptides or suitable precursor substances (e.g. elongated peptides, proteins, or nucleic acids encoding these peptides) to the patient, ideally in combination with an agent enhancing the immunogenicity (i.e. an adjuvant). The immune response originating from such a therapeutic vaccination can be expected to be highly specific against tumor cells because the target peptides of the present invention are not presented on normal tissues in comparable copy numbers, preventing the risk of undesired autoimmune reactions against normal cells in the patient.

The pharmaceutical compositions comprise the peptides either in the free form or in the form of a pharmaceutically acceptable salt. As used herein, "a pharmaceutically acceptable salt" refers to a derivative of the disclosed peptides wherein the peptide is modified by making acid or base salts of the agent. For example, acid salts are prepared from the free base (typically wherein the neutral form of the drug has a neutral —NH2 group) involving reaction with a suitable acid. Suitable acids for preparing acid salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methane sulfonic acid, ethane sulfonic acid, p-toluenesulfonic acid, salicylic acid, and the like, as well as inorganic acids, e.g., hydrochloric acid, hydrobromic acid, sulfuric acid, nitric acid phosphoric acid and the like. Conversely, preparation of basic salts of acid moieties which may be present on a peptide are prepared using a pharmaceutically acceptable base such as sodium hydroxide, potassium hydroxide, ammonium hydroxide, calcium hydroxide, trimethylamine or the like.

In an especially preferred embodiment, the pharmaceutical compositions comprise the peptides as salts of acetic acid (acetates) or hydrochloric acid (chlorides).

In addition to being useful for treating cancer, the peptides of the present invention are also useful as diagnostics. Since the peptides were generated from gastric cancer cells and since it was determined that these peptides are not present in normal tissues, these peptides can be used to diagnose the presence of a cancer.

The presence of claimed peptides on tissue biopsies can assist a pathologist in diagnosis of cancer. Detection of certain peptides by means of antibodies, mass spectrometry or other methods known in the art can tell the pathologist that the tissue is malignant or inflamed or generally diseased. Presence of groups of peptides can enable classification or sub-classification of diseased tissues.

The detection of peptides on diseased tissue specimen can enable the decision about the benefit of therapies involving the immune system, especially if T-lymphocytes are known or expected to be involved in the mechanism of action. Loss of MHC expression is a well described mechanism by which infected of malignant cells escape immunosurveillance. Thus, presence of peptides shows that this mechanism is not exploited by the analyzed cells.

The peptides might be used to analyze lymphocyte responses against those peptides such as T cell responses or antibody responses against the peptide or the peptide complexed to MHC molecules. These lymphocyte responses can be used as prognostic markers for decision on further therapy steps. These responses can also be used as surrogate markers in immunotherapy approaches aiming to induce lymphocyte responses by different means, e.g. vaccination of protein, nucleic acids, autologous materials, adoptive transfer of lymphocytes. In gene therapy settings, lymphocyte responses against peptides can be considered in the assessment of side effects. Monitoring of lymphocyte responses might also be a valuable tool for follow-up examinations of transplantation therapies, e.g. for the detection of graft versus host and host versus graft diseases.

The peptides can be used to generate and develop specific antibodies against MHC/peptide complexes. These can be used for therapy, targeting toxins or radioactive substances to the diseased tissue. Another use of these antibodies can be targeting radionuclides to the diseased tissue for imaging purposes such as PET. This use can help to detect small metastases or to determine the size and precise localization of diseased tissues.

In addition, they can be used to verify a pathologist's diagnosis of a cancer based on a biopsied sample.

Table 2 shows the peptides according to the present invention, their respective SEQ ID NO:, and the source proteins from which these peptides may arise. All peptides bind the HLA A*024 alleles.

TABLE 2

Peptides of the present invention

| SEQ ID NO: | Peptide Code | Sequence | Source Protein(s) |
|---|---|---|---|
| 1 | CDC2-001 | LYQILQGIVF | CDK1 |
| 2 | ASPM-002 | SYNPLWLRI | ASPM |
| 3 | UCHL5-001 | NYLPFIMEL | UCHL5 |
| 4 | MET-006 | SY1DVLPEF | MET |
| 5 | PROM1-001 | SYIIDPLNL | PROM1 |
| 6 | MMP11-001 | VWSDVTPLTF | MMP11 |
| 7 | MST1R-001 | NYLLYVSNF | MST1R |
| 8 | NFYB-001 | VYTTSYQQI | NFYB |
| 9 | SMC4-001 | HYKPTPLYF | SMC4 |
| 10 | UQCRB-001 | YYNAAGFNKL | UQCRB |
| 11 | PPAP2C-001 | AYLVYTDRL | PPAP2C |
| 12 | AVL9-001 | FYISPVNKL | AVL9 |
| 13 | NUF2-001 | VYGIRLEHF | NUF2 |
| 14 | ABL1-001 | TYGNLLDYL | ABL1 |
| 15 | MUC6-001 | NYEETFPHI | MUC6 |
| 16 | ASPM-001 | RYLWATVTI | ASPM |
| 17 | EPHA2-005 | VYFSKSEQL | EPHA2 |

TABLE 2-continued

Peptides of the present invention

| SEQ ID NO: | Peptide Code | Sequence | Source Protein(s) |
|---|---|---|---|
| 18 | MMP3-001 | VFIFKGNQF | MMP3 |
| 19 | NUF2-002 | RFLSGIINF | NUF2 |
| 20 | PLK4-001 | QYASRFVQL | PLK4 |
| 21 | ATAD2-002 | KYLTVKDYL | ATAD2 |
| 22 | COL12A1-001 | VYNPTPNSL | COL12A1 |
| 23 | COL6A3-001 | SYLQAANAL | COL6A3 |
| 24 | FANCI-001 | FYQPKIQQF | FANCI |
| 25 | RPS11-001 | YYKNIGLGF | RPS11 |
| 26 | ATAD2-001 | AYAIIKEEL | ATAD2 |
| 27 | ATAD2-003 | LYPEVFEKF | ATAD2 |
| 28 | HSP90B1-001 | KYNDTFWKEF | HSP90B1 |
| 29 | SIAH2-001 | VFDTAIAHLF | SIAH2 |
| 30 | SLC6A6-001 | VYPNWAIGL | SLC6A6 |
| 31 | IQGAP3-001 | VYKVVGNLL | IQGAP3 |
| 32 | ERBB3-001 | VYIEKNDKL | ERBB3 |
| 33 | KIF2C-001 | IYNGKLFDLL | KIF2C |

Further interesting HLA A*024 peptides of the invention

| SEQ ID NO: | Peptide Code | Sequence | Source Protein(s) |
|---|---|---|---|
| 34 | CCDC88A-001 | QYIDKLNEL | CCDC88A |
| 35 | CCNB1-003 | MYMTVSIIDRF | CCNB1 |
| 36 | CCND2-001 | RYLPQCSYF | CCND2 |
| 37 | CCNE2-001 | IYAPKLQEF | CCNE2 |
| 38 | CEA-010 | IYPDASLLI | CEACAM1, CEACAM5, CEACAM6 |
| 39 | CLCN3-001 | VYLLNSTTL | CLCN3 |
| 40 | DNAJC10-001 | IYLEVIHNL | DNAJC10 |
| 41 | DNAJC10-002 | AYPTVKFYF | |
| 42 | EIF253-001 | IFSKIVSLF | EIF253, LOC255308 |
| 43 | EIF3L-001 | YYYVGFAYL | EIF3L, LOC340947 |
| 44 | EPPK1-001 | RYLEGTSCI | EPPK1 |
| 45 | ERBB2-001 | TYLPTNASLSF | ERBB2 |
| 46 | GPR39-001 | SYATLLHVL | GPR39 |
| 47 | ITGB4-001 | DYTIGFGKF | ITGB4 |
| 48 | LCN2-001 | SYNVTSVLF | LCN2 |

-continued

| SEQ ID NO: | Peptide Code | Sequence | Source Protein(s) |
|---|---|---|---|
| 49 | SDHC-001 | SYLELVKSL | LOC642502, SDHC |
| 50 | PBK-001 | SYQKVIELF | PBK |
| 51 | POLD3-001 | LYLENIDEF | POLD3 |
| 52 | PSMD14-001 | VYISSLALL | PSMD14 |
| 53 | PTK2-001 | RYLPKGFLNQF | PTK2 |
| 54 | RPS11-001 | YYKNIGLGF | RPS11 |
| 55 | TSPAN1-002 | VYTTMAEHF | TSPAN1 |
| 56 | ZNF598-001 | DYAYLREHF | ZNF598 |
| 57 | ADAM10-001 | LYIQTDHLFF | ADAM10 |
| 58 | MMP12-001 | TYKYVDINTF | MMP12 |
| 59 | RRM2-001 | YFISHVLAF | RRM2 |
| 60 | TMPRSS4-001 | VYTKVSAYL | TMPRSS4 |
| 61 | TSPAN8-001 | VYKETCISF | TSPAN8 |

In another embodiment of the invention HLA A*02 binding peptides against gastric cancer are disclosed. For people which are A*02 and/or A*24 positive, mixtures of the disclosed peptides can be used for the treatment of gastric cancer. Preferred are mixtures of 2 to 20 peptides and mixtures of 2, 3, 4, 5, 6, 7, 8, 9, 10, 11, 12, 13, 14, 15, 16, 17, 18, 19 and 20 peptides.

| SEQ ID NO: | Peptide Code | Sequence | Source Protein(s) |
|---|---|---|---|
| 62 | DIO2-001 | ALYDSVILL | DIO2 |
| 63 | IGF2BP3-001 | KIQEILTQV | IGF2BP3 |
| 64 | LMNB1-001 | LADETLLKV | LMNB1 |
| 65 | WNT5A-001 | AMSSKFFLV | WNT5A |
| 66 | FAP-003 | YVYQNNIYL | FAP |
| 67 | COPG-001 | VLEDLEVTV | COPG, COPG2, TSGA13 |
| 68 | COL6A3-002 | FLLDGSANV | COL6A3 |
| 69 | COL6A3-003 | NLLDLDYEL | COL6A3 |
| 70 | COL6A3-004 | FLIDSSEGV | COL6A3 |
| 71 | PSMC2-001 | ALDEGDIAL | PSMC2 |
| 72 | UBE2S-001 | ALNEEAGRLLL | UBE2S |
| 73 | KIF11-001 | ILSPTVVSI | KIF11 |
| 74 | ADAM8-001 | KLLTEVHAA | ADAM8 |
| 75 | CCNB1-001 | ALVQDLAKA | CCNB1 |
| 76 | CDC6-001 | ILQDRLNQV | CDC6 |
| 77 | F2R-001 | TLDPRSFLL | F2R |
| 78 | OLFM4-001 | TLDDLLLYI | OLFM4 |

-continued

| SEQ ID NO: | Peptide Code | Sequence | Source Protein(s) |
|---|---|---|---|
| 79 | THY1-001 | SLLAQNTSWLL | THY1 |
| 80 | CEP250-001 | SLAEVNTQL | CEP250 |
| 81 | HIF1A-001 | ALDGFVMVL | HIF1A |
| 82 | KRAS-001 | GVDDAFYTL | KRAS |
| 83 | MET-001 | YVDPVITSI | MET |
| 84 | NCAPG-001 | YLLSYIQSI | NCAPG |
| 85 | NCAPG-002 | QIDDVTIKI | NCAPG |
| 86 | TOP-004 | YLYGQTTTYL | TOP2A |
| 87 | TOP-005 | KLDETGNSL | TOP2A |
| 88 | LAMC2-002 | RLDDLKMTV | LAMC2 |
| 89 | AHR-001 | LTDEILTYV | AHR |
| 90 | CCNB1-002 | ILIDWLVQV | CCNB1 |
| 91 | CEACAM6-001 | VLYGPDVPTI | CEACAM6 |
| 92 | COPB1-001 | SIFGEDALANV | COPB1 |
| 93 | HMMR-001 | KLLEYIEEI | HMMR |
| 94 | TPX2-001 | KILEDVVGV | TPX2 |
| 95 | TOP-001 | KIFDEILVNA | TOP2A, TOP2B |

Cell Division Cycle 2 Protein (CDC2)

The serine/threonine kinase CDC2, also known as Cdk1 (Cyclin-dependent kinase 1), plays a key role in cell cycle control. It is known as the main regulator of the G2-to-M transition. At the end of interphase, it binds to A-type cyclins. After breakdown of the nuclear envelope, A-type cyclins are replaced by cyclin B, which forms the mitosis promoting factor (MPF) with Cdc2. MPF is essential for driving cells through mitosis.

The function of Cdc2 in mitosis is non-redundant and cannot be compensated by the activity of other Cdks, such as Cdk2, 4 and 6. By contrast, Cdc2 was reported to function in other phases of the cell cycle such as the G1-S transition as well, and it is able to substitute for the "interphase Cdks". Thus, Cdc2 was proposed to be the only essential cell cycle Cdk.

Overexpression of Cdc2 was found in several cancers, often correlating with poor prognosis. Among them are prostate carcinoma, oral cavity carcinomas, oral squamous carcinoma (OSCC), acute myeloid leukemia (AML) (Qian et al.), *H. pylori*-induced MALT lymphoma (Banerjee et al. 217-25) and colon carcinoma (Yasui et al. 36-41). In gastric carcinoma, overexpression and/or enhanced activity has been reported and could play a causative role. Inhibitors of Cdc2 and other Cdks have been considered as drug candidates for cancer therapy (Shapiro 1770-83).

Abnormal Spindle-Like Microcephaly Associated Protein (ASPM)

Abnormal spindle-like microcephaly associated (ASPM) is the human orthologue of the *Drosophila* abnormal spindle (asp). It is involved in the regulation of neurogenesis, and mutation causes autosomal recessive primary microcephaly. ASPM is localized in the spindle poles during mitosis. ASPM overexpression was suggested as marker and potential therapeutic target in glioblastoma. siRNA-mediated knockdown inhibits tumor cell proliferation and neural stem cell proliferation. ASPM overexpression may also predict enhanced invasive/metastatic potential, early tumor recurrence and poor prognosis in hepatocellular carcinoma. ASPM was upregulated in immortalized cells and non-small-cell lung cancer tissues (Jung, Choi, and Kim 703-13).

Matrix Metalloproteases 3 (MMP3)

MMP3, also called progelatinase or stromelysin 1, is an endopeptidase that cleaves extracellular matrix (ECM) components such as fibronectin, laminin, elastin, the proteoglycan core protein and nonhelical regions of collagens. MMPs are important in several physiological processes requiring ECM rearrangement, such as cell migration during embryogenesis, tissue remodeling, vascularization, involution of the lactating breast and wound healing. MMP3 also plays a role in platelet aggregation. Pathological conditions involving enhanced expression and secretion of MMP3 include autoimmune inflammatory conditions and cancer.

MMP3 is over-expressed in some tumors, and plays a role in epithelial-mesenchymal transition (EMT). It might also contribute to early steps in cancerogenesis, triggering epigenetic changes that result in the generation of a malignant phenotype (Lochter et al. 180-93). Polymorphisms in the MMP3 promoter that are associated with expression levels were shown to impact risk and prognosis for some cancers like esophageal adenocarcinoma (Bradbury et al. 793-98) and oral squamous cell carcinoma (Vairaktaris et al. 4095-100) (Liu et al. 430-35). *H. pylori*-positive gastric cancer patients with enhanced MMP3- and MMP7 serum levels showed higher lymph node invasion and shorter survival. In a cohort of 74 gastric cancer patients, MMP3 was expressed in 27% of the cases, (Murray et al. 791-97).

c-Met c-Met mediates the potentially oncogenic activities of the hepatocytic growth factor (HGF)/scatter factor, including promotion of cell growth, motility, survival, extracellular matrix dissolution, and angiogenesis. Binding of HGF activates downstream signalling events including the Ras, phosphatidylinositol 3'-kinase, phospholipase Cγ, and mitogen-activated protein kinase-related pathways (Dong et al. 5911-18; Furge et al. 10722-27; Furge, Zhang, and Vande Woude 5582-89; Montesano et al. 355-65; Naldini et al. 501-04; Ponzetto et al. 4600-08). c-Met is expressed predominantly in epithelial cells. Oncogenic activation of c-Met (also in non-epithelial malignant tissues) can result from amplification/over-expression, activating mutations, acquisition of HGF/c-Met autocrine loops or constitutive phosphorylation (Di Renzo et al. 147-54; Ferracini et al. 739-49; Fischer et al. 733-39; Koochekpour et al. 5391-98; Li et al. 8125-35; Maulik et al. 41-59; Qian et al. 589-96; Ramirez et al. 635-44; Tuck et al. 225-32) (Nakaigawa et al. 3699-705). Constitutive activation of c-Met in HGF-over-expressing transgenic mice promotes broad tumorigenesis (Takayama et al. 701-06; Wang et al. 1023-34). Silencing MET results in inhibition of tumor growth and metastasis (Corso et al. 684-93). Amplification of MET has been associated with human gastric cancer progression (Lin et al. 5680-89). (Yokozaki, Yasui, and Tahara 49-95).

Ubiquitin Carboxyl-Terminal Hydrolase L5 (UCHL5)

UCHL5, also known as Ubiquitin C-terminal hydrolase (UCH37) or INO80R, is a proteasome-associated deubiquitinase. It disassembles protein-attached poly-ubiquitin chains from the distal end by cleaving the isopeptide bond between the C-terminal Cys76 and Lys48 (Nishio et al. 855-60). In the nucleus, UCHL5 is associated with the Ino80 chromatin-remodeling complex. Upon binding of a proteasome, it becomes activated and may contribute to the regulation of transcription or DNA repair that has been suggested to be mediated by Ino80 and the proteasome.

Ubiquitin specific proteases like UCHL5 are involved in several processes such as control of cell cycle progression, differentiation, DNA replication and repair, transcription, protein quality control, immune response and apoptosis. UCHL5 might contribute to malignant transformation. Its activity has been shown to be upregulated in human cervical carcinoma tissue as compared to adjacent normal tissue. It is able to deubiquitinate and thereby stabilize the TGF-beta receptor and its downstream mediators, the Smads, thereby enhancing TGF-beta signaling. Enhanced TGF-beta signaling can act as a tumor promoter in late stages of cancer progression, although it has a dual function and can also be a tumor suppressor in early stages and before initiation (Bierie and Moses 29-40; Horton et al. 138-43; Wicks et al. 8080-84; Wicks et al. 761-63).

Macrophage-Stimulating Protein Receptor (MST1R)

The MST1R (alias RON) receptor is a member of the Met family of cell surface receptor tyrosine kinases and is primarily expressed on epithelial cells and macrophages. MST1R can induce cell migration, invasion, proliferation and survival in response to its ligand. Oncogenic properties have been shown in vitro as well as in animal models in vivo, and it is often deregulated in human cancers (Dussault and Bellon, 2009). Clinical studies have shown that MST1R over-expression is associated with poor diagnosis and metastasis. MST1R expression is significant in gastric carcinoma tissue and corresponding paraneoplastic tissue, but is not observed in normal gastric mucosa (Zhou et al. 236-40). Knockdown of MST1R in prostate cancer cells results in reduced endothelial cell chemotaxis in vitro, and in reduced tumor growth and decreased microvessel density after orthotopic transplantation into the prostate in vivo. siRNA-mediated knockdown of MST1R in a highly tumorigenic colon cancer cell line led to reduced proliferation as compared with control cells.

Kinesin-Like Protein (KIF2C)

KIF2C is a microtubule depolymerase regulating proper kinetochore-microtubule attachment during spindle formation. It is important for anaphase chromosome segregation and may be required to coordinate the onset of sister centromere separation. Disturbed microtubule attachment at kinetochores leads to chromosome mis-segregation and aneuploidy, which is observed in most solid tumors (Maney et al. 67-131; Moore and Wordeman 537-46). KIF2C is over-expressed in breast cancer cells (Shimo et al. 62-70), colon cancer, colorectal cancer and gastric cancer (Nakamura et al. 543-49). A gastric cancer cell line (AZ521) that stably expressed KIF2C showed a increased proliferation and migration compared to mock-transfected cells. Elevated expression of KIF2C in gastric cancer may be associated with lymphatic invasion, lymph node metastasis, and poor prognosis. Treatment of breast cancer cells with small interfering RNA against KIF2C inhibited their growth.

Structural Maintenance of Chromosomes Proteins 4 (SMC4)

SMC proteins are chromosomal ATPases that play roles in higher-order chromosome organization and dynamics. SMC4 is a core component of the condensin complex that plays a role in chromatin condensation and has also been associated with nucleolar segregation, DNA repair, and maintenance of the chromatin scaffold. The SMC4 gene was found to be expressed highly in normal prostate and salivary gland, very weakly in colon, pancreas, and intestine, and not at all in other tissues. RNA expression was observed at high levels in many cancer cell lines and cancer specimens, including breast, prostate, colon and pancreatic cancer (Egland et al. 5929-34).

Ephrin Type-A Receptor 2 (EPAH2)

Eph receptors are a unique family of receptor tyrosine kinases (RTK) that play critical roles in embryonic patterning, neuronal targeting, and vascular development during normal embryogenesis. Stimulation of EphA2 by its ligand (ephrin-A1) results in EphA2 autophosphorylation, the stimulation reverses oncogenic transformation. Eph receptors and their ligands, the ephrins, are frequently overexpressed in a wide variety of cancers. EphA2 is frequently overexpressed and functionally altered in aggressive tumor cells, and is thought to promote tumor growth by enhancing cell-extracellular matrix adhesion, anchorage-independent growth and angiogenesis. Overexpression of EphA2 and EphrinA-1 was shown in gastric carcinoma, correlating with the depth of tumor invasion, tumor-node-metastasis (TNM) stages, lymph node metastasis and poor prognosis (Yuan et al. 2410-17).

ATAD2

ATAD2 (also known as ANCCA) is a new member of the AAA+ ATPase family proteins. It enhances the transcriptional activity of androgen receptor (AR) and estrogen receptor (ER), leading to transcription of genes including IGF1R, IRS-2, SGK1 and surviving (AR) and cyclin D1, c-myc and E2F1 (ER), respectively. It also enhances the transcriptional activity of c-Myc. ATAD2 expression is high in several human tumors, such as breast cancer, prostate cancer and osteosarcoma. Expression has been associated with poor prognosis.

AVL9

Surprisingly this protein was found as source protein, and only poor and very limited data is available about the AVL9 protein and the function of the corresponding gene.

Collagen Alpha-1(XII) Chain Protein (Col12A1)

Collagen alpha-1(XII) chain is a protein that in humans is encoded by the COL12A1 gene. This gene encodes the alpha chain of type XII collagen, a member of the FACIT (fibril-associated collagens with interrupted triple helices) collagen family. Type XII collagen is a homotrimer found in association with type I collagen, an association that is thought to modify the interactions between collagen I fibrils and the surrounding matrix. Alternatively spliced transcript variants encoding different isoforms have been identified.

Collagen Alpha-3(VI) Chain Protein (COL6A3)

COL6A3 encodes the alpha-3 chain, one of the three alpha chains of type VI collagen. The protein domains have been shown to bind extracellular matrix proteins, an interaction that explains the importance of this collagen in organizing matrix components. Remodeling of the extracellular matrix through overexpression of collagen VI contributes to cisplatin resistance in ovarian cancer cells. The presence of collagen VI correlated with tumor grade, an ovarian cancer prognostic factor (Sherman-Baust et al. 377-86). COL6A3 is overexpressed in colorectal tumour (Smith et al. 1452-64), salivary gland carcinoma (Leivo et al. 104-13) and differentially expressed in gastric cancer (Yang et al. 1033-40). COL6A3 was identified as one of seven genes with tumor-specific splice variants. The validated tumor-specific splicing alterations were highly consistent, enabling clear separation of normal and cancer samples and in some cases even of different tumor stages (Thorsen et al. 1214-24).

Fanconi Anemia, Complementation Group I (FANCI)

The FANCI protein localizes to chromatin in response to DNA damage and is involved in DNA repair (Smogorzewska et al. 289-301). Mutations in the FANCI gene cause Fanconi anemia, a genetically heterogeneous recessive disorder characterized by cytogenetic instability, hypersensitivity to DNA crosslinking agents, increased chromosomal breakage, and defective DNA repair. Alternative splicing of FANCI results in two transcript variants encoding different isoforms.

Heat Shock Protein 90 kDa Beta Member 1 (HSP90B1)

HSP90 (also known as glucose-regulated protein 94, Grp94), member 1 is a human chaperone protein. It participates in ER-associated processes: translation, protein quality control and ER-associated degradation (ERAD), ER stress sensing and calcium binding/retention of calcium in the ER (Christianson et al. 272-82; Fu and Lee 741-44). HSP90 contains the KDEL sequence typical for ER-retained proteins, but it also appears on the surface of tumor cells (Altmeyer et al. 340-49), as well as extracellularly. HSPs are known to be released from necrotic (but not apoptotic) cells and from cells stressed by various stimuli such as heat shock and oxidative stress, and can occur in circulation (Basu et al. 1539-46; Tsan and Gao 274-79). Extracellularly, HSP90 modulates (mainly stimulates) immune responses and is involved in antigen presentation. On the cell surface, it may serve as receptor for pathogen entry and/or signaling (Cabanes et al. 2827-38). In case of tumor-specific cell surface expression or release it may induce anti-tumor immunity (Zheng et al. 6731-35). HSP90-based vaccines have been shown to immunize against cancer and infectious diseases in both prophylactic and therapeutic protocols (reviewed in (Bolhassani and Rafati 1185-99; Castelli et al. 227-33; Murshid, Gong, and Calderwood 1019-30)).

However, HSP90 can also be considered as target for tumor therapy as 1) it correlates with tumor progression and leads to resistance towards apoptosis, also upon irradiation or chemotherapy treatment, and 2) it is overexpressed in many tumors including GC, osteosarcoma (Guo et al. 62-67), breast carcinoma (Hodorova et al. 31-35). Overexpression of HSP90 is associated with aggressive behavior and poor prognosis in GC (Wang, Wang, and Ying 35-41; Zheng et al. 1042-49). Downregulation of HSP90 in GC leads to apoptosis of cancer cells (Sheu, Liu, and Lan e1096).

Muc 6

MUC6 is expressed in mucous cells. Its primary function is thought to be the protection of vulnerable epithelial surfaces from damaging effects of constant exposure to a wide range of endogenous caustic or proteolytic agents (Toribara et al., 1997). MUC6 may also play a role in epithelial organogenesis (Reid and Harris, 1999). MUC6 expression is found in normal gastric mucosa. It is overexpressed in some cancers like intestinal adenoma and carcinoma, pulmonary carcinoma (Hamamoto et al. 891-96), colorectal polyps (Bartman et al. 210-18), and breast carcinoma (Pereira et al. 210-13), whereas it is not expressed in the respective normal tissues. The high expression rate of MUC6 in mucinous carcinoma suggests was suggested to act as a barrier to cancerous extension resulting in their less aggressive biological behaviour (Matsukita et al. 26-36). MUC6 expression was lower in gastric carcinomas than in adenomas or normal mucosa and inversely correlated with tumor size, depth of invasion, lymphatic and venous invasion, lymph node metastasis and UICC staging. Downregulation of MUC6 may contribute to malignant transformation of gastric epithelial cells and underlie the molecular bases of growth, invasion, metastasis and differentiation of gastric carcinoma (Zheng et al. 817-23). There is also evidence that *Helicobacter pylori* infection, one of the major causes of gastric carcinoma, is associated with reduced MUC6 expression (Kang et al. 29-35; Wang and Fang 425-31).

Kinetochore Protein Nuf2

NUF2 (CDCA-1) gene encodes a protein that is highly similar to yeast Nuf2, a component of a conserved protein complex associated with the centromere. Yeast Nuf2 disappears from the centromere during meiotic prophase when centromeres lose their connection to the spindle pole body, and plays a regulatory role in chromosome segregation. It was shown that survivin and hNuf2 csiRNAs temporally knockdown their mRNAs causing multinucleation and cell death by mitotic arrest, respectively (Nguyen et al. 394-403). Nuf2 and Hec1 are required for organization of stable microtubule plus-end binding sites in the outer plate that are needed for the sustained poleward forces required for biorientation at kinetochores (DeLuca et al. 519-31).

Nuf2 protein was found to be over-expressed in NSCLC, associated with poor prognosis (Hayama et al. 10339-48), and in cervical cancer (Martin et al. 333-59). In surgically resected gastric cancer tissues (diffuse type, 6; intestinal type, 4), 2 variants of NUF2 were upregulated. The alternative splicing variants detected in this study were suggested be potentially useful as diagnostic markers and/or novel targets for anticancer therapy (Ohnuma et al. 57-68).

siRNA-mediated knockdown against NUF2 has been found to inhibit cell proliferation and induction of apoptosis in NSCLC, ovarian cancer, cervical cancer, gastric cancer, colorectal cancer and glioma (Kaneko et al. 1235-40).

Lipid Phosphate Phosphohydrolase 2 (PPAP2C)

Phosphatidic acid phosphatases (PAPs) convert phosphatidic acid to diacylglycerol, and function in de novo synthesis of glycerolipids as well as in receptor-activated signal transduction mediated by phospholipase D. Three alternatively spliced transcript variants encoding distinct isoforms have been reported. PPAP2C is up-regulated in transformed primary human adult mesenchymal stem cells (MSCs), and numerous human cancers. It might be required for increased cell proliferation. Overexpression of PPAP2C, but not a catalytically inactive mutant, caused premature S-phase entry, accompanied by premature cyclin A accumulation. Knockdown decreases cell proliferation by delaying entry into S phase (Flanagan et al. 249-60).

40S Ribosomal Protein S11 is a Protein (RPS11)

Ribosomes consist of a small 40S subunit and a large 60S subunit. Together these subunits are composed of 4 RNA species and approximately 80 structurally distinct proteins. The RPS11 gene encodes a ribosomal protein that is a component of the 40S subunit. RPS11 was among six genes found in a screen for fecal RNA-based markers for colorectal cancer diagnosis. It was specifically found in cancer-patient derived fecal colonocytes (Yajima et al. 1029-37).

E3 Ubiquitin-Protein Ligase Seven in Absentia Homolog 2 (SIAH2)

SIAH2 is a E3 ubiquitin ligase. Among its substrates are beta-catenin, TRAF2, and DCC (deleted in colorectal cancer) (Habelhah et al. 5756-65; Hu and Fearon 724-32; Nakayama, Qi, and Ronai 443-51). SIAH2 also leads to degradation of the nuclear protein repp86, resulting in abrogation of the mitotic arrest induced by overexpression of this protein (Szczepanowski et al. 485-90). SIAH2 has tumor- as well as metastasis-promoting properties via at least two pathways, reviewed in (Nakayama, Qi, and Ronai 443-51): First, it leads to ubiquitination and degradation of proteins in the hypoxia response pathway, which leads to enhanced transcriptional activity of hypoxia-inducible factors (HIFs) (Nakayama, Qi, and Ronai 443-51)(Calzado et al. 85-91). Second, it suppresses Sprouty2, a specific inhibitor of Ras/ERK signaling. SIAH2 activity is correlated with pancreatic tumor development likely through its positive effect on Ras signaling (Nakayama, Qi, and Ronai 443-51).

Although the role of SIAH2 in cancer is partly controversial, some reports showing association of low levels of SIAH2 with poorer prognosis or therapy response (Confalonieri et al. 2959-68) (Jansen et al. 263-71), others show a tumorigenic function (Frasor et al. 13153-57). SIAH2 inhibition has been considered as anti-cancer treatment, as it has been shown to inhibit growth of xenografts in melanoma mouse models (Qi et al. 16713-18; Shah et al. 799-808), and of human lung cancer cell lines engrafted into nude mice (Ahmed et al. 1606-29).

Sodium- and Chloride-Dependent Taurine Transporter (SLC6A6)

SLC6A6 is a sodium- and chloride-dependent taurine transporter (TauT) (Han et al., 2006). Taurine transporter knockout (taut–/–) mice suffer from chronic liver disease due to taurine deficiency, which may involve mitochondrial dysfunction (Warskulat et al., 2006). Expression of SLC6A6 is repressed by the p53 tumour suppressor gene and is transactivated by proto-oncogenes such as WT1, c-Jun, and c-Myb. Over-expression of SLC6A6 protects renal cells from cisplatin-induced nephrotoxicity (Han et al., 2006; Han and Chesney, 2009). SLC6A6 mRNA expression was upregulated by tumor necrosis factor alpha (TNF-alpha) in human intestinal epithelial Caco-2 cells (Mochizuki et al., 2005).

Ubiquinol-Cytochrome c Reductase Binding Protein (UQCRB)

The protein encoded by the UQCRB-gene is part of the ubiquinol-cytochrome c oxidoreductase complex. It binds ubiquinone and participates in the transfer of electrons. Mutations in this gene are associated with mitochondrial complex III deficiency. A pseudogene has been described on the X chromosome.

The UQCRB-gene may be a potential oncogen or a tumour suppressor gene in pancreatic ductal adenocarcinoma (Harada et al. 13-24). It was found to be overexpressed in hepatocellular carcinoma (Jia et al. 1133-39)

Human Epidermal Growth Factor Receptor 3 (ERBB3)

ERBB3 encodes a member of the epidermal growth factor receptor (EGFR) family of receptor tyrosine kinases. It is activated by neuregulins, by other ERBB and nonERBB receptors as well as by other kinases, and by novel mechanisms. Downstream it interacts prominently with the phosphoinositol 3-kinase/AKT survival/mitogenic pathway, but also with GRB, SHC, SRC, ABL, rasGAP, SYK and the transcription regulator EBP1 (Sithanandam and Anderson 413-48). ERBB3 overexpression has been found in many cancers including gastric cancer, where it may play a key causative role and negatively impacts prognosis (Kobayashi et al. 1294-301) (Slesak et al. 2727-32). (Zhang et al. 2112-18) found that over-expression of ERBB3 was more frequent in the diffuse type (26.2%) of gastric cancer than in the intestinal type (5.0%). In both types, overexpression was associated with poor prognosis. Approaches for targeting of ERBB3 in cancer therapy include RNA aptamers to the extracellular domain (Chen et al. 9226-31), blockade of its gene expression by synthetic transcription factors (Lund et al. 9082-91), small-molecule inhibitors like the vitamin E isomer γ-tocotrienol (Samant and Sylvester 563-74), miRNA (Scott et al. 1479-86) and siRNA (Sithanandam et al. 1847-59).

Prominin 1 (Prom1)

Function: Prominin-1, also called CD133, was identified as a molecule specific for CD34+ hematopoetic progenitor cells (Yin et al., 1997) and shown to be a marker for normal stem cells and cancer stem cells (CSCs) of various tissues. It is located mainly in plasma membrane protrusions, and might be involved in the organization of membrane topology or in maintaining the lipid composition of the plasma membrane. It was suggested that a splice isoform of prominin-1 called AC133-2 and lacking a small exon of 27 amino acids may represent an even better stem cell marker (Mizrak et al., 2008; Bidlingmaier et al., 2008).

Only a small percentage of tumor cells is usually positive for prominin-1, as expected for a CSC marker. Depending on the tumor type, the number of positive cells per tumor mass reaches from 1 to 15% and is mostly around 2%.

Prominin-1 has been associated with tumor formation, angiogenesis and chemoresistance (Zhu et al., 2009a) (Bruno et al., 2006; Hilbe et al., 2004) (Bertolini et al., 2009). However, prominin-1 positive cells might be accessible by the immune system, as they can be killed by NK cells (Castriconi et al., 2007; Pietra et al., 2009) and cytotoxic T cells (Brown et al., 2009).

While for many cancer entities it has been shown that prominin-1 positive cells are functionally CSCs, and expression was frequently associated with poor prognosis, there are still controversies. Some reports state that it is neither necessary nor sufficient for identifying CSCs (Cheng et al., 2009; Wu and Wu, 2009). Possibly a combination of prominin-1 with other molecules such as CD44, or even multiple combinations such as prom1(+), CD34(+), CD44(+), CD38(−), CD24(−) serve as better CSC markers (Zhu et al., 2009b; Fulda and Pervaiz, 2010)

In diffuse GC, PROM1 expression was suggested based on an in silico analysis (Katoh and Katoh, 2007) and overexpression in GC compared to normal stomach tissue at the protein level was reported by (Smith et al., 2008). However, (Boegl and Prinz, 2009) reported that prominin-1 expression was reduced in GC, especially in later stages, and claimed that prominin-1 expression rather correlates with angiogenesis—which is also reduced in later stages—than with tumor growth. A study using GC cell lines (Takaishi et al., 2009) claims that CD44, but not prominin-1 is a CSC marker in GC.

Matrix Metalloproteinase 11 (MMP11)

Like other MMPs, MMP11 is an endopeptidase with functions in processes requiring tissue remodeling, such as development, wound healing and scar formation. It might also negatively regulate fat homeostasis by reducing adipocyte differentiation. In contrast to other MMPs, it is not able to cleave typical extracellular matrix molecules—except collagen VI. However, other substrates have been identified such as alpha 2-macroglobulin, certain serine protease inhibitors (serpins) including alpha 1 anti-trypsin, insulin-like growth factor-binding protein-1 and the laminin receptor. In cancer, MMP11 is mostly expressed in stromal cells surrounding tumor tissue. This has been shown for numerous tumor entities. It was stated that MMP11 is overexpressed in the stroma of most invasive human carcinomas, but rarely in sarcomas and other nonepithelial tumors. In most but not all cases, MMP11 is expressed in stroma cells directly adjacent to the tumor, whereas the tumor cells themselves, normal tissues and stroma cells distant from the tumor are negative. Higher levels of MMP11 are correlated with a malignant phenotype/higher invasiveness and bad prognosis. However, in papillary thyroid carcinomas, MMP11 expression was inversely linked to aggressive characteristics. MMP11 was found in tumor tissue as well as in serum of gastric cancer patients, and expression correlated with metastasis (Yang et al.). Moreover, (Deng et al. 274-81) showed that MMP11 is highly expressed in tumor cell lines and primary tumor of gastric cancer—in contrast to other cancer types not exclusively in the stroma—and that it appears to enhance tumor cell proliferation.

Nuclear Transcription Factor Y Subunit Beta (NFYB)

NFYB, also called CBF-B or CBF-A is, besides NFYA and NFYC, a part of the heterotrimeric basal transcription factor NF-Y (also CCAAT-binding factor or CBF) that binds to CCAAT motifs—or the reverse motifs, ATTGG, called Y-box—in the promoters and enhancers of numerous genes. Among the NF-Y target genes are MHC class II genes, the PDGF beta-receptor, several heat shock proteins, the mismatch repair gene hMLH1, and topoisomerase II alpha.

NFYB is not a classical oncogene, however its function might contribute to tumorigenesis. First, many cell-cycle genes such as cyclin A, cyclin B1, Aurora A and cdk1 are targets of NF-Y. Cells are arrested at G2/M phase without functional NFYB. (Park et al.) show that upregulation of cyclin B2 and other cell-cycle related genes in colorectal adenocarcinoma are due to NF-Y activity. Second, NF-Y activity counteracts apoptosis. Cells lacking NF-Y undergo apoptosis due to p53 activation and reduced transcription of anti-apoptotic genes containing CCAAT-boxes in their promoters, such as Bcl-2 (Benatti et al. 1415-28). Third, its tumorigenic properties are enhanced in combination with other transcription factors. For example, mutated p53 binds to NF-Y and p300 proteins, increasing the expression of NF-Y-induced cell cycle genes.

ABL1

The protein tyrosine kinase c-Abl shuttles between the nuclear and cytoplasmic compartments. Nuclear c-Abl is involved in cell growth inhibition and apoptosis, while cytoplasmic c-Abl may play a role in actin dynamics, morphogenesis and signaling induced by extracellular stimuli like growth factors and integrin ligands. Cytoplasmic c-Abl was reported to promote mitogenesis. Activity of c-Abl protein is negatively regulated by its SH3 domain, and deletion of the SH3 domain turns ABL1 into an oncogene. In chronic myeloic leukemia (CML), the gene is activated by translocation within the BCR (breakpoint cluster region) gene on chromosome 22. This resulting fusion protein BCR-ABL locates to the cytosol and allows the cells to proliferate without being regulated by cytokines (Zhao et al.). c-Abl activity is also upregulated in solid tumors, as it was shown for breast carcinomas and NSCLC. Overexpression is not sufficient and constitutive kinase activity required protein phosphorylation. In breast cancer cells, c-Abl phosphorylation is induced by plasma membrane tyrosine kinases, including SFK, EGFR family members and the IGF-1 receptor. ABL fusion proteins have not been detected in solid tumors (Lin and Arlinghaus, 2008). ABL was shown to be espressed in gastric carcinoma and associated microvessels, suggesting a possible role in angiogenesis. Notably, H. pylori cytotoxin-associated gene A (CagA) leads to activation of c-Abl, which, consequently phosphorylates EGFR and, thus, blocks EGFR endocytosis (Bauer, Bartfeld, and Meyer 156-69). Several tyrosine kinase inhibitors are more or less specific for Abl. Imatinib (Gleevec) is used as a first line therapy for CML and has also been approved for patients with advanced gastrointestinal stromal tumors (GIST), as it also targets KIT (Pytel et al. 66-76) (Croom and Perry, 2003). Other inhibitors used for cancer therapy are Dasatinib and Nilotinib (Pytel et al. 66-76) (Deremer, Ustun, and Natarajan 1956-75).

Polo-Like Kinase 4 (Plk4)

Polo kinase family members (Plk1-4) are important during cell division, regulating several steps during mitosis. Plk4 is an organizer of centriole formation and duplication (Rodrigues-Martins et al. 1046-50). While Plk1 is a clear oncogene, Plk4's function in cancer is ambiguous. Downregulation as well as overexpression of Plk4 has been associated with cancer in humans, mice and flies (Cunha-Ferreira et al. 43-49). For instance, in colorectal cancer, Plk4 was found overexpressed, but a small group of patients showed strong Plk4 downregulation (Macmillan et al. 729-40). This can be explained by the fact that both overexpression and deficiency of Plk4 lead to aberrant centriole formation, resulting in abnormal centrosome numbers and structures that are frequently detected in tumor cells and contribute to mitotic aberrations that cause chromosome missegregation and aneuploidy (Peel et al. 834-43). (Kuriyama et al. 2014-23). (Korzeniewski et al. 6668-75).

IQ Motif Containing GTPase Activating Protein 3 (IQGAP3)

IQGAPs participate in cellular signaling pathways as well as cytoskeletal architecture and cell adhesion. They possess a domain with sequence similarity to RasGAPs and, correspondingly, bind to small GTPases. However (and despite their name), none of them has GTPase-activating activity. For IQGAP1 and IQGAP2 it has been shown that they even stabilize the GTP-bound state of Rac1 and Cdc42, and IQGAP3 was suggested to stabilize activated Ras (Nojima et al. 971-78; White, Brown, and Sacks 1817-24). Via their IQ-domain they bind to calcium/calmodulin, and via a calponin homology domain to actin filaments (White, Brown, and Sacks 1817-24). (Wang et al. 567-77) report that IQGAP3 is expressed in brain, where it associates with actin filaments as well as Rac1 and Cdc42. It accumulates at the distal region of axons and promotes Rac1/Ccd42-dependent axon outgrowth. The IQGAPs have been implicated in cancer. IQGAP1 is considered to be an oncogene. It enhances several cancer-related pathways like MAP kinase, beta-catenin and VEGF-mediated signaling and is overexpressed in many tumors. IQGAP2 rather seems to function as tumor suppressor and was found reduced in gastric cancers with poor prognosis (White, Brown, and Sacks 1817-24). Little information is available about IQGAP3. (Skawran et al. 505-16) found it to be among the genes significantly upregulated in hepatocellular carcinoma. Two studies report that IQGAP3 is specifically expressed in proliferating (Ki67+) cells in mouse small intestine, colon and liver (Nojima et al. 971-78) (Kunimoto et al. 621-31).

Coiled-Coil Domain Containing 88a (CCDC88A)

CCDC88A is an actin-binding Akt substrate that plays a role in actin organization and Akt-dependent cell motility in fibroblasts. The CCDC88A/Akt pathway is also essential in VEGF-mediated postneonatal angiogenesis.

CCDC88A is also highly expressed in a variety of human malignant tissues, including breast, colon, lung, and uterine cervical carcinomas. It plays an important role in tumor progression with aberrant activation of the Akt signaling pathway.

Cyclin B1 (CCNB1)

CCNB1 is induced during G2/M phase of mitosis and forms the mitosis-promoting factor (MPF) together with cyclin-dependent kinase 1 (Cdk1)/Cdc2. Overexpression is found in a variety of cancers and is often associated with poor prognosis, e.g. in breast cancer (Aaltonen et al., 2009; Agarwal et al., 2009; Suzuki et al., 2007), medulloblastoma (de et al., 2008), NSCLC (Cooper et al., 2009), cervical cancer (Zhao et al., 2006), and others. It was one of the genes included in an 11-gene signature that was found to predict short interval to disease recurrence in patients with 12 distinct types of cancer (Glinsky, 2006). No specific information on gastric cancer was found.

Cyclin D2 (CCND2)

CCND2 binds and activates, like other D-type cyclins (D1 and D3), cyclin-dependent kinase 4 (Cdk4) or Cdk6. This is required for G1/S transition. CCND2 was found to be overexpressed in many tumors, including testicular and ovarian tumors (Sicinski et al., 1996), hematological malignancies (Hoglund et al., 1996; Gesk et al., 2006), and gastric cancer, where it may be caused by *H. pylori* infection, and associated with poor prognosis (Yu et al., 2003). (Yu et al., 2001) (Oshimo et al., 2003) (Takano et al., 1999) (Takano et al., 2000).

Cyclin E2 (CCNE2)

CCNE2 binds and activates, like the other E-type cyclin CCNE1, Cdk2. This activity peaks at G1/S phase transition. Under healthy conditions, CCNE2 is not detectable in quiescent cells and can only be found in actively dividing tissues (Payton and Coats, 2002). It is often aberrantly expressed in cancer, e.g. in breast cancer, correlated to bad prognosis (Desmedt et al., 2006; Ghayad et al., 2009; Payton et al., 2002; Sieuwerts et al., 2006), and in metastatic prostate cancer (Wu et al., 2009).

Carcinoembryogenic antigen-related cell adhesion molecules 1, 5 and 6 (CEACAM 1, 5, and 6) CEACAMs are membrane-anchored glycoproteins that mediate cell-cell interactions and activate integrin signaling pathways (Chan and Stanners, 2007). They may also serve as receptors for pathogens such as *E. coli* (Berger et al., 2004) (Hauck et al., 2006) and be involved in immune regulation (Shao et al., 2006).

CEACAM5 and CEACAM6 have pro-cancerogenic functions. They inhibit anoikis (Ordonez et al., 2000), promote metastasis (Marshall, 2003; Ordonez et al., 2000), and disrupt cell polarization and tissue architecture (Chan and Stanners, 2007). The role of CEACAM1 in cancer is ambiguous. It may be a tumor suppressor in early stages, and contribute to metastasis formation, tumor immune escape and angiogenesis in later phases (Hokari et al., 2007; Liu et al., 2007; Moh and Shen, 2009). Its functional role depends on the isoform, as CEACAM1 occurs in 11 splice variants, whose ratio determines the signaling outcome (Gray-Owen and Blumberg, 2006; Leung et al., 2006; Neumaier et al., 1993; Nittka et al., 2008). The ratio of the splice variants may be altered in cancer (Gaur et al., 2008).

CEACAM5 or CEACAM6 or both are overexpressed in as many as 70% of all human tumors, often associated with poor prognosis (Chan and Stanners, 2007; Chevinsky, 1991). Serum CEACAM5 is an established clinical marker for colon and rectal carcinoma, high levels indicating poor prognosis or recurrence (Chevinsky, 1991; Goldstein and Mitchell, 2005). It was also suggested as a marker for other entities including gastric cancer, however with limited prognostic power (Victorzon et al., 1995). CEACAM1 can be up- or downregulated in cancer, depending on the entitiy (Kinugasa et al., 1998) (Dango et al., 2008) (Simeone et al., 2007). (Han et al., 2008) found abundant levels of CEACAM5 and CEACAM6 in nine gastric cancer cell lines, while CEACAM1 was undetectable. By contrast, an analysis of primary tumor samples from 222 patients showed either cytoplasmic or membranous staining for CEACAM1. The membrane-bound form was related to enhanced angiogenesis (Zhou et al., 2009). Also the study by (Kinugasa et al., 1998) showed an upregulation in gastric adenocarcinomas.

In some tumors, CEACAM1 is downregulated in tumor cells, which leads to upregulation of VEGF, and VEGF or hypoxic conditions may induce CEACAM1 in the adjacent endothelium. Accordingly, a monoclonal antibody against CEACAM1 blocked VEGF-induced endothelial tube formation (Oliveira-Ferrer et al., 2004; Tilki et al., 2006; Ergun et al., 2000).

Especially CEACAM5 has been tested as target for anti-cancer drugs, amongst others by vaccination approaches. These studies showed that CEACAM5 can be a target of cellular immune reactions (Cloosen et al., 2007; Marshall, 2003). An overview about CEACAM5 T cell epitopes is provided in (Sarobe et al., 2004).

Chloride Channel 3 (CLCN3)

CLCN3 is a Cl— channel that may be volume-gated and contribute to the regulatory volume decrease (RVD) that occurs as reaction to an increase in cell volume in case of conditions like cell cycling or hypoosmosis (Lemonnier et al., 2004; Sardini et al., 2003). However, this point is controversially discussed (Wang et al., 2004) and the volume-reducing channel activated during apoptosis is different from CLCN3 (Okada et al., 2006).

CLCN3 expression changes during cell cycle, peaking in S phase (Wang et al., 2004). CLCN3 currents may be important in cancer-relevant processes in entities where CLCN3 is upregulated, such as glioma: Tumor cells need to handle proliferative volume increases, encounter hypoosmotic conditions, e.g. in peritumoral edema (Ernest et al., 2005; Olsen et al., 2003; Sontheimer, 2008).

Moreover, it was reported that CLCN3 enhances etoposide resistance by increasing acidification of the late endocytic compartment (Weylandt et al., 2007).

siRNA-mediated knockdown of CLCN3 reduced the migration of nasopharyngeal carcinoma cells in vitro (Mao et al., 2008).

DNAJC10

DNAJC10 is a member of a supramolecular ER-associated degradation (ERAD) complex that recognizes and unfolds misfolded proteins for their efficient retrotranslocation (Ushioda et al., 2008). The protein was shown to be elevated in hepatocellular carcinoma (Cunnea et al., 2007). Knockdown of DNAJC10 by siRNA in neuroectodermal tumour cells increased the apoptotic response to the chemotherapeutic drug fenretinide (Corazzari et al., 2007). It was shown that ERdj5 decreases neuroblastoma cell survival by down-regulating the unfolded protein response (UPR) (Thomas and Spyrou, 2009).

Eukaryotic Translation Initiation Factor 2, Subunit 3 Gamma (EIF2S3)

EIF2S3 is the largest subunit of a protein complex (EIF2) recruiting the initial methionyl-tRNA to the 40S ribosomal subunit (Clemens, 1997). The action of kinases that downregulate EIF activity, such as RNA-dependent protein kinase (PKR), may be proapoptotic and tumor-suppressing (Mounir et al., 2009). In gastric cancer, higher levels of phosphorylated and unphosphorylated EIF2 were reported, and a redistribution to the nucleus was observed. This deregulation points towards an implication of eIF2alpha in gastrointestinal cancer (Lobo et al., 2000).

Eukaryotic Translation Initiation Factor 3 Subunit L (EIF3L)

EIF3L is one of 10-13 subunits of EIF3, which is associated with the small ribosomal subunit. EIF3 plays a role in prevention of premature binding of the large ribosomal subunit. EIF3L is among the five subunits that have been reported to not be essential for EIF3 formation (Masutani et al., 2007). A screen with an antisense-library suggested that downregulating EIF3L enhances the anti-tumorigenic activity of 5-fluorouracil in hepatocellular carcinoma cells (Doh, 2008).

Epiplakin1 (EPPK1)

EPPK1 is a plakin family gene with largely unknown functions. The plakin genes are known to function in interconnecting cytoskeletal filaments and anchoring them at plasma membrane-associated adhesive junction (Yoshida et al., 2008).

G-Protein Coupled Receptor 39 (GPR39)

GPR39 is a Gq protein-coupled receptor that is thought to be involved in gastrointestinal and metabolic function (Yamamoto et al., 2009). Its signalling activates cAMP and serum response elements (Hoist et al., 2004). The endogenous ligand for GPR39 is probably zinc (Chen and Zhao, 2007). GPR39 is a novel inhibitor of cell death, which might represent a therapeutic target with implications for processes involving apoptosis and endoplasmic reticulum stress like cancer (Dittmer et al., 2008). GPR39 was found to be up-regulated in microarrays of both human fetal kidney HFK and blastema-enriched stem-like wilms' tumor xenografts (Metsuyanim et al., 2009), and in a hippocampal cell line resistant against diverse stimulators of cell death (Dittmer et al., 2008).

ERBB2/HER2/NEU

ERBB2 is a member of the EGFR family of receptor tyrosine kinases. Its ligand is not known, but it is the preferred heterodimerization partner for other members of the HER family (Olayioye, 2001). In carcinomas, HER2 acts as an oncogene, mainly because high-level amplification of the gene induces protein overexpression in the cellular membrane and subsequent acquisition of advantageous properties for a malignant cell (Slamon et al., 1989). Overexpression is observed in a certain percentage of many cancers, including gastric cancer. Mostly, it is associated with bad prognosis (Song et al., 2010) (Yonemura et al., 1991) (Uchino et al., 1993) (Mizutani et al., 1993).

ERBB2 is the target of the monoclonal antibody trastuzumab (marketed as Herceptin), which has been suggested as treatment option for patients with HER2-positive advanced gastric cancer, in combination with chemotherapy (Meza-Junco et al., 2009; Van Cutsem et al., 2009). Another monoclonal antibody, Pertuzumab, which inhibits dimerization of HER2 and HER3 receptors, is in advanced clinical trials (Kristjansdottir and Dizon, 2010). The selective overexpression of HER2 and HER3 in the two histologic types of gastric cancer (intestinal type and diffuse type) is strongly associated with a poor prognosis (Zhang et al., 2009).

Beta-4 Integrin (ITGB4)

Integrins mediate cell adhesion as well as outside-in and inside-out signal transduction. The integrin beta-4 subunit heterodimerizes with the alpha-6 subunit. The resulting integrin promotes the formation of hemidesmosomes between the intracellular keratin cytoskeleton and the basement membrane (Giancotti, 2007). Integrin beta-4 has a dual function in cancer, as it can mediate stable adhesion on the one hand, and pro-invasive signalling (including Ras/Erk and PI3K signalling) and angiogenesis on the other hand (Giancotti, 2007; Raymond et al., 2007). It is overexpressed in many tumors as well as in angiogenic endothelial cells, often correlating with progression and metastasis. High levels have been in gastric cancer, particularly in stroma-invading cells (Giancotti, 2007; Tani et al., 1996). However, it was downregulated in undifferentiated-type gastric carcinoma as the tumor invaded deeper, possibly du to the gradual epithelial-mesenchymal transition, as beta-4 integrin is an epithelial integrin (Yanchenko et al., 2009).

Lipocalin (LCN2)

LCN2 or neutrophil gelatinase-associated lipocalin (NGAL) is an iron regulatory protein that exists as a monomer, homodimer, or as a disulfide-linked heterodimer with MMP9 (Coles et al., 1999; Kjeldsen et al., 1993). Expression is increased in several cancers, in some cases associated with progression. Mechanistically, it may stabilize MMP9 and alter E-cadherin-mediated cell-cell adhesion, thereby increasing invasion. Complexes of MMP-9 and LCN2 were related with worse survival in gastric cancer (Kubben et al., 2007) (Hu et al., 2009). Although a clear pro-tumoral effect has been observed in various tumors in humans, some studies have demonstrated that LCN2 can inhibit the pro-neoplastic factor HIF-1alpha, FA-Kinase phosphorylation and also VEGF synthesis, thus suggesting that, in alternative conditions, LCN2 also, paradoxically, has an anti-tumoral and anti-metastatic effect in neoplasias of, for example, the colon, ovary and pancreas. (Bolignano et al., 2009; Tong et al., 2008). LCN2 may be useful for inhibiting tumor angiogenesis, in addition to suppressing tumor metastasis, in cancers which show ras activation (Venkatesha et al., 2006).

Succinate Dehydrogenase Complex, Subunit C (SDHC)

SDHC is one of four nuclear-encoded subunits of succinate dehydrogenase (mitochondrial complex II), which transfers electrons from succinate to ubiquinone, yielding fumarate and ubiquinol. Succinate dehydrogenase deficiency may cause GISTs (McWhinney et al., 2007). Familial gastrointestinal stromal tumors may be caused by mutations in the subunit genes SDHB, SDHC, and SDHD, and abdominal paragangliomas associated with gastrointestinal tumors may be caused uniquely by SDHC mutations (Pasini et al., 2008). Mutant SDHC protein in transgenic mice generates oxidative stress and can contribute to nuclear DNA damage, mutagenesis, and ultimately, tumorigenesis (Ishii et al., 2005). Succinate dehydrogenase is considered a tumor suppressor (Baysal, 2003; Gottlieb and Tomlinson, 2005). Decreased levels of this enzyme complex may result in tumorigenesis (Eng et al., 2003).

PDZ-Binding Kinase (PBK)

PBK is a MEK3/6-related MAPKK which activates p38 MAP kinase, e.g. downstream of growth factor receptors (Abe et al., 2000; Ayllon and O'connor, 2007). JNK may be a secondary target (Oh et al., 2007). As in adults PBK is expressed in testis (see below), a function in spermatogenesis has been proposed (Abe et al., 2000; Zhao et al., 2001). Apart from that, it contributes to proliferation and apoptosis resistance in tumor cells: It is phosphorylated and activated during mitosis, which is necessary for spindle formation and cytokinesis (Gaudet et al., 2000; Matsumoto et al., 2004; Park et al., 2009) (Abe et al., 2007). Other growth-promoting and anti-apoptotic functions include downregulation of p53 and histone phosphorylation (Park et al., 2006; Zykova et al., 2006) (Nandi et al., 2007). PBK has been classified as cancer-testis antigen (Abe et al., 2000; Park et al., 2006) and was found to be overexpressed in many cancers.

Polymerase (DNA-Directed), Delta 3, Accessory Subunit (POLD3)

The DNA polymerase delta complex is involved in DNA replication and repair. It consists of the proliferating cell nuclear antigen (PCNA), the multisubunit replication factor C, and the 4 subunit polymerase complex: POLD1, POLD2, POLD3, and POLD4 (Liu and Warbrick, 2006). POLD3 plays a crucial role in the efficient recycling of PCNA during dissociation-association cycles of pol delta during elongation phase of DNA replication (Masuda et al., 2007).

Proteasome (Prosome, Macropain) 26S Subunit, Non-ATPase, 14 (PSMD14)

PSMD14 is a component of the 26S proteasome. It belongs to the 19S complex (19S cap; PA700), which is responsible for substrate deubiquitination during proteasomal degradation (Spataro et al., 1997). PSMD14 overexpression in mammalian cells affects cell proliferation and the response to cytotoxic drugs like vinblastine, cisplatin and doxorubicin (Spataro et al., 2002). siRNA suppression of PSMD14 in HeLa cells resulted in a reduction in cell viability and an increase in polyubiquitinated protein levels (Gallery et al., 2007). Down-regulation of PSMD14 by siRNA had a considerable impact on cell viability causing cell arrest in the G0-G1 phase, ultimately leading to senescence (Byrne et al., 2010).

Proteasome (Prosome, Macropain) 26S Subunit, ATPase, 2 (PSMC2)

PSMC2 is part of the 26S proteasome system. It is a member of the triple-A family of ATPases, which have a chaperone-like activity. This subunit has been shown to interact with several of the basal transcription factors so, in addition to participation in proteasome functions, this subunit may participate in the regulation of transcription. It was shown that the 26S proteasome system in skeletal muscle can be activated by TNF-alpha (Tan et al., 2006). In HBx transgenic mice, which bear the Hepatitis B regulatory gene HBx in their germline, and develop HCC, PSMC2 and other proteasome subunits are up-regulated in tumor tissues (Cui et al., 2006). The mRNA levels for the ATPase subunit PSMC2 of the 19S complex increased in cancer cachexia (Combaret et al., 1999).

Protein Tyrosine Kinase 2 (PTK2)

PTK2 is a non-receptor tyrosine kinase which modulates integrin signalling and may promote tumor growth, progression and metastasis ((Giaginis et al., 2009); (Hauck et al., 2002); (Zhao and Guan, 2009)). PTK2 was suggested to be a marker for carcinogenesis and the progression of cancer (Su et al., 2002; Theocharis et al., 2009; Jan et al., 2009). Overexpression and/or increased activity occurs in a wide variety of human cancers including gastric cancer. PTK2 also transduces signals downstream of the gastrin receptor, which contributes to proliferation of gastric cancer cells (Li et al., 2008b). 8% of gastric carcinomas have been shown to carry the Epstein-Barr virus (EBV). EBV-infected human gastric cancer cell line sublines presented increased PTK2 phosphorylation (Kassis et al., 2002). The level of PTK2 tyrosine phosphorylation in gastric epithelial cells is reduced by the cagA-positive *Helicobacter pylori* product.

Tetraspanin 1 (TSPAN1) and Tetraspanin 8 (TSPAN8)

TSPAN1 and TSPAN8 belong to the family of tetraspanins which are characterized by four transmembrane-domains and an intracellular N- and C-terminus and which have roles in a variety of processes including cellular adhesion, motility, activation and tumor invasion. They often form large molecular complexes with other proteins such as integrins at the cell surface (Tarrant et al., 2003; Serru et al., 2000). The functions of TSPAN1 are yet unknown and may include a role in secretion (Scholz et al., 2009). TSPAN1 is overexpressed in several cancers, often correlating with stage, progression and worse clinical outcome. Notably, it was reported to be overexpressed in 56.98% of 86 cases of gastric carcinoma, and overexpression correlated positively with clinical stage, infiltration and lymph node status and negatively with survival rates and differentiation grade of the tumor (Chen et al., 2008). TSPAN8 has been reported as a metastasis-associated gene in many types of tumors (PMID: 16467180). In gastrointestinal cancer, TSPAN8 expression is associated with poor prognosis (PMID: 16849554).

Zinc Finger Protein 598 (ZNF598)

ZNF598 is a zinc finger protein with yet unknown function.

A Disintegrin and Metalloproteinase 10 (ADAM10)

ADAM10 plays a role in angiogenesis, development and tumorigenesis. It is overexpressed in gastric carcinoma. Selective ADAM inhibitors against ADAM-10 are undergoing clinical trials for the treatment of cancer. (PMID: 19408347)

Matrix Metalloproteinase 12 (MMP12)

MMP12 is a zinc endopeptidase which degrades elastin and many other matrix- and non-matrix-proteins and is involved in macrophage migration and inhibition of angiogenesis (Chakraborti et al., 2003; Chandler et al., 1996; Sang, 1998). It also plays a role in pathological processes of tissue destruction like asthma, emphysema and chronic obstructive pulmonary disease (COPD), rheumatoid arthritis and tumor growth (Cataldo et al., 2003; Wallace et al., 2008). MMP12 inhibitors are discussed as agents for treatment of these conditions (Churg et al., 2007; Norman, 2009). MMP12 is frequently over-expressed in cancer, where it may have ambiguous functions. While it may be involved in matrix dissolution and, thus, metastasis, it can also inhibit tumor growth through production of angiostatin, which negatively impacts angiogenesis. Enhanced MMP12 expression was reported for GC, and shown to be favorable: It negatively correlated with microvessel density, VEGF, tumor differentiation grade, vascular invasion, lymph node metastasis and recurrence. Patients with MMP12 over-expression demonstrated a significantly better survival rate (Cheng et al., 2010; Zhang et al., 2007b; Zhang et al., 2007a)

Ribonucleotide Reductase M2 (RRM2)

RRM2 is one of two subunits of ribonucleotide reductase, which generates deoxyribonucleotides from ribonucleotides. Overexpression of RRM2 has been observed in tumors including gastric cancer and enhances the metastatic potential (PMID: 18941749) (PMID: 19250552) siRNA knockdown of RRM2 slowed tumor growth in various species (mouse, rat, monkey) (PMID: 17929316; PMID: 17404105).

Transmembrane Protease, Serine 4 (TMPRSS4)

TMPRSS4 is a type II transmembrane serine protease found at the cell surface that is highly expressed in several cancer tissues, including pancreatic, colon and gastric cancer. The biological functions of TMPRSS4 in cancer are not yet known. TMPRSS4 has four splice variants (Scott et al., 2001; Sawasaki et al., 2004). Expression in ovarian carcinoma correlated with stage (Sawasaki et al., 2004). TMPRSS4 is highly elevated in lung cancer tissues, and siRNA knockdown of TMPRSS4 by small interfering RNA treatment in lung and colon cancer cell lines was associated with reduction of cell invasion and cell-matrix adhesion as well as modulation of cell proliferation (Jung et al., 2008).

Deiodinase, Iodothyronine, Type II (DIO2)

DIO2 converts the prohormone thyroxine (T4) to bioactive 3,3',5-triiodothyronine (T3). It is highly expressed in the thyroid, and expression and/or activity were found deregulated in cancers of the thyroid (de Souza Meyer et al., 2005) (Arnaldi et al., 2005). However, it was also found in other tissues, such as normal lung and lung cancer (Wawrzynska et al., 2003), and in brain tumors (Murakami et al., 2000).

Insulin-Like Growth Factor 2 mRNA Binding Protein 3 (IGF2BP3)

IGF2BP3 is primarily present in the nucleolus, where it binds IGF2 mRNA and represses its translation. It plays a role in embryogenesis and is downregulated in adult tissues.

In tumor cells it can be upregulated and is, thus, considered an oncofetal protein (Liao et al. 2005). In many cancers including gastric cancer it was found to be overexpressed, associated with poor prognosis (Jeng et al. 2009)(Jiang et al. 2006). Peptides derived from IGF2BP3 were tested in cancer vaccination studies (Kono et al. 2009).

Lamin B1 (LMNB1)

Lamin B1 is a protein of the nuclear lamina matrix and is involved in nuclear stability, chromatin structure and gene expression. In early stages of apoptosis, lamin is degraded (Neamati et al. 1995) (Sato et al. 2008b; Sato et al. 2008a; Sato et al. 2009). LMNB1 is expressed to some extent in essentially all normal somatic cells, and preliminary studies indicate that it may be reduced during the pathogenesis of some cancers including gastric cancer (Moss et al. 1999). In other cancers, such as hepatocellular carcinoma, LMNB1 was found upregulated and correlated positively with tumor stage, size and number of nodules (Lim et al. 2002).

Wingless-Type MMTV Integration Site Family, Member 5A

WNT5A is a secreted signaling protein implicated in developmental processes and oncogenesis. Canonical WNT5A signaling through Frizzled and LRP5/LRP6 receptors leads to maintenance of stem/progenitor cells, while non-canonical WNT5A signaling through Frizzled and ROR2/PTK/RYK receptors controls tissue polarity, cell adhesion or movement, e.g. at the tumor-stromal interface, leading to invasion (Katoh and Katoh, 2007). It may be a tumor suppressor in some cancers, but is upregulated in others including gastric cancer, where it contributes to progression and metastasis and leads to poor prognosis (Li et al., 2010) (Yamamoto et al., 2009) (Kurayoshi et al., 2006).

Fibroblast Activating Protein, Alpha (FAP)

FAP is an integral membrane gelatinase. Its putative serine protease activity may play a role in the control of fibroblast growth or epithelial-mesenchymal interactions during development, tissue repair and epithelial carcinogenesis (Scanlan et al. 1994). FAP has a potential role in cancer growth, metastasis and angiogenesis through cell adhesion and migration processes, as well as rapid degradation of ECM components. It is present on tumor cells invading the ECM, in reactive cancer-associated fibroblasts, and in endothelial cells involved in angiogenesis, but not in inactive cells of the same type. (Dolznig et al. 2005; Kennedy et al. 2009; Rettig et al. 1993; Rettig et al. 1994; Scanlan et al. 1994; Zhang et al. 2010). FAP expression has been found in gastric cancer cells and associated stromal fibroblasts (Zhi et al. 2010) (Chen et al. 2006)(Mori et al. 2004; Okada et al. 2003). In a mouse model, FAP-expressing cells where shown to be a nonredundant, immune-suppressive component of the tumor microenvironment (Kraman et al. 2010). In mouse models of tumor vaccination, FAP was successfully used as target for CD8+ and CD4+ T-cell responses (Loeffler et al. 2006; Wen et al. 2010)(Lee et al. 2005) (Fassnacht et al. 2005).

Coatomer Protein Complex, Subunit Gamma (COPG);
Coatomer Protein Complex, Subunit Gamma 2 (COPG2);
Coatomer Protein Complex, Subunit Beta 1 (COPB1)

COPG, COPG2 and COPB1 are subunits of the coatomer complex, also called coat protein complex 1 (COPI) that is associated with non-clathrin coated vesicles. COPI-coated vesicles mediate retrograde transport from the Golgi back to the ER and intra-Golgi transport (Watson et al., 2004). They may also be involved in anterograde transport (Nickel et al., 1998). The retrograde trafficking regulates, amongst others, EGF-dependent nuclear transport of EGFR, which binds to COPG (Wang et al., 2010). COPG was found to be overexpressed in lung cancer cells and lung cancer-assocated microvascular endothelial cells (Park et al., 2008).

The sequence of the ubiquitously expressed COPG2 is 80% identical to GOPG (Blagitko et al., 1999). COPG2 can form a COP I-like complex in place of GOPG, which is probably functionally redundant (Futatsumori et al., 2000).

Knockdown of COPB1 in a cystic fibrosis transmembrane conductance regulator (CFTR) expressing cell line suggested that the coatomer complex is involved in CRTR trafficking to the plasma membrane (Denning et al., 1992) (Bannykh et al., 2000).

Ubiquitin-Conjugating Enzyme E2S (UBE2S)

UBE2S is an auxiliary factor of the anaphase-promoting complex (APC), an E3 ubuiqitin ligase that regulates mitotic exit and G1 by targeting cell cycle regulators. UBE2S elongates ubiquitin chains after the substrates are pre-ubiquitinated by other components (Wu et al., 2010). UBE2S also targets the VHL protein for proteasomal degradation, thereby stabilizing HIF-1alpha (Lim et al., 2008), and possibly supporting proliferation, epithelial-mesenchymal transition, and metastasis (Chen et al., 2009) (Jung et al., 2006). UBE2S is overexpressed in several cancer entities.

Kinesin Family Member 11 (KIF11)

KIF11 is required for the assembly of a bipolar mitotic spindle. It has been found upregulated in several cancers, often correlating with clinicopathological parameters (Liu et al., 2010) (Peyre et al., 2010). Small molecule inhibitors of KIF11 like S-Trityl-L-cysteine (STLC), developed as potential anti-cancer drugs, arrest cells in mitosis and promote apoptosis of cancer cells (Tsui et al., 2009) (Wiltshire et al., 2010) (Ding et al., 2010). In the clinic, KIF11 inhibitors have shown only modest activity (Kaan et al., 2010; Tunquist et al., 2010; Wiltshire et al., 2010; Zhang and Xu, 2008).

A Disintegrin and Metalloprotease Domain 8 (ADAM8)

ADAM8 was initially considered to be an immune-specific ADAM, but was found also in other cell types, often under conditions involving inflammation and ECM remodelling, including cancers and respiratory diseases like asthma (Koller et al. 2009). Many ADAM species, including ADAM8, are expressed in human malignant tumors, where they are involved in the regulation of growth factor activities and integrin functions, leading to promotion of cell growth and invasion, although the precise mechanisms of these are not clear at the present time (Mochizuki and Okada 2007). In mouse gastric tumors, ADAM8 and other ADAMs were increased, probably due to enhanced EGFR signaling (Oshima et al. 2011).

Cell Division Cycle 6 Homolog (*S. Cerevisiae*) (CDC6)

CDC6 is essential for the initiation of DNA replication. It localizes in the nucleus during G1, but translocates to the cytoplasm at the start of S phase. CDC6 also regulates replication-checkpoint activation through interaction wih ATR (Yoshida et al. 2010). CDC6 deregulation may cause the inactivation of the INK4/ARF locus encoding three important tumor suppressor genes: p16INK4a and p15INK4b, both activators of the retinoblastoma pathway, and ARF, an activator of p53 (Gonzalez et al. 2006). siRNA knockdown of CDC6 could prevent proliferation and promote apoptosis (Lau et al. 2006). CDC6 is upregulated in cancers including gastric cancer (Nakamura et al. 2007) (Tsukamoto et al. 2008).

F2R Coagulation Factor II (Thrombin) Receptor (F2R)

F2R, also called proteinase activated receptor (PAR1) is a G-protein coupled receptor. Signals by PAR1, PAR2, and PAR4 can regulate calcium release or mitogen-activated protein kinase activation and lead to platelet aggregation, vascular relaxation, cell proliferation, cytokine release, and inflammation (Oikonomopoulou et al. 2010). F2R is thought to be involved in endothelial and tumor cell proliferation and angiogenesis, and is overexpressed in invasive and metastatic tumors of many types. The expression levels directly correlate with the degree of invasiveness of the cancer (Garcia-Lopez et al. 2010) (Lurje et al. 2010). In gastric carcinoma cells, F2R activation can trigger an array of responses that promote tumor cell growth and invasion, e.g. overexpression of NF-kappaB, EGFR, and Tenascin-C (TN-C) (Fujimoto et al. 2010). Accordingly, F2R expression in gastric cancer was found to be associated with the depth of wall invasion, peritoneal dissemination, and poor prognosis (Fujimoto et al. 2008). A mouse monoclonal anti-human PAR1 antibody (ATAP-2), that recognizes an epitope (SFLLRNPN) within the N-terminus of the thrombin receptor, was described as well as the PAR1 agonist peptide TFLLRNPNDK (Hollenberg and Compton 2002; Mari et al. 1996; Xu et al. 1995)

Olfactomedin 4 (OLFM4)

OLFM4, whose function is largely unknown, is overexpressed in inflamed colonic epithelium and a number of human tumor types, especially those of the digestive system (Koshida et al., 2007). OLFM4 is a robust marker for stem cells in human intestine and marks a subset of colorectal cancer cells (van der Flier et al., 2009). OLFM4 inhibits the apoptosis-promoting protein GRIM-19 (Zhang et al., 2004) (Huang et al., 2010), regulates cell cycle and promotes S phase transition in proliferation of cancer cells. In addition, OLFM4 is associated with cancer adhesion and metastasis (Yu et al., 2011b). Forced overexpression of OLFM4 in murine prostate tumor cells led to more rapid tumor formation in a syngeneic host (Zhang et al., 2004). OLFM4 was found to be overexpressed in GC (Aung et al., 2006). Inhibition of OLFM4 expression could induce apoptosis in the presence of cytotoxic agent in gastric cancer cells (Kim et al., 2010). Also serum OLFM4 concentration in presurgical GC patients was enhanced as compared to healthy donors (Oue et al., 2009). OLFM4 was identified as a novel target gene for retinoic acids (RAs) and the demethylation agent 5-aza-2'-deoxycytidine. These two agents have proven to be effective in treating certain myeloid leukemia patients (Liu et al., 2010).

Thy-1 Cell Surface Antigen (THY1)

Thy-1 (CD90) is a GPI-anchored glycoprotein found on many cell types including T cells, neurons, endothelial cells and fibroblasts. Thy-1 is involved in processes including adhesion, nerve regeneration, tumor growth, tumor suppression, migration, cell death, and activation of T cells. (Rege and Hagood 2006b; Rege and Hagood 2006a) (Jurisic et al. 2010). Thy-1 appears to be a marker of adult but not embryonic angiogenesis (Lee et al. 1998). Moreover, it was considered as a marker for various kind of stem cells (mesenchymal stem cells, hepatic stem cells ("oval cells") (Masson et al. 2006), keratinocyte stem cells (Nakamura et al. 2006) and hematopoietic stem cells (Yamazaki et al. 2009)). Thy-1 is upregulated in several cancers including gastric cancer and GISTs, for which it was proposed to be a marker (Yang and Chung 2008; Zhang et al. 2010) (Oikonomou et al. 2007).

Centrosomal Protein 250 kDa (CEP250)

Cep250 plays a role in the cohesion of microtubule-organizing centers (Mayor et al., 2000). It is also named centrosomal Nek2-associated protein or C-Nap1, as it colocalizes with and is a substrate of the serine/threonine kinase Nek2. Nek2 kinase and its substrates regulate the linkage between centrosomes (Bahmanyar et al., 2008). At the onset of mitosis, when centrosomes separate for bipolar spindle formation, C-Nap1 is phosphorylated and, subsequently, dissociates from centrosomes. In vitro experiments showed that overexpression of Cep250 impaired microtubule organization at the centrosome (Mayor et al., 2002).

Hypoxia Inducible Factor 1, Alpha Subunit (Basic Helix-Loop-Helix Transcription Factor) (HIF1A)

HIF1A is the oxygen-sensitive subunit of the hypoxia-inducible factor (HIF), a transcription factor active under hypoxic conditions that are frequently found in tumors. It mediates transcription of over 60 genes involved in survival, glucose metabolism, invasion, metastasis and angiogenesis (e.g. VEGF). HIF1 is overexpressed in many cancers, often associated with poor prognosis, and is considered an interesting target for pharmacological manipulation (Griffiths et al. 2005; Quintero et al. 2004; Stoeltzing et al. 2004) (Zhong et al. 1999).

In gastric cancer, HIF1A contributes to angiogenesis (Nam et al. 2011), correlates with tumor size, lower differentiation, tumor stage shorter survival (Qiu et al. 2011) and metastasis (Wang et al. 2010) (Han et al. 2006; Kim et al. 2009; Oh et al. 2008; Ru et al. 2007). It is also thought to lead to resistance to chemotherapeutic drugs such as 5-FU via inhibition of drug-induced apoptosis and decrease of intracellular drug accumulation (Nakamura et al. 2009) (Liu et al. 2008). The HIF-1alpha-inhibitor 2-methoxy-estradiol significantly reduced metastatic properties of gastric cancer cells (Rohwer et al. 2009).

v-Ki-Ras2 Kirsten Rat Sarcoma Viral Oncogene Homolog (KRAS)

KRAS is a member of the small GTPase superfamily and a protooncogene involved in early steps of many signal transduction pathways, such as MAPK- and AKT-mediated pathways, that are potentially oncogenic. Single amino acid substitutions lead to activating mutations, resulting in a transforming protein that plays a key role in various malignancies including gastric cancer (Capella et al., 1991). Oncogenic mutations of KRAS are infrequent in gastric cancer. In a subset of gastric cancers, the KRAS locus was amplified, resulting in overexpression of KRAS protein. Thus, gene amplification likely forms the molecular basis of overactivation of KRAS in gastric cancer (Mita et al., 2009). Mutant KRAS alleles contribute to hypoxia-driven VEGF induction (Kikuchi et al., 2009; Zeng et al., 2010). Mutated KRAS can also be detected in serum or plasma of cancer patients and was, thus, suggested as an easily accessible tumor marker (Sorenson, 2000). The peptide KRAS-001 is derived from only one of two splice variants—NP_004976 (188 amino acids) and not from the splice variant—NP_203524 (189 amino acids). The splice variants differ in their last exon, on which KRAS-001 is located.

Non-SMC Condensin I Complex, Subunit G (NCAPG)

NCAPG is part of the condensin I complex, which is composed of structural maintenance of chromosomes (SMC) and non-SMC proteins, and regulates chromosome condensation and segregation during mitosis (Seipold et al., 2009). NCAPG overexpression was found in numerous tumors including nasopharyngeal carcinoma (Li et al., 2010), hepatocellular carcinoma (Satow et al., 2010) and melanoma (Ryu et al., 2007). Among normal tissues, NCAPG showed highest expression in the testis. It was suggested to be a possible proliferation marker and a potential prognostic indicator in cancer (Jager et al., 2000).

Topoisomerase (DNA) II Alpha (TOP2A) and Topoisomerase (DNA) II Beta (TOP2B)

TOP2A and TOP2B encode highly homologous isoforms of a DNA topoisomerase, which controls and alters topologic states of DNA during transcription and is involved in chromosome condensation, chromatid separation, replication and transcription. Topoisomerase is a target for several anticancer drugs, such as anthracyclins, and a variety of mutations have been associated with drug resistance (Kellner et al., 2002) (Jarvinen and Liu, 2006). TOP2A (not TOP2B) is essential for cell proliferation. It is located adjacent to the HER2 oncogene and is amplified in a great majority of HER2-amplified breast tumors, but also in such without HER2 amplification (Jarvinen and Liu, 2003), and in many other tumor entities. Also in a subset of gastric cancers, TOP2A was found amplified and overexpressed, frequently together with HER2 (Varis et al., 2002) (Liang et al., 2008).

Laminin, Gamma 2 (LAMC2)

Laminins are the major non-collagenous constituents of basement membranes. They are involved in cell adhesion, differentiation, migration, signaling, and metastasis. The gamma 2 chain together with alpha 3 and beta 3 chains constitute laminin 5. LAMC2 promotes invasive growth of human cancer cells in vivo. It is highly expressed by human cancers at the invasion front, and expression correlates with poor prognosis (Tsubota et al., 2010). A MMP-2-generated cleavage product of laminin 5 is able to activate EGFR signaling and promote cell motility (Schenk et al., 2003). In gastric carcinoma, LAMC2 may be induced by members of the EGFR family or by Wnt5a, and invasive activity was shown to depend on LAMC2 (Tsubota et al., 2010) (Yamamoto et al., 2009).

Aryl Hydrocarbon Receptor (AHR)

AHR binds planar aromatic hydrocarbons such as TCDD (2,3,7,8-tetrachlorodibenzo-p-dioxin), and mediates transcription of genes including xenobiotic-metabolizing enzymes such as cytochrome P450 enzymes. It also plays a role in cell cycle progression (Barhoover et al. 2010). AhR is thought to be partly associated with the tumor promoting activity of dioxin, as it has pro-proliferative and anti-apoptotic functions, and may lead to deregulation of cell-cell contact, dedifferentiation and enhanced motility (Watabe et al. 2010) (Dietrich and Kaina 2010) (Marlowe et al. 2008). AHR expression can be down-regulated by TGF-beta (Dohr and Abel 1997; Wolff et al. 2001) and induced by Wnt or beta-catenin signaling (Chesire et al. 2004). AHR overexpression was found in many cancers including gastric cancer, where it correlated with the frequent CYP1A1 expression (Ma et al. 2006). AHR expression and nuclear translocation were higher in gastric cancer than in normal tissues, and expression increased gradually during cancerogenesis (Peng et al. 2009a). AhR pathway activation enhances gastric cancer cell invasiveness likely through a c-Jun-dependent induction of MMP-9 (Peng et al. 2009b). In a mouse model, expression of a constitutively active mutant of the aryl hydrocarbon receptor (CA-AhR) results in development of stomach tumours, correlating with increased mortality (Andersson et al. 2002; Kuznetsov et al. 2005). The function of AhR in cancer appears to be ambiguous, as some studies also point towards a tumor-suppressing activity (Gluschnaider et al. 2010)(Fan et al. 2010).

Hyaluronan-Mediated Motility Receptor (RHAMM) (HMMR)

HMMR can occur on the cell surface where it binds hyaluronic acid (HA) and interacts with the HA receptor CD44. This interaction plays a role in processes like cell motility, wound healing and invasion (Gares and Pilarski, 2000). Intracellularly, HMMR associates with the cytoskeleton, microtubules, centrosomes and the mitotic spindle and plays a role in control of mitotic spindle integrity. HMMR is overexpressed in several cancer tissues (Sohr and Engeland, 2008). HA was suggested to protect cancer cells against immune attack. Serum HA is often increased in metastatic patients (Delpech et al., 1997). HMMR was identified as promising tumor-associated antigen and possible prognostic factor in AML and CLL. Peptides derived from HMMR have been used in anti-leukemia vaccines. HMMR-001 was tested for in vitro immunogenicity as well, but not used for vaccination (Tzankov et al., 2011) (Greiner et al., 2010; Schmitt et al., 2008; Tabarkiewicz and Giannopoulos, 2010) (Greiner et al., 2005). HMMR overexpression was also found in several other cancers, often associated with bad prognosis. HMMR was also overexpressed in gastric cancer, often together with CD44, and was suggested to facilitate invasion and metastasis (Li et al., 1999) (Li et al., 2000a) (Li et al., 2000b).

TPX2, Microtubule-Associated, Homolog (*Xenopus laevis*) (TPX2)

TPRX2 is a proliferation-associated protein expressed in S-, G(2)- and M-phases of the cell cycle and regarded as a proliferation marker (Cordes et al., 2010).

It is required for normal microtubule nucleation, e.g. for assembly of mitotic spindles. TPX2 recruits and activates Aurora A (Bird and Hyman, 2008; Moss et al., 2009). Phosphorylation of TPX2 with Polo-like kinase 1 increases its ability to activate Aurora A (Eckerdt et al., 2009). TPX2 is overexpressed in many tumor types and frequently co-overexpressed with Aurora-A (Asteriti et al., 2010). Examples where TPX2 overexpression was found (frequently associated with bad prognosis or later stage) are meningioma (Stuart et al., 2010), lung cancer (Kadara et al., 2009) (Lin et al., 2006; Ma et al., 2006) (Manda et al., 1999) and hepatocellular carcinoma (Shigeishi et al., 2009b) (Satow et al., 2010) (Wang et al., 2003).

The present invention therefore relates to a peptide comprising a sequence that is selected from the group of SEQ ID NO: 1 to SEQ ID NO: 95 or a variant thereof which is at least 80% homolog to SEQ ID NO: 1 to SEQ ID NO: 95 or a variant thereof that induces T cells cross-reacting with said peptide, wherein said peptide is not a full-length polypeptide.

The present invention further relates to a peptide comprising a sequence that is selected from the group of SEQ ID NO: 1 to SEQ ID NO: 95 or a variant thereof which is at least 80% homolog to SEQ ID NO:: 1 to SEQ ID NO: 95, wherein said peptide or variant has an overall length of not more than 100, not more than 30, and most preferred from 8 to 14 amino acids.

The present invention further relates to the peptides previously described, having the ability to bind to a molecule of the human major histocompatibility complex (MHC) class-I or -II.

The present invention further relates to the peptides previously described wherein the peptide consists or consists essentially of an amino acid sequence according to SEQ ID NO: 1 to SEQ ID NO: 95.

The present invention further relates to the peptides previously described, wherein the peptide is modified and/or includes non-peptide bonds.

The present invention further relates to the peptides previously described, wherein the peptide is a fusion protein, in particular comprising N-terminal amino acids of the HLA-DR antigen-associated invariant chain (Ii).

The present invention further relates to a nucleic acid, encoding the peptides previously described, provided, that the peptide is not the full human protein.

The present invention further relates to the nucleic acid previously described which is DNA, cDNA, PNA, CNA, RNA or combinations thereof.

The present invention further relates to an expression vector capable of expressing a nucleic acid previously described.

The present invention further relates to a peptide as described before, a nucleic acid as described before or an expression vector as described before for use in medicine.

The present invention further relates to a host cell comprising a nucleic acid as described before or an expression vector as described before.

The present invention further relates to the host cell described that is an antigen presenting cell.

The present invention further relates to the host cell described wherein the antigen presenting cell is a dendritic cell.

The present invention further relates to a method of producing a peptide described, the method comprising culturing the host cell described and isolating the peptide from the host cell or its culture medium.

The present invention further relates to an in vitro method for producing activated cytotoxic T lymphocytes (CTL), the method comprising contacting in vitro CTL with antigen loaded human class I or II MHC molecules expressed on the surface of a suitable antigen-presenting cell for a period of time sufficient to activate said CTL in an antigen specific manner, wherein said antigen is any peptide described.

The present invention further relates to the method as described, wherein the antigen is loaded onto class I or II MHC molecules expressed on the surface of a suitable antigen-presenting cell by contacting a sufficient amount of the antigen with an antigen-presenting cell.

The present invention further relates to the method as described, wherein the antigen-presenting cell comprises an expression vector capable of expressing said peptide containing SEQ ID NO 1 to SEQ ID NO 33 or said variant amino acid sequence.

The present invention further relates to activated cytotoxic T lymphocytes (CTL), produced by the method described, which selectively recognise a cell which aberrantly expresses a polypeptide comprising an amino acid sequence described.

The present invention further relates to a method of killing target cells in a patient which target cells aberrantly express a polypeptide comprising any amino acid sequence described, the method comprising administering to the patient an effective number of cytotoxic T lymphocytes (CTL) as defined.

The present invention further relates to the use of any peptide described, a nucleic acid as described, an expression vector as described, a cell as described, or an activated cytotoxic T lymphocyte as described as a medicament or in the manufacture of a medicament.

The present invention further relates to a use as described, wherein the medicament is a vaccine.

The present invention further relates to a use as described, wherein the medicament is active against cancer.

The present invention further relates to a use as described, wherein said cancer cells are gastric cancer cells, gastrointestinal, colorectal, pancreatic, lung or renal.

The present invention further relates to particular marker proteins that can be used in the prognosis of gastric cancer.

Further, the present invention relates to the use of these novel targets for cancer treatment.

As provided herein, the proteins encoded by ABL1, ADAM10, AHR, CCND2, CDC6, CDK1, CEACAM1, CEACAM5, CEACAM6, CEACAM6, COL6A3, EIF2S3, LOC255308, EPHA2, ERBB2, ERBB3, F2R, FAP, HMMR, HSP90B1, IGF2BP3, ITGB4, KIF2C, KRAS, LAMC2, LCN2, MET, MMP11, MMP12, MMP3, MST1R, NUF2, OLFM4, PROM1, RRM2, THY1, TMPRSS4, TOP2A, TSPAN1, WNT5A, HIF1A, and PTK2 were described to be overexpressed in gastric cancer compared with normal gastric and other vital tissues (e.g. liver kidney, heart) in literature.

The proteins encoded by ABL1, ADAM10, ADAMS, AHR, ASPM, ATAD2, CCDC88A, CCNB1, CCND2, CCNE2, CDC6, CDK1, CEACAM1, CEACAM5, CEACAM6, CEACAM6, CLCN3, COL6A3, EPHA2, ERBB2, ERBB3, F2R, FAP, HIF1A, HMMR, HSP90B1, IGF2BP3, IQGAP3, ITGB4, KIF11, KIF2C, KRAS, LAMC2, LCN2, MET, MMP11, MMP3, MST1R, MUC6, NCAPG, NFYB, NUF2, OLFM4, PBK, PLK4, PPAP2C, PROM1, PTK2, RRM2, SIAH2, THY1, TOP2A, TPX2, TSPAN1, TSPAN8, UBE2S, UCHL5, and WNT5A were shown to have an important role in tumorgenesis as they are involved in malignant transformation, cell growth, proliferation, angiogenesis or invasion into normal tissue. Also for the proteins encoded by DNAJC10, EIF2S3, EIF3L, POLD3, PSMC2, PSMD14, and TMPRSS4, there is some evidence for cancer-relevant functions.

The proteins encoded by PROM1, WNT5A, SMC4, PPAP2C, GPR38, OLFM4 and THY1 have been shown to be highly expressed and/or functionally important in stem cells and/or cancer stem cells. PROM1 has been discussed as marker for gastric cancer stem cells, although data are controversial. Cancer stem cells are a tumor cell subpopulation with self-renewing potential required for sustained tumor growth. These cells reside in specialized and highly organized structures, so called cancer stem cell niches that are required for the maintenance of the self-renewing potential of cancer stem cells.

Overexpression of the proteins AHR, ASPM, ATAD2, CCNB1, CCND2, CCNE2, CDK1 (CDC2), CEACAM1, CEACAM5, CEACAM6, CEACAM6, COL6A3, EPHA2, ERBB2, ERBB3, F2R, FAP, HIF1A, HMMR, HSP90B1, IGF2BP3, ITGB4, KIF11, KIF2C, KRAS, LAMC2, LCN2, LMNB1, MET, MMP11, MMP3, MST1R, MUC6, NCAPG, NUF2, OLFM4, PBK, PPAP2C, PROM1, PTK2, TMPRSS4, TPX2, TSPAN1, and WNT5A in tumors has been shown to be associated with advanced disease stages and poor prognosis for the patients.

Therefore, the present invention provides methods of identifying an animal, preferably a human, which is likely to have gastric cancer. In one embodiment the likelihood determined is from 80% to 100%. One such method comprises determining the level of at least one of the proteins MST1R, UCHL5, SMC4, NFYB, PPAP2C, AVL9, UQCRB and MUC6 in a tumor sample from the animal subject. In one embodiment, the sample is obtained by radical surgery. In another embodiment, the sample is obtained by needle biopsy.

When the level of MST1R, UCHL5, SMC4, NFYB, PPAP2C, AVL9, UQCRB or MUC6 determined is 20% or more up-regulated in cells relative to that determined in benign epithelial cells of the same specimen, the animal subject is identified as being likely to have gastric cancer.

The more different proteins of the group comprising MST1R, UCHL5, SMC4, NFYB, PPAP2C, AVL9, UQCRB and MUC6 are up-regulated the higher the possibility of the animal subject is identified as being likely to have gastric cancer.

In one embodiment the determination of the level of MST1R, UCHL5, SMC4, NFYB, PPAP2C, AVL9, UQCRB or MUC6 is performed in situ. In another embodiment the determination of the level of MST1R, UCHL5, SMC4, NFYB, PPAP2C, AVL9, UQCRB or MUC6 is performed in vitro. In still another embodiment, the determination of the level of MST1R, UCHL5, SMC4, NFYB, PPAP2C, AVL9, UQCRB or MUC6 is performed in vivo. In a preferred embodiment, the determination of the level of MST1R, UCHL5, SMC4, NFYB, PPAP2C, AVL9, UQCRB or MUC6 is performed by Laser Capture Microscopy coupled with a Western blot.

In a particular embodiment, the determination of the level of MST1R, UCHL5, SMC4, NFYB, PPAP2C, AVL9, UQCRB or MUC6 is performed with an antibody specific for MST1R, UCHL5, SMC4, NFYB, PPAP2C, AVL9, UQCRB or MUC6. In another such embodiment the determination of the level of MST1R, UCHL5, SMC4, NFYB, PPAP2C, AVL9, UQCRB or MUC6 is performed by PCR with a primer specific for an mRNA encoding MST1R, UCHL5, SMC4, NFYB, PPAP2C, AVL9, UQCRB or MUC6. In still another embodiment the determination of the level of MST1R, UCHL5, SMC4, NFYB, PPAP2C, AVL9, UQCRB or MUC6 is performed with a nucleotide probe specific for an mRNA encoding MST1R, UCHL5, SMC4, NFYB, PPAP2C, AVL9, UQCRB or MUC6. In one such embodiment, the determination of the level of MST1R, UCHL5, SMC4, NFYB, PPAP2C, AVL9, UQCRB or MUC6 is performed by a Northern blot. In another embodiment, the determination of the level of MST1R, UCHL5, SMC4, NFYB, PPAP2C, AVL9, UQCRB or MUC6 is performed by a ribonuclease protection assay. In other embodiments, immunological tests such as enzyme-linked immunosorbent assays (ELISA), radioimmunoassays (RIA), and Western blots may be used to detect MST1R, UCHL5, SMC4, NFYB, PPAP2C, AVL9, UQCRB and MUC6 polypeptides in a body fluid sample (such as blood, serum, sputum, urine, or peritoneal fluid). Biopsies, tissue samples, and cell samples (such as ovaries, lymph nodes, ovarian surface epithelial cell scrapings, lung biopsies, liver biopsies, and any fluid sample containing cells (such as peritoneal fluid, sputum, and pleural effusions) may be tested by disaggregating and/or solubilizing the tissue or cell sample and subjecting it to an immunoassay for polypeptide detection, such as ELISA, RIA, or Western blotting. Such cell or tissue samples may also be analyzed by nucleic acid-based methods, e.g., reverse transcription-polymerase chain reaction (RT-PCR) amplification, Northern hybridization, or slot- or dot-blotting. To visualize the distribution of tumor cells within a tissue sample, diagnostic tests that preserve the tissue structure of a sample, e.g., immunohistological staining, in situ RNA hybridization, or in situ RT-PCR may be employed to detect gastric cancer marker polypeptide or mRNA, respectively. For in vivo localization of tumor masses, imaging tests such as magnetic resonance imaging (MRI) may be employed by introducing into the subject an antibody that specifically binds a MST1R, UCHL5, SMC4, NFYB, PPAP2C, AVL9, UQCRB or MUC6 polypeptide (particularly a cell surface-localized polypeptide), wherein the antibody is conjugated or otherwise coupled to a paramagnetic tracer (or other appropriate detectable moiety, depending upon the imaging method used); alternatively, localization of an unlabeled tumor marker-specific antibody may be detected using a secondary antibody coupled to a detectable moiety.

In addition, the present invention further provides chimeric/fusion proteins/peptides comprising the MST1R, UCHL5, SMC4, NFYB, PPAP2C, AVL9, UQCRB or MUC6 polypeptides, and fragments thereof, including functional, proteolytic and antigenic fragments.

The fusion partner or sections of a hybrid molecule suitably provide epitopes that stimulate CD4+ T-cells. CD4+ stimulating epitopes are well known in the art and include those identified in tetanus toxoid. In a further preferred embodiment the peptide is a fusion protein, in particular comprising N-terminal amino acids of the HLA-DR antigen-associated invariant chain (Ii). In one embodiment the peptide of the invention is a truncated human protein or a fusion protein of a protein fragment and another polypeptide portion provided that the human portion includes one or more inventive amino acid sequences.

Antibodies to the MST1R, UCHL5, SMC4, NFYB, PPAP2C, AVL9, UQCRB or MUC6 polypeptides, to the chimeric/fusion proteins comprising the MST1R, UCHL5, SMC4, NFYB, PPAP2C, AVL9, UQCRB or MUC6 polypeptides, as well as to the fragments of the MST1R, UCHL5, SMC4, NFYB, PPAP2C, AVL9, UQCRB or MUC6 polypeptides, including proteolytic, and antigenic fragments, and to the chimeric/fusion proteins/peptides comprising these fragments are also part of the present invention. In addition, methods of using such antibodies for the prognosis of cancer, and gastric cancer in particular, are also part of the present invention.

The antibodies of the present invention can be polyclonal antibodies, monoclonal antibodies and/or chimeric antibodies. Immortal cell lines that produce a monoclonal antibody of the present invention are also part of the present invention.

One of ordinary skill in the art will understand that in some instances, higher expression of MST1R, UCHL5, SMC4, NFYB, PPAP2C, AVL9, UQCRB or MUC6 as a tumor marker gene will indicate a worse prognosis for a subject having gastric cancer. For example, relatively higher levels MST1R, UCHL5, SMC4, NFYB, PPAP2C, AVL9, UQCRB or MUC6 expression may indicate a relative large primary tumor, a higher tumor burden (e.g., more metastases), or a relatively more malignant tumor phenotype.

The more different proteins of the group comprising MST1R, UCHL5, SMC4, NFYB, PPAP2C, AVL9, UQCRB and MUC6 are overexpressed the worse the prognosis is.

The diagnostic and prognostic methods of the invention involve using known methods, e.g., antibody-based methods to detect MST1R, UCHL5, SMC4, NFYB, PPAP2C, AVL9, UQCRB and MUC6 polypeptides and nucleic acid hybridization- and/or amplification-based methods to detect MST1R, UCHL5, SMC4, NFYB, PPAP2C, AVL9, UQCRB, and MUC6 mRNA.

In addition, since rapid tumor cell destruction often results in autoantibody generation, the gastric cancer tumor markers of the invention may be used in serological assays (e.g., an ELISA test of a subject's serum) to detect autoantibodies against MST1R, UCHL5, SMC4, NFYB, PPAP2C, AVL9, UQCRB or MUC6 in a subject. MST1R, UCHL5, SMC4, NFYB, PPAP2C, AVL9, UQCRB, and MUC6 polypeptide-specific autoantibody levels that are at least about 3-fold higher (and preferably at least 5-fold or 7-fold higher, most preferably at least 10-fold or 20-fold higher) than in a control sample are indicative of gastric cancer.

Cell-surface localized, intracellular, and secreted MST1R, UCHL5, SMC4, NFYB, PPAP2C, AVL9, UQCRB and MUC6 polypeptides may all be employed for analysis of biopsies, e.g., tissue or cell samples (including cells obtained from liquid samples such as peritoneal cavity fluid) to identify a tissue or cell biopsy as containing gastric cancer cells. A biopsy may be analyzed as an intact tissue or as a whole-cell sample, or the tissue or cell sample may be disaggregated and/or solubilized as necessary for the particular type of diagnostic test to be used. For example, biopsies or samples may be subjected to whole-tissue or whole-cell analysis of MST1R, UCHL5, SMC4, NFYB, PPAP2C, AVL9, UQCRB and MUC6 polypeptide or mRNA levels in situ, e.g., using immunohistochemistry, in situ mRNA hybridization, or in situ RT-PCR. The skilled artisan will know how to process tissues or cells for analysis of polypeptide or mRNA levels using immunological methods such as ELISA, immunoblotting, or equivalent methods, or analysis of mRNA levels by nucleic acid-based analytical methods such as RT-PCR, Northern hybridization, or slot- or dot-blotting.

Kits for Measuring Expression Levels of MST1R, UCHL5, SMC4, NFYB, PPAP2C, AVL9, UQCRB, and MUC6.

The present invention provides kits for detecting an increased expression level of MST1R, UCHL5, SMC4, NFYB, PPAP2C, AVL9, UQCRB and MUC6 as a gastric cancer marker gene in a subject. A kit for detecting gastric cancer marker polypeptide preferably contains an antibody that specifically binds a chosen gastric cancer marker polypeptide. A kit for detecting gastric cancer marker mRNA preferably contains one or more nucleic acids (e.g., one or more oligonucleotide primers or probes, DNA probes, RNA probes, or templates for generating RNA probes) that specifically hybridize with MST1R, UCHL5, SMC4, NFYB, PPAP2C, AVL9, UQCRB, and MUC6 mRNA.

Particularly, the antibody-based kit can be used to detect the presence of, and/or measure the level of, a MST1R, UCHL5, SMC4, NFYB, PPAP2C, AVL9, UQCRB and MUC6 polypeptide that is specifically bound by the antibody or an immunoreactive fragment thereof. The kit can include an antibody reactive with the antigen and a reagent for detecting a reaction of the antibody with the antigen. Such a kit can be an ELISA kit and can contain a control (e.g., a specified amount of a particular gastric cancer marker polypeptide), primary and secondary antibodies when appropriate, and any other necessary reagents such as detectable moieties, enzyme substrates and color reagents as described above. The diagnostic kit can, alternatively, be an immunoblot kit generally comprising the components and reagents described herein.

A nucleic acid-based kit can be used to detect and/or measure the expression level of MST1R, UCHL5, SMC4, NFYB, PPAP2C, AVL9, UQCRB and MUC6 by detecting and/or measuring the amount of MST1R, UCHL5, SMC4, NFYB, PPAP2C, AVL9, UQCRB and MUC6 mRNA in a sample, such as a tissue or cell biopsy. For example, an RT-PCR kit for detection of elevated expression of MST1R, UCHL5, SMC4, NFYB, PPAP2C, AVL9, UQCRB and MUC6 preferably contains oligonucleotide primers sufficient to perform reverse transcription of gastric cancer marker mRNA to cDNA and PCR amplification of gastric cancer marker cDNA, and will preferably also contain control PCR template molecules and primers to perform appropriate negative and positive controls, and internal controls for quantization. One of ordinary skill in the art will understand how to select the appropriate primers to perform the reverse transcription and PCR reactions, and the appropriate control reactions to be performed. Such guidance is found, for example, in F. Ausubel et al., Current Protocols in Molecular Biology, John Wiley & Sons, New York, N.Y., 1997. Numerous variations of RT-PCR are known in the art. Targeted Delivery of immunotoxins to MST1R, UCHL5, SMC4, NFYB, PPAP2C, AVL9, UQCRB and MUC6 can be employed as therapeutic targets for the treatment or prevention of gastric cancer. For example, an antibody molecule that specifically binds a cell surface-localized MST1R, UCHL5, SMC4, NFYB, PPAP2C, AVL9, UQCRB and MUC6 polypeptide can be conjugated to a radioisotope or other toxic compound. Antibody conjugates are administered to the subject so that the binding of the antibody to its cognate gastric cancer polypeptide results in the targeted delivery of the therapeutic compound to gastric cancer cells, thereby treating an ovarian cancer.

The therapeutic moiety can be a toxin, radioisotope, drug, chemical, or a protein (see, e.g., Bera et al. "Pharmacokinetics and antitumor activity of a bivalent disulfide-stabilized Fv immunotoxin with improved antigen binding to erbB2" Cancer Res. 59:4018-4022 (1999)). For example, the antibody can be linked or conjugated to a bacterial toxin (e.g., diptheria toxin, *pseudomonas* exotoxin A, cholera toxin) or plant toxin (e.g., ricin toxin) for targeted delivery of the toxin to a cell expressing MST1R, UCHL5, SMC4, NFYB, PPAP2C, AVL9, UQCRB and MUC6 This immunotoxin can be delivered to a cell and upon binding the cell surface-localized gastric cancer marker polypeptide, the toxin conjugated to the gastric cancer marker-specific antibody will be delivered to the cell.

In addition, for any MST1R, UCHL5, SMC4, NFYB, PPAP2C, AVL9, UQCRB and MUC6 polypeptide for which there is a specific ligand (e.g., a ligand that binds a cell surface-localized protein), the ligand can be used in place of an antibody to target a toxic compound to a gastric cancer cell, as described above.

The term "antibodies" is used herein in a broad sense and includes both polyclonal and monoclonal antibodies. In addition to intact immunoglobulin molecules, also included in the term "antibodies" are fragments or polymers of those immunoglobulin molecules and humanized versions of immunoglobulin molecules, so long as they exhibit any of the desired properties (e.g., specific binding of an gastric cancer marker polypeptide, delivery of a toxin to an gastric cancer cell expressing an gastric cancer marker gene at an increased level, and/or inhibiting the activity of an gastric cancer marker polypeptide) described herein.

Whenever possible, the antibodies of the invention may be purchased from commercial sources. The antibodies of the invention may also be generated using well-known methods. The skilled artisan will understand that either full length gastric cancer marker polypeptides or fragments thereof may be used to generate the antibodies of the invention. A polypeptide to be used for generating an antibody of the invention may be partially or fully purified from a natural source, or may be produced using recombinant DNA techniques. For example, a cDNA encoding a MST1R, UCHL5, SMC4, NFYB, PPAP2C, AVL9, UQCRB or MUC6 polypeptide, or a fragment thereof, can be expressed in prokaryotic cells (e.g., bacteria) or eukaryotic cells (e.g., yeast, insect, or mammalian cells), after which the recombinant protein can be purified and used to generate a monoclonal or polyclonal antibody preparation that specifically bind the gastric cancer marker polypeptide used to generate the antibody.

One of skill in the art will know that the generation of two or more different sets of monoclonal or polyclonal antibodies maximizes the likelihood of obtaining an antibody with the specificity and affinity required for its intended use (e.g., ELISA, immunohistochemistry, in vivo imaging, immunotoxin therapy). The antibodies are tested for their desired activity by known methods, in accordance with the purpose for which the antibodies are to be used (e.g., ELISA, immunohistochemistiy, immunotherapy, etc.; for further guidance on the generation and testing of antibodies, see, e.g., Harlow and Lane, Antibodies: A Laboratory Manual, Cold Spring Harbor Laboratory Press, Cold Spring Harbor, N.Y., 1988). For example, the antibodies may be tested in ELISA assays, Western blots, immunohistochemical staining of formalin-fixed gastric cancers or frozen tissue sections. After their initial in vitro characterization, antibodies intended for therapeutic or in vivo diagnostic use are tested according to known clinical testing methods.

The term "monoclonal antibody" as used herein refers to an antibody obtained from a substantially homogeneous population of antibodies, i.e.; the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired antagonistic activity (U.S. Pat. No. 4,816,567).

Monoclonal antibodies of the invention may be prepared using hybridoma methods. In a hybridoma method, a mouse or other appropriate host animal, is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies).

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fe fragment. Pepsin treatment yields a fragment that has two antigen combining sites and is still capable of cross-linking antigen.

The antibody fragments, whether attached to other sequences or not, can also include insertions, deletions, substitutions, or other selected modifications of particular regions or specific amino acids residues, provided the activity of the fragment is not significantly altered or impaired compared to the nonmodified antibody or antibody fragment. These modifications can provide for some additional property, such as to remove/add amino acids capable of disulfide bonding, to increase its bio-longevity, to alter its secretory characteristics, etc. In any case, the antibody fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody fragment.

The antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab' or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework (FR) residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region gene in chimeric and germ-line mutant mice results in complete inhibition of endogenous antibody production. Transfer of the human germ-line immunoglobulin gene array in such germ-line mutant mice will result in the production of human antibodies upon antigen challenge. Human antibodies can also be produced in phage display libraries.

Antibodies of the invention are preferably administered to a subject in a pharmaceutically acceptable carrier. Typically, an appropriate amount of a pharmaceutically-acceptable salt is used in the formulation to render the formulation isotonic. Examples of the pharmaceutically-acceptable carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The antibodies can be administered to the subject, patient, or cell by injection (e.g., intravenous, intraperitoneal, subcutaneous, intramuscular), or by other methods such as infusion that ensure its delivery to the bloodstream in an effective form. The antibodies may also be administered by intratumoral or peritumoral routes, to exert local as well as systemic therapeutic effects. Local or intravenous injection is preferred.

Effective dosages and schedules for administering the antibodies may be determined empirically, and making such determinations is within the skill in the art. Those skilled in the art will understand that the dosage of antibodies that must be administered will vary depending on, for example, the subject that will receive the antibody, the route of administration, the particular type of antibody used and other drugs being administered. A typical daily dosage of the antibody used alone might range from about 1 (µg/kg to up to 100 mg/kg of body weight or more per day, depending on the factors mentioned above. Following administration of an antibody for treating gastric cancer, the efficacy of the therapeutic antibody can be assessed in various ways well known to the skilled practitioner. For instance, the size, number, and/or distribution of gastric cancer in a subject receiving treatment may be monitored using standard tumor imaging techniques. A therapeutically-administered antibody that arrests tumor growth, results in tumor shrinkage, and/or prevents the development of new tumors, compared to the disease course that would occurs in the absence of antibody administration, is an efficacious antibody for treatment of gastric cancer.

Because the proteins ABL1, ADAM10, AHR, CCND2, CDC6, CDK1, CEACAM1, CEACAM5, CEACAM6, CEACAM6, COL6A3, EIF2S3, LOC255308, EPHA2, ERBB2, ERBB3, F2R, FAP, HMMR, HSP90B1, IGF2BP3, ITGB4, KIF2C, KRAS, LAMC2, LCN2, MET, MMP11, MMP12, MMP3, MST1R, NUF2, OLFM4, PROM1, RRM2, THY1, TMPRSS4, TOP2A, TSPAN1, WNT5A, HIF1A, and PTK2 have been shown to be highly expressed in at least a subset of gastric cancer tissues as compared to normal tissues, inhibition of their expression or activity may be integrated into any therapeutic strategy for treating or preventing gastric cancer.

The principle of antisense therapy is based on the hypothesis that sequence-specific suppression of gene expression (via transcription or translation) may be achieved by intracellular hybridization between genomic DNA or mRNA and a complementary antisense species. The formation of such a hybrid nucleic acid duplex interferes with transcription of the target tumor antigen-encoding genomic DNA, or processing/transport/translation and/or stability of the target tumor antigen mRNA.

Antisense nucleic acids can be delivered by a variety of approaches. For example, antisense oligonucleotides or antisense RNA can be directly administered (e.g., by intravenous injection) to a subject in a form that allows uptake into tumor cells. Alternatively, viral or plasmid vectors that encode antisense RNA (or RNA fragments) can be introduced into cells in vivo. Antisense effects can also be induced by sense sequences; however, the extent of phenotypic changes is highly variable. Phenotypic changes induced by effective antisense therapy are assessed according to changes in, e.g., target mRNA levels, target protein levels, and/or target protein activity levels.

In a specific example, inhibition of gastric tumor marker function by antisense gene therapy may be accomplished by direct administration of antisense gastric tumor marker RNA to a subject. The antisense tumor marker RNA may be produced and isolated by any standard technique, but is most readily produced by in vitro transcription using an antisense tumor marker cDNA under the control of a high efficiency promoter (e.g., the T7 promoter). Administration of antisense tumor marker RNA to cells can be carried out by any of the methods for direct nucleic acid administration described below.

An alternative strategy for inhibiting MST1R, UCHL5, SMC4, NFYB, PPAP2C, AVL9, UQCRB or MUC6 function using gene therapy involves intracellular expression of an anti-MST1R, UCHL5, SMC4, NFYB, PPAP2C, AVL9, UQCRB or MUC6 antibody or a portion of an anti-MST1R, UCHL5, SMC4, NFYB, PPAP2C, AVL9, UQCRB or MUC6 antibody. For example, the gene (or gene fragment) encoding a monoclonal antibody that specifically binds to a MST1R, UCHL5, SMC4, NFYB, PPAP2C, AVL9, UQCRB or MUC6 polypeptide and inhibits its biological activity is placed under the transcriptional control of a specific (e.g., tissue- or tumor-specific) gene regulatory sequence, within a nucleic acid expression vector. The vector is then administered to the subject such that it is taken up by gastric cancer cells or other cells, which then secrete the anti-MST1R, UCHL5, SMC4, NFYB, PPAP2C, AVL9, UQCRB or MUC6 antibody and thereby block biological activity of the MST1R, UCHL5, SMC4, NFYB, PPAP2C, AVL9, UQCRB and MUC6 polypeptide. Preferably, the MST1R, UCHL5, SMC4, NFYB, PPAP2C, AVL9, UQCRB and MUC6 polypeptides are present at the extracellular surface of gastric cancer cells.

In the methods described above, which include the administration and uptake of exogenous DNA into the cells of a subject (i.e., gene transduction or transfection), the nucleic acids of the present invention can be in the form of naked DNA or the nucleic acids can be in a vector for delivering the nucleic acids to the cells for inhibition of gastric tumor marker protein expression. The vector can be a commercially available preparation, such as an adenovirus vector (Quantum Biotechnologies, Inc. (Laval, Quebec, Canada). Delivery of the nucleic acid or vector to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the nucleic acid or vector of this invention can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

As one example, vector delivery can be via a viral system, such as a retroviral vector system that can package a recombinant retroviral genome. The recombinant retrovirus can then be used to infect and thereby deliver to the infected cells antisense nucleic acid that inhibits expression of MST1R, UCHL5, SMC4, NFYB, PPAP2C, AVL9, UQCRB or MUC6. The exact method of introducing the altered nucleic acid into mammalian cells is, of course, not limited to the use of retroviral vectors. Other techniques are widely available for this procedure including the use of adenoviral vectors, adeno-associated viral (AAV) vectors, lentiviral vectors, pseudotyped retroviral vectors. Physical transduction techniques can also be used, such as liposome delivery and receptor-mediated and other endocytosis mechanisms. This invention can be used in conjunction with any of these or other commonly used gene transfer methods.

The antibodies may also be used for in vivo diagnostic assays. Generally, the antibody is labeled with a radionucleotide (such as 111In, 99Tc, 14C, 1311, 3H, 32 P or 35 S) so that the tumor can be localized using immunoscintiography. In one embodiment, antibodies or fragments thereof bind to the extracellular domains of two or more MST1R, UCHL5, SMC4, NFYB, PPAP2C, AVL9, UQCRB, and MUC6 targets and the affinity value (Kd) is less than 1×10 µM.

Antibodies for diagnostic use may be labeled with probes suitable for detection by various imaging methods. Methods for detection of probes include, but are not limited to, fluorescence, light, confocal and electron microscopy; magnetic resonance imaging and spectroscopy; fluoroscopy, computed tomography and positron emission tomography. Suitable probes include, but are not limited to, fluorescein, rhodamine, eosin and other fluorophores, radioisotopes, gold, gadolinium and other lanthanides, paramagnetic iron, fluorine-18 and other positron-emitting radionuclides. Additionally, probes may be bi- or multi-functional and be detectable by more than one of the methods listed. These antibodies may be directly or indirectly labeled with said probes. Attachment of probes to the antibodies includes covalent attachment of the probe, incorporation of the probe into the antibody, and the covalent attachment of a chelating compound for binding of probe, amongst others well recognized in the art. For immunohistochemistry, the disease tissue sample may be fresh or frozen or may be embedded in paraffin and fixed with a preservative such as formalin. The fixed or embedded section contains the sample are contacted with a labeled primary antibody and secondary antibody, wherein the antibody is used to detect the MST1R, UCHL5, SMC4, NFYB, PPAP2C, AVL9, UQCRB and MUC6 proteins express in situ.

The present invention thus provides a peptide comprising a sequence that is selected from the group of SEQ ID NO: 1 to SEQ ID NO: 95 or a variant thereof which is 85%, preferably 90% and more preferred 96%, homologous to SEQ ID NO: 1 to SEQ ID NO: 95 or a variant thereof that will induce T cells cross-reacting with said peptide.

The peptides of the invention have the ability to bind to a molecule of the human major histocompatibility complex (MHC) class-I.

In the present invention, the term "homologous" refers to the degree of identity between sequences of two amino acid sequences, i.e. peptide or polypeptide sequences. The aforementioned "homology" is determined by comparing two sequences aligned under optimal conditions over the sequences to be compared. The sequences to be compared herein may have an addition or deletion (for example, gap and the like) in the optimum alignment of the two sequences. Such a sequence homology can be calculated by creating an alignment using, for example, the ClustalW algorithm. Commonly available sequence analysis software, more specifically, Vector NTI, GENETYX or analysis tools provided by public databases.

A person skilled in the art will be able to assess, whether T cells induced by a variant of a specific peptide will be able to cross-react with the peptide itself (Fong et al. 8809-14); (Appay et al. 1805-14; Colombetti et al. 2730-38; Zaremba et al. 4570-77).

By a "variant" of the given amino acid sequence the inventors mean that the side chains of, for example, one or two of the amino acid residues are altered (for example by replacing them with the side chain of another naturally occurring amino acid residue or some other side chain) such that the peptide is still able to bind to an HLA molecule in substantially the same way as a peptide consisting of the given amino acid sequence in SEQ ID NO: 1 to 33. For example, a peptide may be modified so that it at least maintains, if not improves, the ability to interact with and bind to the binding groove of a suitable MHC molecule, such as HLA-A*02 or -DR, and in that way it at least maintains, if not improves, the ability to bind to the TCR of activated CTL.

These CTL can subsequently cross-react with cells and kill cells that express a polypeptide which contains the natural amino acid sequence of the cognate peptide as defined in the aspects of the invention. As can be derived from the scientific literature (Rammensee, Bachmann, and Stevanovic) and databases (Rammensee et al. 213-19), certain positions of HLA binding peptides are typically anchor residues forming a core sequence fitting to the binding motif of the HLA receptor, which is defined by polar, electrophysical, hydrophobic and spatial properties of the polypeptide chains constituting the binding groove. Thus one skilled in the art would be able to modify the amino acid sequences set forth in SEQ ID NO: 1 to 95, by maintaining the known anchor residues, and would be able to determine whether such variants maintain the ability to bind MHC class I or II molecules. The variants of the present invention retain the ability to bind to the TCR of activated CTL, which can subsequently cross-react with- and kill cells that express a polypeptide containing the natural amino acid sequence of the cognate peptide as defined in the aspects of the invention.

Those amino acid residues that do not substantially contribute to interactions with the T-cell receptor can be modified by replacement with another amino acid whose incorporation does not substantially affect T-cell reactivity and does not eliminate binding to the relevant MHC. Thus, apart from the proviso given, the peptide of the invention may be any peptide (by which term the inventors include oligopeptide or polypeptide), which includes the amino acid sequences or a portion or variant thereof as given.

TABLE 3

Variants and motif of the peptides according to SEQ ID NO: 1 to 33

| | | Position | | | | | | | | | |
|---|---|---|---|---|---|---|---|---|---|---|---|
| | | 1 | 2 | 3 | 4 | 5 | 6 | 7 | 8 | 9 | 10 |
| CDC2-001 | Peptide Code | L | Y | Q | I | L | Q | G | I | V | F |
| SEQ ID 1 | Variants | | F | | | | | | | | |
| | | | | | | | | | | L | |
| | | | | | | | | | | I | |
| | | | | | | F | | | | L | |
| | | | | | | F | | | | I | |
| ASPM-002 | Peptide Code | S | Y | N | P | L | W | L | R | I | |
| SEQ ID 2 | Variants | | F | | | | | | | | |
| | | | | | | | | | | L | |
| | | | | | | | | | | F | |
| | | | | | | F | | | | L | |
| | | | | | | F | | | | F | |
| UCHL5-001 | Peptide Code | N | Y | L | P | F | I | M | E | L | |

TABLE 3-continued

Variants and motif of the peptides according to SEQ ID NO: 1 to 33

| | | Position | | | | | | | | | |
|---|---|---|---|---|---|---|---|---|---|---|---|
| | | 1 | 2 | 3 | 4 | 5 | 6 | 7 | 8 | 9 | 10 |
| SEQ ID 3 | Variants | | F | | | | | | | | |
| | | | | | | | | | | F | |
| | | | | | | | | | | I | |
| | | | F | | | | | | | F | |
| | | | F | | | | | | | I | |
| MET-006 | Peptide Code | S | Y | I | D | V | L | P | E | F | |
| SEQ ID 4 | Variants | | F | | | | | | | | |
| | | | | | | | | | | L | |
| | | | | | | | | | | I | |
| | | | F | | | | | | | F | |
| | | | F | | | | | | | I | |
| PROM-001 | Peptide Code | S | Y | I | I | D | P | L | N | L | |
| SEQ ID 5 | Variants | | F | | | | | | | | |
| | | | | | | | | | | F | |
| | | | | | | | | | | I | |
| | | | F | | | | | | | F | |
| | | | F | | | | | | | I | |
| MMP11-001 | Peptide Code | V | W | S | D | V | T | P | L | T | F |
| SEQ ID 6 | Variants | | Y | | | | | | | | |
| | | | F | | | | | | | | |
| | | | | | | | | | | | L |
| | | | | | | | | | | | I |
| | | | Y | | | | | | | | L |
| | | | Y | | | | | | | | I |
| | | | F | | | | | | | | L |
| | | | F | | | | | | | | I |
| MST1R-001 | Peptide Code | N | Y | L | L | Y | V | S | N | F | |
| SEQ ID 7 | Variants | | F | | | | | | | | |
| | | | | | | | | | | L | |
| | | | | | | | | | | I | |
| | | | F | | | | | | | L | |
| | | | F | | | | | | | I | |
| NFYB-001 | Peptide Code | V | Y | T | T | S | Y | Q | Q | I | |
| SEQ ID 8 | Variants | | F | | | | | | | | |
| | | | | | | | | | | L | |
| | | | | | | | | | | F | |
| | | | F | | | | | | | L | |
| | | | F | | | | | | | F | |
| SMC4-001 | Peptide Code | H | Y | K | P | T | P | L | Y | F | |
| SEQ ID 9 | Variants | | F | | | | | | | | |
| | | | | | | | | | | L | |
| | | | | | | | | | | I | |
| | | | F | | | | | | | L | |
| | | | F | | | | | | | I | |
| UQCRB-001 | Peptide Code | Y | Y | N | A | A | G | F | N | K | L |
| SEQ ID 10 | Variants | | F | | | | | | | | |
| | | | | | | | | | | | F |
| | | | | | | | | | | | I |
| | | | F | | | | | | | | F |
| | | | F | | | | | | | | I |
| PPAP2C-001 | Peptide Code | A | Y | L | V | Y | T | D | R | L | |
| SEQ ID 11 | Variants | | F | | | | | | | | |
| | | | | | | | | | | F | |
| | | | | | | | | | | I | |
| | | | F | | | | | | | F | |
| | | | F | | | | | | | I | |
| AVL9-001 | Peptide Code | F | Y | I | S | P | V | N | K | L | |
| SEQ ID 12 | Variants | | F | | | | | | | | |
| | | | | | | | | | | F | |
| | | | | | | | | | | I | |
| | | | F | | | | | | | F | |
| | | | F | | | | | | | I | |
| NUF2-001 | Peptide Code | V | Y | G | I | R | L | E | H | F | |
| SEQ ID 13 | Variants | | F | | | | | | | | |
| | | | | | | | | | | L | |
| | | | | | | | | | | I | |
| | | | F | | | | | | | L | |
| | | | F | | | | | | | I | |
| ABL1-001 | Peptide Code | T | Y | G | N | L | L | D | Y | L | |
| SEQ ID 14 | Variants | | F | | | | | | | | |
| | | | | | | | | | | F | |
| | | | | | | | | | | I | |
| | | | F | | | | | | | F | |
| | | | F | | | | | | | I | |
| MUC-006 | Peptide Code | N | Y | E | E | T | F | P | H | I | |
| SEQ ID 15 | Variants | | F | | | | | | | | |
| | | | | | | | | | | F | |
| | | | | | | | | | | L | |
| | | | F | | | | | | | F | |
| | | | F | | | | | | | L | |
| ASPM-001 | Peptide Code | R | Y | L | W | A | T | V | T | I | |
| SEQ ID 16 | Variants | | F | | | | | | | | |
| | | | | | | | | | | F | |
| | | | | | | | | | | L | |
| | | | F | | | | | | | F | |
| | | | F | | | | | | | L | |
| EPHA2-005 | Peptide Code | V | Y | F | S | K | S | E | Q | L | |
| SEQ ID 17 | Variants | | F | | | | | | | | |
| | | | | | | | | | | F | |
| | | | | | | | | | | I | |
| | | | F | | | | | | | F | |
| | | | F | | | | | | | I | |
| MMP3-001 | Peptide Code | V | F | I | F | K | G | N | Q | F | |
| SEQ ID 18 | Variants | | Y | | | | | | | | |
| | | | | | | | | | | L | |
| | | | | | | | | | | I | |
| | | | Y | | | | | | | L | |
| | | | Y | | | | | | | I | |
| NUF2-002 | Peptide Code | R | F | L | S | G | I | I | N | F | |
| SEQ ID 19 | Variants | | Y | | | | | | | | |
| | | | | | | | | | | L | |
| | | | | | | | | | | I | |
| | | | Y | | | | | | | L | |
| | | | Y | | | | | | | I | |
| PLK4-001 | Peptide Code | Q | Y | A | S | R | F | V | Q | L | |
| SEQ ID 20 | Variants | | F | | | | | | | | |
| | | | | | | | | | | F | |
| | | | | | | | | | | I | |
| | | | F | | | | | | | F | |
| | | | F | | | | | | | I | |
| ATAD2-002 | Peptide Code | K | Y | L | T | V | K | D | Y | L | |
| SEQ ID 21 | Variants | | F | | | | | | | | |
| | | | | | | | | | | F | |
| | | | | | | | | | | I | |
| | | | F | | | | | | | F | |
| | | | F | | | | | | | I | |
| COL12A1-001 | Peptide Code | V | Y | N | P | T | P | N | S | L | |
| SEQ ID 22 | Variants | | F | | | | | | | | |
| | | | | | | | | | | F | |
| | | | | | | | | | | I | |
| | | | F | | | | | | | F | |
| | | | F | | | | | | | I | |
| COL6A3-001 | Peptide Code | S | Y | L | Q | A | A | N | A | L | |

TABLE 3-continued

Variants and motif of the peptides according to SEQ ID NO: 1 to 33

| | | Position | | | | | | | | | |
|---|---|---|---|---|---|---|---|---|---|---|---|
| | | 1 | 2 | 3 | 4 | 5 | 6 | 7 | 8 | 9 | 10 |
| SEQ ID 23 | Variants | | F | | | | | | | | |
| | | | | | | | | | | F | |
| | | | | | | | | | | I | |
| | | | F | | | | | | | F | |
| | | | F | | | | | | | I | |
| FANCI-001 | Peptide Code | F | Y | Q | P | K | I | Q | Q | F | |
| SEQ ID 24 | Variants | | F | | | | | | | | |
| | | | | | | | | | | L | |
| | | | | | | | | | | I | |
| | | | F | | | | | | | L | |
| | | | F | | | | | | | I | |
| RSP11-001 | Peptide Code | Y | Y | K | N | I | G | L | G | F | |
| SEQ ID 25 | Variants | | F | | | | | | | | |
| | | | | | | | | | | L | |
| | | | | | | | | | | I | |
| | | | F | | | | | | | L | |
| | | | F | | | | | | | I | |
| ATAD2-001 | Peptide Code | A | Y | A | I | I | K | E | E | L | |
| SEQ ID 26 | Variants | | F | | | | | | | | |
| | | | | | | | | | | F | |
| | | | | | | | | | | I | |
| | | | F | | | | | | | F | |
| | | | F | | | | | | | I | |
| ATAD2-003 | Peptide Code | L | Y | P | E | V | F | E | K | F | |
| SEQ ID 27 | Variants | | F | | | | | | | | |
| | | | | | | | | | | L | |
| | | | | | | | | | | I | |
| | | | F | | | | | | | L | |
| | | | F | | | | | | | I | |
| HSP90B1-001 | Peptide Code | K | Y | N | D | T | F | W | K | E | F |
| SEQ ID 28 | Variants | | F | | | | | | | | |
| | | | | | | | | | | | L |
| | | | | | | | | | | | I |
| | | | F | | | | | | | | L |
| | | | F | | | | | | | | I |
| SIAH2-001 | Peptide Code | V | F | D | T | A | I | A | H | L | F |
| SEQ ID 29 | Variants | | Y | | | | | | | | |
| | | | | | | | | | | L | |
| | | | | | | | | | | I | |
| | | | Y | | | | | | | L | |
| | | | Y | | | | | | | I | |
| SLC6A6-001 | Peptide Code | V | Y | P | N | W | A | I | G | L | |
| SEQ ID 30 | Variants | | F | | | | | | | | |
| | | | | | | | | | | F | |
| | | | | | | | | | | I | |
| | | | F | | | | | | | F | |
| | | | F | | | | | | | I | |
| IQGAP3-001 | Peptide Code | V | Y | K | V | V | G | N | L | L | |
| SEQ ID 31 | Variants | | F | | | | | | | | |
| | | | | | | | | | | F | |
| | | | | | | | | | | I | |
| | | | F | | | | | | | F | |
| | | | F | | | | | | | I | |
| ERBB3-001 | Peptide Code | V | Y | I | E | K | N | D | K | L | |
| SEQ ID 32 | Variants | | F | | | | | | | | |
| | | | | | | | | | | F | |
| | | | | | | | | | | I | |
| | | | F | | | | | | | F | |
| | | | F | | | | | | | I | |
| KIF2C-001 | Peptide Code | I | Y | N | G | K | L | F | D | L | L |
| SEQ ID 33 | Variants | | F | | | | | | | | |
| | | | | | | | | | | | F |
| | | | | | | | | | | | I |
| | | | F | | | | | | | | F |
| | | | F | | | | | | | | I |
| CDC2-001 | Peptide Code | L | Y | Q | I | L | Q | G | I | V | F |
| SEQ ID 1 | Variants | | F | | | | | | | | |
| | | | | | | | | | | L | |
| | | | | | | | | | | I | |
| | | | F | | | | | | | L | |
| | | | F | | | | | | | I | |
| ASPM-002 | Peptide Code | S | Y | N | P | L | W | L | R | I | |
| SEQ ID 2 | Variants | | F | | | | | | | | |
| | | | | | | | | | | L | |
| | | | | | | | | | | F | |
| | | | F | | | | | | | L | |
| | | | F | | | | | | | F | |
| UCHL5-001 | Peptide Code | N | Y | L | P | F | I | M | E | L | |
| SEQ ID 3 | Variants | | F | | | | | | | | |
| | | | | | | | | | | F | |
| | | | | | | | | | | I | |
| | | | F | | | | | | | F | |
| | | | F | | | | | | | I | |
| MET-006 | Peptide Code | S | Y | I | D | V | L | P | E | F | |
| SEQ ID 4 | Variants | | F | | | | | | | | |
| | | | | | | | | | | L | |
| | | | | | | | | | | I | |
| | | | F | | | | | | | F | |
| | | | F | | | | | | | I | |
| PROM-001 | Peptide Code | S | Y | I | I | D | P | L | N | L | |
| SEQ ID 5 | Variants | | F | | | | | | | | |
| | | | | | | | | | | | F |
| | | | | | | | | | | | I |
| | | | F | | | | | | | | F |
| | | | F | | | | | | | | I |
| MMP11-001 | Peptide Code | V | W | S | D | V | T | P | L | T | F |
| SEQ ID 6 | Variants | | Y | | | | | | | | |
| | | | F | | | | | | | | |
| | | | | | | | | | | L | |
| | | | | | | | | | | I | |
| | | | Y | | | | | | | L | |
| | | | Y | | | | | | | I | |
| | | | F | | | | | | | L | |
| | | | F | | | | | | | I | |
| MST1R-001 | Peptide Code | N | Y | L | L | Y | V | S | N | F | |
| SEQ ID 7 | Variants | | F | | | | | | | | |
| | | | | | | | | | | L | |
| | | | | | | | | | | I | |
| | | | F | | | | | | | L | |
| | | | F | | | | | | | I | |
| NFYB-001 | Peptide Code | V | Y | T | T | S | Y | Q | Q | I | |
| SEQ ID 8 | Variants | | F | | | | | | | | |
| | | | | | | | | | | L | |
| | | | | | | | | | | F | |
| | | | F | | | | | | | L | |
| | | | F | | | | | | | F | |
| SMC4-001 | Peptide Code | H | Y | K | P | T | P | L | Y | F | |
| SEQ ID 9 | Variants | | F | | | | | | | | |
| | | | | | | | | | | L | |
| | | | | | | | | | | I | |
| | | | F | | | | | | | L | |
| | | | F | | | | | | | I | |
| UQCRB-001 | Peptide Code | Y | Y | N | A | A | G | F | N | K | L |

TABLE 3-continued

Variants and motif of the peptides according to SEQ ID NO: 1 to 33

| | | Position 1 | 2 | 3 | 4 | 5 | 6 | 7 | 8 | 9 | 10 |
|---|---|---|---|---|---|---|---|---|---|---|---|
| SEQ ID 10 | Variants | | F | | | | | | | | |
| | | | | | | | | | | | F |
| | | | | | | | | | | | I |
| | | | F | | | | | | | | F |
| | | | F | | | | | | | | I |
| PPAP2C-001 | Peptide Code | A | Y | L | V | Y | T | D | R | L | |
| SEQ ID 11 | Variants | | F | | | | | | | | |
| | | | | | | | | | | F | |
| | | | | | | | | | | I | |
| | | | F | | | | | | | F | |
| | | | F | | | | | | | I | |
| AVL9-001 | Peptide Code | F | Y | I | S | P | V | N | K | L | |
| SEQ ID 12 | Variants | | F | | | | | | | | |
| | | | | | | | | | | F | |
| | | | | | | | | | | I | |
| | | | F | | | | | | | F | |
| | | | F | | | | | | | I | |
| NUF2-001 | Peptide Code | V | Y | G | I | R | L | E | H | F | |
| SEQ ID 13 | Variants | | F | | | | | | | | |
| | | | | | | | | | | L | |
| | | | | | | | | | | I | |
| | | | F | | | | | | | L | |
| | | | F | | | | | | | I | |
| ABL1-001 | Peptide Code | T | Y | G | N | L | L | D | Y | L | |
| SEQ ID 14 | Variants | | F | | | | | | | | |
| | | | | | | | | | | F | |
| | | | | | | | | | | I | |
| | | | F | | | | | | | F | |
| | | | F | | | | | | | I | |
| MUC-006 | Peptide Code | N | Y | E | E | T | F | P | H | I | |
| SEQ ID 15 | Variants | | F | | | | | | | | |
| | | | | | | | | | | F | |
| | | | | | | | | | | L | |
| | | | F | | | | | | | F | |
| | | | F | | | | | | | L | |
| ASPM-001 | Peptide Code | R | Y | L | W | A | T | V | T | I | |
| SEQ ID 16 | Variants | | F | | | | | | | | |
| | | | | | | | | | | F | |
| | | | | | | | | | | L | |
| | | | F | | | | | | | F | |
| | | | F | | | | | | | L | |
| EPHA2-005 | Peptide Code | V | Y | F | S | K | S | E | Q | L | |
| SEQ ID 17 | Variants | | F | | | | | | | | |
| | | | | | | | | | | F | |
| | | | | | | | | | | I | |
| | | | F | | | | | | | F | |
| | | | F | | | | | | | I | |
| MMP3-001 | Peptide Code | V | F | I | F | K | G | N | Q | F | |
| SEQ ID 18 | Variants | | Y | | | | | | | | |
| | | | | | | | | | | L | |
| | | | | | | | | | | I | |
| | | | Y | | | | | | | L | |
| | | | Y | | | | | | | I | |
| NUF2-002 | Peptide Code | R | F | L | S | G | I | N | F | | |
| SEQ ID 19 | Variants | | Y | | | | | | | | |
| | | | | | | | | | | L | |
| | | | | | | | | | | I | |
| | | | Y | | | | | | | L | |
| | | | Y | | | | | | | I | |
| PLK4-001 | Peptide Code | Q | Y | A | S | R | F | V | Q | L | |
| SEQ ID 20 | Variants | | F | | | | | | | | |
| | | | | | | | | | | F | |
| | | | | | | | | | | I | |
| | | | F | | | | | | | F | |
| | | | F | | | | | | | I | |
| ATAD2-002 | Peptide Code | K | Y | L | T | V | K | D | Y | L | |
| SEQ ID 21 | Variants | | F | | | | | | | | |
| | | | | | | | | | | F | |
| | | | | | | | | | | I | |
| | | | F | | | | | | | F | |
| | | | F | | | | | | | I | |
| COL12A1-001 | Peptide Code | V | Y | N | P | T | P | N | S | L | |
| SEQ ID 22 | Variants | | F | | | | | | | | |
| | | | | | | | | | | F | |
| | | | | | | | | | | I | |
| | | | F | | | | | | | F | |
| | | | F | | | | | | | I | |
| COL6A3-001 | Peptide Code | S | Y | L | Q | A | A | N | A | L | |
| SEQ ID 23 | Variants | | F | | | | | | | | |
| | | | | | | | | | | F | |
| | | | | | | | | | | I | |
| | | | F | | | | | | | F | |
| | | | F | | | | | | | I | |
| FANCI-001 | Peptide Code | F | Y | Q | P | K | I | Q | Q | F | |
| SEQ ID 24 | Variants | | F | | | | | | | | |
| | | | | | | | | | | L | |
| | | | | | | | | | | I | |
| | | | F | | | | | | | L | |
| | | | F | | | | | | | I | |
| RSP11-001 | Peptide Code | Y | Y | K | N | I | G | L | G | F | |
| SEQ ID 25 | Variants | | F | | | | | | | | |
| | | | | | | | | | | L | |
| | | | | | | | | | | I | |
| | | | F | | | | | | | L | |
| | | | F | | | | | | | I | |
| ATAD2-001 | Peptide Code | A | Y | A | I | K | E | E | L | | |
| SEQ ID 26 | Variants | | F | | | | | | | | |
| | | | | | | | | | | F | |
| | | | | | | | | | | I | |
| | | | F | | | | | | | F | |
| | | | F | | | | | | | I | |
| ATAD2-003 | Peptide Code | L | Y | P | E | V | F | E | K | F | |
| SEQ ID 27 | Variants | | F | | | | | | | | |
| | | | | | | | | | | L | |
| | | | | | | | | | | I | |
| | | | F | | | | | | | L | |
| | | | F | | | | | | | I | |
| HSP90B1-001 | Peptide Code | K | Y | N | D | T | F | W | K | E | F |
| SEQ ID 28 | Variants | | F | | | | | | | | |
| | | | | | | | | | | | L |
| | | | | | | | | | | | I |
| | | | F | | | | | | | | L |
| | | | F | | | | | | | | I |
| SIAH2-001 | Peptide Code | V | F | D | T | A | I | A | H | L | F |
| SEQ ID 29 | Variants | | Y | | | | | | | | |
| | | | | | | | | | | | L |
| | | | | | | | | | | | I |
| | | | Y | | | | | | | | L |
| | | | Y | | | | | | | | I |
| SLC6A6-001 | Peptide Code | V | Y | P | N | W | A | I | G | L | |

TABLE 3-continued

Variants and motif of the peptides according to SEQ ID NO: 1 to 33

| | | Position | | | | | | | | | |
|---|---|---|---|---|---|---|---|---|---|---|---|
| | | 1 | 2 | 3 | 4 | 5 | 6 | 7 | 8 | 9 | 10 |
| SEQ ID 30 | Variants | | F | | | | | | | | |
| | | | | | | | | | | F | |
| | | | | | | | | | | I | |
| | | | F | | | | | | | F | |
| | | | F | | | | | | | I | |
| IQGAP3-001 | Peptide Code | V | Y | K | V | V | G | N | L | L | |
| SEQ ID 31 | Variants | | F | | | | | | | | |
| | | | | | | | | | | F | |
| | | | | | | | | | | I | |
| | | | F | | | | | | | F | |
| | | | F | | | | | | | I | |
| ERBB3-001 | Peptide Code | V | Y | I | E | K | N | D | K | L | |
| SEQ ID 32 | Variants | | F | | | | | | | | |
| | | | | | | | | | | F | |
| | | | | | | | | | | I | |
| | | | F | | | | | | | F | |
| | | | F | | | | | | | I | |
| KIF2C-001 | Peptide Code | I | Y | N | G | K | L | F | D | L | L |
| SEQ ID 33 | Variants | | F | | | | | | | | |
| | | | | | | | | | | | F |
| | | | | | | | | | | | I |
| | | | F | | | | | | | | F |
| | | | F | | | | | | | | I |

Longer peptides may also be suitable. It is also possible, that MHC class I epitopes, although usually from 8 to 11 amino acids long, are generated by peptide processing from longer peptides or proteins that include the actual epitope. It is preferred that the residues that flank the actual epitope are residues that do not substantially affect proteolytic cleavage necessary to expose the actual epitope during processing.

Accordingly, the present invention also provides peptides and variants of MHC class I epitopes wherein the peptide or variant has an overall length of not more than 100, not more than 30, and most preferred from 8 to 14, namely 8, 9, 10, 11, 12, 13, 14 amino acids.

Of course, the peptide or variant according to the present invention will have the ability to bind to a molecule of the human major histocompatibility complex (MHC) class I. Binding of a peptide or a variant to a MHC complex may be tested by methods known in the art.

In a particularly preferred embodiment of the invention the peptide consists or consists essentially of an amino acid sequence according to SEQ ID NO: 1 to SEQ ID NO: 95.

"Consisting essentially of" shall mean that a peptide according to the present invention, in addition to the sequence according to any of SEQ ID NO: 1 to SEQ ID NO: 95 or a variant thereof contains additional N- and/or C-terminally located stretches of amino acids that are not necessarily forming part of the peptide that functions as an epitope for MHC molecules epitope.

Nevertheless, these stretches can be important to provide an efficient introduction of the peptide according to the present invention into the cells. In one embodiment of the present invention, the peptide is a fusion protein which comprises, for example, the 80 N-terminal amino acids of the HLA-DR antigen-associated invariant chain (p33, in the following "Ii") as derived from the NCBI, GenBank Accession number X00497.

In addition, the peptide or variant may be modified further to improve stability and/or binding to MHC molecules in order to elicit a stronger immune response. Methods for such an optimization of a peptide sequence are well known in the art and include, for example, the introduction of reverse peptide bonds or non-peptide bonds.

In a reverse peptide bond amino acid residues are not joined by peptide (—CO—NH—) linkages but the peptide bond is reversed. Such retro-inverso peptidomimetics may be made using methods known in the art, for example such as those described in Meziere et al (1997) J. Immunol. 159, 3230-3237, incorporated herein by reference. This approach involves making pseudopeptides containing changes involving the backbone, and not the orientation of side chains. Meziere et al (1997) show that for MHC binding and T helper cell responses, these pseudopeptides are useful. Retro-inverse peptides, which contain NH—CO bonds instead of CO—NH peptide bonds, are much more resistant to proteolysis.

A non-peptide bond is, for example, —CH2-NH, —CH2S—, —CH2CH2-, —CH=CH—, —COCH2-, —CH(OH)CH2-, and —CH2SO—. U.S. Pat. No. 4,897,445 provides a method for the solid phase synthesis of non-peptide bonds (—CH2-NH) in polypeptide chains which involves polypeptides synthesized by standard procedures and the non-peptide bond synthesized by reacting an amino aldehyde and an amino acid in the presence of NaCNBH3.

Peptides comprising the sequences described above may be synthesized with additional chemical groups present at their amino and/or carboxy termini, to enhance the stability, bioavailability, and/or affinity of the peptides. For example, hydrophobic groups such as carbobenzoxyl, dansyl, or t-butyloxycarbonyl groups may be added to the peptides' amino termini. Likewise, an acetyl group or a 9-fluorenylmethoxy-carbonyl group may be placed at the peptides' amino termini. Additionally, the hydrophobic group, t-butyloxycarbonyl, or an amido group may be added to the peptides' carboxy termini.

Further, the peptides of the invention may be synthesized to alter their steric configuration. For example, the D-isomer of one or more of the amino acid residues of the peptide may be used, rather than the usual L-isomer. Still further, at least one of the amino acid residues of the peptides of the invention may be substituted by one of the well known non-naturally occurring amino acid residues. Alterations such as these may serve to increase the stability, bioavailability and/or binding action of the peptides of the invention.

Similarly, a peptide or variant of the invention may be modified chemically by reacting specific amino acids either before or after synthesis of the peptide. Examples for such modifications are well known in the art and are summarized e.g. in R. Lundblad, Chemical Reagents for Protein Modification, 3rd ed. CRC Press, 2005, which is incorporated herein by reference. Chemical modification of amino acids includes but is not limited to, modification by acylation, amidination, pyridoxylation of lysine, reductive alkylation, trinitrobenzylation of amino groups with 2,4,6-trinitrobenzene sulphonic acid (TNBS), amide modification of carboxyl groups and sulphydryl modification by performic acid oxidation of cysteine to cysteic acid, formation of mercurial derivatives, formation of mixed disulphides with other thiol compounds, reaction with maleimide, carboxymethylation with iodoacetic acid or iodoacetamide and carbamoylation with cyanate at alkaline pH, although without limitation thereto. In this regard, the skilled person is referred to Chapter 15 of Current Protocols In Protein Science, Eds. Coligan et al. (John Wiley and Sons NY 1995-2000) for more extensive methodology relating to chemical modification of proteins.

Briefly, modification of e.g. arginyl residues in proteins is often based on the reaction of vicinal dicarbonyl compounds such as phenylglyoxal, 2,3-butanedione, and 1,2-cyclohexanedione to form an adduct. Another example is the reaction of methylglyoxal with arginine residues. Cysteine can be modified without concomitant modification of other nucleophilic sites such as lysine and histidine. As a result, a large number of reagents are available for the modification of cysteine. The websites of companies such as Sigma-Aldrich (http://www.sigma-aldrich.com) provide information on specific reagents.

Selective reduction of disulfide bonds in proteins is also common. Disulfide bonds can be formed and oxidized during the heat treatment of biopharmaceuticals.

Woodward's Reagent K may be used to modify specific glutamic acid residues. N-(3-(dimethylamino)propyl)-N'-ethylcarbodiimide can be used to form intra-molecular crosslinks between a lysine residue and a glutamic acid residue.

For example, diethylpyrocarbonate is a reagent for the modification of histidyl residues in proteins. Histidine can also be modified using 4-hydroxy-2-nonenal.

The reaction of lysine residues and other α-amino groups is, for example, useful in binding of peptides to surfaces or the cross-linking of proteins/peptides. Lysine is the site of attachment of poly(ethylene)glycol and the major site of modification in the glycosylation of proteins.

Methionine residues in proteins can be modified with e.g. iodoacetamide, bromoethylamine, and chloramine T.

Tetranitromethane and N-acetylimidazole can be used for the modification of tyrosyl residues. Cross-linking via the formation of dityrosine can be accomplished with hydrogen peroxide/copper ions.

Recent studies on the modification of tryptophan have used N-bromosuccinimide, 2-hydroxy-5-nitrobenzyl bromide or 3-bromo-3-methyl-2-(2-nitrophenylmercapto)-3H-indole (BPNS-skatole).

Successful modification of therapeutic proteins and peptides with PEG is often associated with an extension of circulatory half-life while cross-linking of proteins with glutaraldehyde, polyethyleneglycol diacrylate and formaldehyde is used for the preparation of hydrogels. Chemical modification of allergens for immunotherapy is often achieved by carbamylation with potassium cyanate.

A peptide or variant, wherein the peptide is modified or includes non-peptide bonds is a preferred embodiment of the invention. Generally, peptides and variants (at least those containing peptide linkages between amino acid residues) may be synthesized by the Fmoc-polyamide mode of solid-phase peptide synthesis as disclosed by Lu et al (1981) and references therein. Temporary N-amino group protection is afforded by the 9-fluorenylmethyloxycarbonyl (Fmoc) group. Repetitive cleavage of this highly base-labile protecting group is done using 20% piperidine in N, N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalizing agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N, N-dicyclohexyl-carbodiimide/1hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used include ethandithiol, phenol, anisole and water, the exact choice depending on the constituent amino acids of the peptide being synthesized. Also a combination of solid phase and solution phase methodologies for the synthesis of peptides is possible (see, for example (Bruckdorfer, Marder, and Albericio 29-43) and the references as cited therein).

Trifluoroacetic acid is removed by evaporation in vacuo, with subsequent trituration with diethyl ether affording the crude peptide. Any scavengers present are removed by a simple extraction procedure which on lyophilisation of the aqueous phase affords the crude peptide free of scavengers. Reagents for peptide synthesis are generally available from e.g. Calbiochem-Novabiochem (UK) Ltd, Nottingham NG7 2QJ, UK.

Purification may be performed by any one, or a combination of, techniques such as re-crystallization, size exclusion chromatography, ion-exchange chromatography, hydrophobic interaction chromatography and (usually) reverse-phase high performance liquid chromatography using e.g. acetonitril/water gradient separation.

Analysis of peptides may be carried out using thin layer chromatography, electrophoresis, in particular capillary electrophoresis, solid phase extraction (CSPE), reverse-phase high performance liquid chromatography, amino-acid analysis after acid hydrolysis and by fast atom bombardment (FAB) mass spectrometric analysis, as well as MALDI and ESI-Q-TOF mass spectrometric analysis.

A further aspect of the invention provides a nucleic acid (for example a polynucleotide) encoding a peptide or peptide variant of the invention. The polynucleotide may be, for example, DNA, cDNA, PNA, CNA, RNA or combinations thereof, either single- and/or double-stranded, or native or stabilized forms of polynucleotides, such as, for example, polynucleotides with a phosphorothioate backbone and it may or may not contain introns so long as it codes for the peptide. Of course, only peptides that contain naturally occurring amino acid residues joined by naturally occurring peptide bonds are encodable by a polynucleotide. A still further aspect of the invention provides an expression vector capable of expressing a polypeptide according to the invention.

A variety of methods have been developed to link polynucleotides, especially DNA, to vectors for example via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. Synthetic linkers containing a variety of restriction endonuclease sites are commercially available from a number of sources including International Biotechnologies Inc, New Haven, Conn., USA.

A desirable method of modifying the DNA encoding the polypeptide of the invention employs the polymerase chain reaction as disclosed by (Saiki et al. 487-91)). This method may be used for introducing the DNA into a suitable vector, for example by engineering in suitable restriction sites, or it may be used to modify the DNA in other useful ways as is known in the art. If viral vectors are used, pox- or adenovirus vectors are preferred.

The DNA (or in the case of retroviral vectors, RNA) may then be expressed in a suitable host to produce a polypeptide comprising the peptide or variant of the invention. Thus, the DNA encoding the peptide or variant of the invention may be used in accordance with known techniques, appropriately modified in view of the teachings contained herein, to construct an expression vector, which is then used to transform an appropriate host cell for the expression and production of the polypeptide of the invention. Such techniques include those disclosed in U.S. Pat. Nos. 4,440,859, 4,530, 901, 4,582,800, 4,677,063, 4,678,751, 4,704,362, 4,710,463, 4,757,006, 4,766,075, and 4,810,648.

The DNA (or in the case of retroviral vectors, RNA) encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance.

Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example *Aspergillus* spec.), plant cells, animal cells and insect cells. Preferably, the system can be mammalian cells such as CHO cells available from the ATCC Cell Biology Collection.

A typical mammalian cell vector plasmid for constitutive expression comprises the CMV or SV40 promoter with a suitable poly A tail and a resistance marker, such as neomycin. One example is pSVL available from Pharmacia, Piscataway, N.J., USA. An example of an inducible mammalian expression vector is pMSG, also available from Pharmacia. Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (Ycps). CMV promoter-based vectors (for example from Sigma-Aldrich) provide transient or stable expression, cytoplasmic expression or secretion, and N-terminal or C-terminal tagging in various combinations of FLAG, 3×FLAG, c-myc or MAT. These fusion proteins allow for detection, purification and analysis of recombinant protein. Dual-tagged fusions provide flexibility in detection.

The strong human cytomegalovirus (CMV) promoter regulatory region drives constitutive protein expression levels as high as 1 mg/L in COS cells. For less potent cell lines, protein levels are typically ~0.1 mg/L. The presence of the SV40 replication origin will result in high levels of DNA replication in SV40 replication permissive COS cells. CMV vectors, for example, can contain the pMB1 (derivative of pBR322) origin for replication in bacterial cells, the b-lactamase gene for ampicillin resistance selection in bacteria, hGH polyA, and the fl origin. Vectors containing the pre-protrypsin leader (PPT) sequence can direct the secretion of FLAG fusion proteins into the culture medium for purification using ANTI-FLAG antibodies, resins, and plates. Other vectors and expression systems are well known in the art for use with a variety of host cells.

The present invention also relates to a host cell transformed with a polynucleotide vector construct of the present invention. The host cell can be either prokaryotic or eukaryotic. Bacterial cells may be preferred prokaryotic host cells in some circumstances and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human fibroblastic and colon cell lines. Yeast host cells include YPH499, YPH500 and YPH501, which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insect cells are Sf9 cells which can be transfected with baculovirus expression vectors. An overview regarding the choice of suitable host cells for expression can be found in, for example, the textbook of Paulina Balbás and Argelia Lorence "Methods in Molecular Biology Recombinant Gene Expression, Reviews and Protocols," Part One, Second Edition, ISBN 978-1-58829-262-9, and other literature known to the person of skill.

Transformation of appropriate cell hosts with a DNA construct of the present invention is accomplished by well known methods that typically depend on the type of vector used. With regard to transformation of prokaryotic host cells, see, for example, Cohen et al (1972) Proc. Natl. Acad. Sci. USA 69, 2110, and Sambrook et al (1989) Molecular Cloning, A Laboratory Manual, Cold Spring Harbor Laboratory, Cold Spring Harbor, N.Y. Transformation of yeast cells is described in Sherman et al (1986) Methods In Yeast Genetics, A Laboratory Manual, Cold Spring Harbor, N.Y. The method of Beggs (1978) Nature 275, 104-109 is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA. Electroporation is also useful for transforming and/or transfecting cells and is well known in the art for transforming yeast cell, bacterial cells, insect cells and vertebrate cells.

Successfully transformed cells, i.e. cells that contain a DNA construct of the present invention, can be identified by well known techniques such as PCR. Alternatively, the presence of the protein in the supernatant can be detected using antibodies.

It will be appreciated that certain host cells of the invention are useful in the preparation of the peptides of the invention, for example bacterial, yeast and insect cells. However, other host cells may be useful in certain therapeutic methods. For example, antigen-presenting cells, such as dendritic cells, may usefully be used to express the peptides of the invention such that they may be loaded into appropriate MHC molecules. Thus, the current invention provides a host cell comprising a nucleic acid or an expression vector according to the invention.

In a preferred embodiment the host cell is an antigen presenting cell, in particular a dendritic cell or antigen presenting cell. APCs loaded with a recombinant fusion protein containing prostatic acid phosphatase (PAP) are currently under investigation for the treatment of prostate cancer (Sipuleucel-T) (Rini et al. 67-74; Small et al. 3089-94).

A further aspect of the invention provides a method of producing a peptide or its variant, the method comprising culturing a host cell and isolating the peptide from the host cell or its culture medium.

In another embodiment the peptide, the nucleic acid or the expression vector of the invention are used in medicine. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. Preferred methods of peptide injection include s.c., i.d., i.p., i.m., and i.v. Preferred methods of DNA injection include i.d., i.m., s.c., i.p. and i.v. Doses of e.g. between 50 µg and 1.5 mg, preferably 125 µg to 500 µg, of peptide or DNA may be given and will depend on the respective peptide or DNA. Dosages of this range were successfully used in previous trials (Brunsvig et al. 1553-64; Staehler et al.).

Another aspect of the present invention includes an in vitro method for producing activated T cells, the method comprising contacting in vitro T cells with antigen loaded human MHC molecules expressed on the surface of a suitable antigen-presenting cell for a period of time sufficient to activate the T cell in an antigen specific manner, wherein the antigen is a peptide according to the invention. Preferably a sufficient amount of the antigen is used with an antigen-presenting cell.

Preferably the mammalian cell lacks or has a reduced level or function of the TAP peptide transporter. Suitable cells that lack the TAP peptide transporter include T2, RMA-S and Drosophila cells. TAP is the transporter associated with antigen processing.

The human peptide loading deficient cell line T2 is available from the American Type Culture Collection, 12301 Parklawn Drive, Rockville, Md. 20852, USA under Catalogue No CRL 1992; the Drosophila cell line Schneider line 2 is available from the ATCC under Catalogue No CRL 19863; the mouse RMA-S cell line is described in Kane et al 1985.

Preferably, the host cell before transfection expresses substantially no MHC class I molecules. It is also preferred that the stimulator cell expresses a molecule important for providing a co-stimulatory signal for T-cells such as any of B7.1, B7.2, ICAM-1 and LFA 3. The nucleic acid sequences of numerous MHC class I molecules and of the costimulator molecules are publicly available from the GenBank and EMBL databases.

In case of a MHC class I epitope being used as an antigen, the T cells are CD8-positive CTLs.

If an antigen-presenting cell is transfected to express such an epitope, preferably the cell comprises an expression vector capable of expressing a peptide containing SEQ ID NO: 1 to SEQ ID NO: 95 or a variant amino acid sequence thereof.

A number of other methods may be used for generating CTL in vitro. For example, the methods described in Peoples et al (1995) and Kawakami et al (1992) use autologous tumor-infiltrating lymphocytes in the generation of CTL. Plebanski et al (1995) makes use of autologous peripheral blood lymphocytes (PLBs) in the preparation of CTL. Jochmus et al (1997) describes the production of autologous CTL by pulsing dendritic cells with peptide or polypeptide, or via infection with recombinant virus. Hill et al (1995) and Jerome et al (1993) make use of B cells in the production of autologous CTL. In addition, macrophages pulsed with peptide or polypeptide, or infected with recombinant virus, may be used in the preparation of autologous CTL. S. Walter et al. 2003 describe the in vitro priming of T cells by using artificial antigen presenting cells (aAPCs), which is also a suitable way for generating T cells against the peptide of choice. In this study, aAPCs were generated by the coupling of preformed MHC:peptide complexes to the surface of polystyrene particles (microbeads) by biotin:streptavidin biochemistry. This system permits the exact control of the MHC density on aAPCs, which allows to selectively elicit high- or low-avidity antigen-specific T cell responses with high efficiency from blood samples. Apart from MHC: peptide complexes, aAPCs should carry other proteins with co-stimulatory activity like anti-CD28 antibodies coupled to their surface. Furthermore such aAPC-based systems often require the addition of appropriate soluble factors, e. g. cytokines like interleukin-12.

Allogeneic cells may also be used in the preparation of T cells and a method is described in detail in WO 97/26328, incorporated herein by reference. For example, in addition to Drosophila cells and T2 cells, other cells may be used to present antigens such as CHO cells, baculovirus-infected insect cells, bacteria, yeast, vaccinia-infected target cells. In addition plant viruses may be used (see, for example, Porta et al (1994)) which describes the development of cowpea mosaic virus as a high-yielding system for the presentation of foreign peptides.

The activated T cells that are directed against the peptides of the invention are useful in therapy. Thus, a further aspect of the invention provides activated T cells obtainable by the foregoing methods of the invention.

Activated T cells, which are produced by the above method, will selectively recognize a cell that aberrantly expresses a polypeptide that comprises an amino acid sequence of SEQ ID NO: 1 to 95.

Preferably, the T cell recognizes the cell by interacting through its TCR with the HLA/peptide-complex (for example, binding). The T cells are useful in a method of killing target cells in a patient whose target cells aberrantly express a polypeptide comprising an amino acid sequence of the invention wherein the patient is administered an effective number of the activated T cells. The T cells that are administered to the patient may be derived from the patient and activated as described above (i.e. they are autologous T cells). Alternatively, the T cells are not from the patient but are from another individual. Of course, it is preferred if the individual is a healthy individual. By "healthy individual" the inventors mean that the individual is generally in good health, preferably has a competent immune system and, more preferably, is not suffering from any disease which can be readily tested for, and detected.

In vivo, the target cells for the CD8-positive T cells according to the present invention can be cells of the tumor (which sometimes express MHC class I) and/or stromal cells surrounding the tumor (tumor cells) (which sometimes also express MHC class I; (Dengjel et al. 4163-70)).

The T cells of the present invention may be used as active ingredients of a therapeutic composition. Thus, the invention also provides a method of killing target cells in a patient whose target cells aberrantly express a polypeptide comprising an amino acid sequence of the invention, the method comprising administering to the patient an effective number of T cells as defined above.

By "aberrantly expressed" the inventors also mean that the polypeptide is over-expressed compared to normal levels of expression or that the gene is silent in the tissue from which the tumor is derived but in the tumor it is expressed. By "over-expressed" the inventors mean that the polypeptide is present at a level at least 1.2-fold of that present in normal tissue; preferably at least 2-fold, and more preferably at least 5-fold or 10-fold the level present in normal tissue.

T cells may be obtained by methods known in the art, e.g. those described above.

Protocols for this so-called adoptive transfer of T cells are well known in the art and can be found, e.g. in (Dudley et al. 850-54; Dudley et al. 2346-57; Rosenberg et al. 889-97; Rosenberg et al. 1676-80; Yee et al. 16168-73); reviewed in (Gattinoni et al. 383-93) and (Morgan et al.).

Any molecule of the invention, i.e. the peptide, nucleic acid, expression vector, cell, activated CTL, T-cell receptor or the nucleic acid encoding it is useful for the treatment of disorders, characterized by cells escaping an immune response. Therefore any molecule of the present invention may be used as medicament or in the manufacture of a medicament. The molecule may be used by itself or combined with other molecule(s) of the invention or (a) known molecule(s).

Preferably, the medicament of the present invention is a vaccine. It may be administered directly into the patient, into the affected organ or systemically i.d., i.m., s.c., i.p. and i.v., or applied ex vivo to cells derived from the patient or a human cell line which are subsequently administered to the patient, or used in vitro to select a subpopulation of immune cells derived from the patient, which are then re-administered to the patient. If the nucleic acid is administered to cells in vitro, it may be useful for the cells to be transfected so as to co-express immune-stimulating cytokines, such as interleukin-2. The peptide may be substantially pure, or combined with an immune-stimulating adjuvant (see below) or used in combination with immune-stimulatory cytokines, or be administered with a suitable delivery system, for example liposomes. The peptide may also be conjugated to a suitable carrier such as keyhole limpet haemocyanin (KLH) or mannan (see WO 95/18145 and Longenecker 1993). The peptide may also be tagged, may be a fusion protein, or may be a hybrid molecule. The peptides whose sequence is given in the present invention are expected to stimulate CD4 or CD8 T cells. However, stimulation of CD8 CTLs is more efficient in the presence of help provided by CD4 T-helper cells. Thus, for MHC Class I epitopes that stimulate CD8 CTL the fusion partner or sections of a hybrid molecule suitably provide epitopes which stimulate CD4-positive T cells. CD4- and CD8-stimulating epitopes are well known in the art and include those identified in the present invention.

In one aspect, the vaccine comprises at least one peptide having the amino acid sequence set forth in SEQ ID NO:1 to 33 and at least one additional peptide, preferably two to 50, more preferably two to 25, even more preferably two to 15 and most preferably two, three, four, five, six, seven, eight, nine, ten, eleven, twelve or thirteen peptides. The peptide(s) may be derived from one or more specific TAAs and may bind to MHC class I molecules.

The polynucleotide may be substantially pure, or contained in a suitable vector or delivery system. The nucleic acid may be DNA, cDNA, PNA, CNA, RNA or a combination thereof. Methods for designing and introducing such a nucleic acid are well known in the art. An overview is provided by e.g. (Pascolo et al. 117-22). Polynucleotide vaccines are easy to prepare, but the mode of action of these vectors in inducing an immune response is not fully understood. Suitable vectors and delivery systems include viral DNA and/or RNA, such as systems based on adenovirus, vaccinia virus, retroviruses, herpes virus, adeno-associated virus or hybrids containing elements of more than one virus. Non-viral delivery systems include cationic lipids and cationic polymers and are well known in the art of DNA delivery. Physical delivery, such as via a "gene-gun," may also be used. The peptide or peptides encoded by the nucleic acid may be a fusion protein, for example with an epitope that stimulates T cells for the respective opposite CDR as noted above.

The medicament of the invention may also include one or more adjuvants. Adjuvants are substances that non-specifically enhance or potentiate the immune response (e.g., immune responses mediated by CTLs and helper-T (TH) cells to an antigen, and would thus be considered useful in the medicament of the present invention. Suitable adjuvants include, but are not limited to, 1018 ISS, aluminium salts, Amplivax®, AS15, BCG, CP-870,893, CpG7909, CyaA, dSLIM, flagellin or TLR5 ligands derived from flagellin, FLT3 ligand, GM-CSF, IC30, IC31, Imiquimod (AL-DARA®), resiquimod, ImuFact IMP321, Interleukins as IL-2, IL-13, IL-21, Interferon-alpha or -beta, or pegylated derivatives thereof, IS Patch, ISS, ISCOMATRIX, ISCOMs, Juvlmmune, LipoVac, MALP2, MF59, monophosphoryl lipid A, Montanide IMS 1312, Montanide ISA 206, Montanide ISA 50V, Montanide ISA-51, water-in-oil and oil-in-water emulsions, OK-432, OM-174, OM-197-MP-EC, ONTAK, OspA, PepTel® vector system, poly(lactid co-glycolid) [PLG]-based and dextran microparticles, talactoferrin SRL172, Virosomes and other Virus-like particles, YF-17D, VEGF trap, R848, beta-glucan, Pam3Cys, Aquila's QS21 stimulon, which is derived from saponin, mycobacterial extracts and synthetic bacterial cell wall mimics, and other proprietary adjuvants such as Ribi's Detox, Quil, or Superfos. Adjuvants such as Freund's or GM-CSF are preferred. Several immunological adjuvants (e.g., MF59) specific for dendritic cells and their preparation have been described previously (Allison and Krummel 932-33). Also cytokines may be used. Several cytokines have been directly linked to influencing dendritic cell migration to lymphoid tissues (e.g., TNF-), accelerating the ☐ maturation of dendritic cells into efficient antigen-presenting cells for T-lymphocytes (e.g., GM-CSF, IL-1 and IL-4) (U.S. Pat. No.

5,849,589, specifically incorporated herein by reference in its entirety) and acting as immunoadjuvants (e.g., IL-12, IL-15, IL-23, IL-7, IFN-alpha. IFN-beta) [Gabrilovich 1996].

CpG immunostimulatory oligonucleotides have also been reported to enhance the effects of adjuvants in a vaccine setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly it enhances dendritic cell maturation and differentiation, resulting in enhanced activation of TH1 cells and strong cytotoxic T-lymphocyte (CTL) generation, even in the absence of CD4 T cell help. The TH1 bias induced by TLR9 stimulation is maintained even in the presence of vaccine adjuvants such as alum or incomplete Freund's adjuvant (IFA) that normally promote a TH2 bias. CpG oligonucleotides show even greater adjuvant activity when formulated or co-administered with other adjuvants or in formulations such as microparticles, nanoparticles, lipid emulsions or similar formulations, which are especially necessary for inducing a strong response when the antigen is relatively weak. They also accelerate the immune response and enable the antigen doses to be reduced by approximately two orders of magnitude, with comparable antibody responses to the full-dose vaccine without CpG in some experiments (Krieg 471-84). U.S. Pat. No. 6,406,705 B1 describes the combined use of CpG oligonucleotides, non-nucleic acid adjuvants and an antigen to induce an antigen-specific immune response. A CpG TLR9 antagonist is dSLIM (double Stem Loop Immunomodulator) by Mologen (Berlin, Germany) which is a preferred component of the pharmaceutical composition of the present invention. Other TLR binding molecules such as RNA binding TLR 7, TLR 8 and/or TLR 9 may also be used.

Other examples for useful adjuvants include, but are not limited to chemically modified CpGs (e.g. CpR, Idera), dsRNA analogues such as Poly(I:C) and derivates thereof (e.g. AmpliGen®, Hiltonol®, poly-(ICLC), poly(IC-R), poly(I:C12U), non-CpG bacterial DNA or RNA as well as immunoactive small molecules and antibodies such as cyclophosphamide, sunitinib, Bevacizumab, celebrex, NCX-4016, sildenafil, tadalafil, vardenafil, sorafenib, temozolomide, temsirolimus, XL-999, CP-547632, pazopanib, VEGF Trap, ZD2171, AZD2171, anti-CTLA4, other antibodies targeting key structures of the immune system (e.g. anti-CD40, anti-TGFbeta, anti-TNFalpha receptor) and SC58175, which may act therapeutically and/or as an adjuvant. The amounts and concentrations of adjuvants and additives useful in the context of the present invention can readily be determined by the skilled artisan without undue experimentation.

Preferred adjuvants are imiquimod, resiquimod, GM-CSF, cyclophosphamide, sunitinib, bevacizumab, interferon-alpha, CpG oligonucleotides and derivates, poly-(I:C) and derivates, RNA, sildenafil, and particulate formulations with PLG or virosomes.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), imiquimod, resiquimod, and interferon-alpha.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), immiquimod and resimiquimod.

In a preferred embodiment of the pharmaceutical composition according to the invention, the adjuvant is imiquimod or resiquimod.

This composition is used for parenteral administration, such as subcutaneous, intradermal, intramuscular or oral administration. For this, the peptides and optionally other molecules are dissolved or suspended in a pharmaceutically acceptable, preferably aqueous carrier. In addition, the composition can contain excipients, such as buffers, binding agents, blasting agents, diluents, flavours, lubricants, etc. The peptides can also be administered together with immune stimulating substances, such as cytokines. An extensive listing of excipients that can be used in such a composition, can be, for example, taken from A. Kibbe, Handbook of Pharmaceutical Excipients, 3. Ed. 2000, American Pharmaceutical Association and pharmaceutical press. The composition can be used for a prevention, prophylaxis and/or therapy of adenomateous or cancerous diseases. Examplary formulations can be found in EP2113253.

The present invention provides a medicament that useful in treating cancer, in particular gastric cancer, renal cell carcinoma, colon cancer, non-small cell lung carcinoma, adenocarcinoma, prostate cancer, benign neoplasm and malignant melanoma.

The present invention further includes a kit comprising:
(a) a container that contains a pharmaceutical composition as described above, in solution or in lyophilized form;
(b) optionally a second container containing a diluent or reconstituting solution for the lyophilized formulation; and
(c) optionally, instructions for (i) use of the solution or (ii) reconstitution and/or use of the lyophilized formulation.

The kit may further comprise one or more of (iii) a buffer, (iv) a diluent, (v) a filter, (vi) a needle, or (v) a syringe. The container is preferably a bottle, a vial, a syringe or test tube; and it may be a multi-use container. The pharmaceutical composition is preferably lyophilized.

Kits of the present invention preferably comprise a lyophilized formulation of the present invention in a suitable container and instructions for its reconstitution and/or use. Suitable containers include, for example, bottles, vials (e.g. dual chamber vials), syringes (such as dual chamber syringes) and test tubes. The container may be formed from a variety of materials such as glass or plastic. Preferably the kit and/or container contains instructions on or associated with the container that indicates directions for reconstitution and/or use. For example, the label may indicate that the lyophilized formulation is to be reconstituted to peptide concentrations as described above. The label may further indicate that the formulation is useful or intended for subcutaneous administration.

The container holding the formulation may be a multi-use vial, which allows for repeat administrations (e.g., from 2-6 administrations) of the reconstituted formulation. The kit may further comprise a second container comprising a suitable diluent (e.g., sodium bicarbonate solution).

Upon mixing of the diluent and the lyophilized formulation, the final peptide concentration in the reconstituted formulation is preferably at least 0.15 mg/mL/peptide (=75 µg) and preferably not more than 3 mg/mL/peptide (=1500 µg). The kit may further include other materials desirable from a commercial and user standpoint, including other buffers, diluents, filters, needles, syringes, and package inserts with instructions for use.

Kits of the present invention may have a single container that contains the formulation of the pharmaceutical compositions according to the present invention with or without other components (e.g., other compounds or pharmaceutical compositions of these other compounds) or may have distinct container for each component.

Preferably, kits of the invention include a formulation of the invention packaged for use in combination with the co-administration of a second compound (such as adjuvants (e.g. GM-CSF), a chemotherapeutic agent, a natural product, a hormone or antagonist, a anti-angiogenesis agent or inhibitor, a apoptosis-inducing agent or a chelator) or a pharmaceutical composition thereof. The components of the kit may be pre-complexed or each component may be in a separate distinct container prior to administration to a patient. The components of the kit may be provided in one or more liquid solutions, preferably, an aqueous solution, more preferably, a sterile aqueous solution. The components of the kit may also be provided as solids, which may be converted into liquids by addition of suitable solvents, which are preferably provided in another distinct container.

The container of a therapeutic kit may be a vial, test tube, flask, bottle, syringe, or any other means of enclosing a solid or liquid. Usually, when there is more than one component, the kit will contain a second vial or other container, which allows for separate dosing. The kit may also contain another container for a pharmaceutically acceptable liquid. Preferably, a therapeutic kit will contain an apparatus (e.g., one or more needles, syringes, eye droppers, pipette, etc.), which enables administration of the agents of the invention that are components of the present kit.

The present formulation is one that is suitable for administration of the peptides by any acceptable route such as oral (enteral), nasal, ophthal, subcutaneous, intradermal, intramuscular, intravenous or transdermal. Preferably the administration is s.c., and most preferably, i.d. Administration may be by infusion pump.

Since the peptides of the invention derived from MST1R, UCHL5, SMC4, NFYB, PPAP2C, AVL9, UQCRB and MUC6 were isolated from gastric cancer, the medicament of the invention is preferably used to treat gastric cancer.

The present invention will now be described in the following examples that describe preferred embodiments thereof, nevertheless, without being limited thereto. For the purposes of the present invention, all references as cited herein are incorporated by reference in their entireties.

EXAMPLES

Example 1

Identification of Tumor Associated Peptides Presented on Cell Surface
Tissue Samples Patients' tumor tissues were provided by Kyoto Prefectural University of Medicine (KPUM), Kyoto, Japan, Osaka City University Graduate School of Medicine (OCU), Osaka, Japan, and University Hospital Tubingen, Germany. Written informed consents of all patients had been given before surgery. Tissues were shock-frozen in liquid nitrogen immediately after surgery and stored until isolation of TUMAPs at −80° C.
Isolation of HLA Peptides from Tissue Samples HLA peptide pools from shock-frozen tissue samples were obtained by immune precipitation from solid tissues according to a slightly modified protocol (Falk, K. 1991; Seeger, F. H. T 1999} using the HLA-A, -B, -C-specific antibody W6/32, the HLA-A*02-specific antibody BB7.2, CNBr-activated sepharose, acid treatment, and ultrafiltration.
Methods The HLA peptide pools as obtained were separated according to their hydrophobicity by reversed-phase chromatography (nanoAcquity UPLC system, Waters) and the eluting peptides were analyzed in an LTQ-Orbitrap hybrid mass spectrometer (ThermoFisher Scientific) equipped with an ESI source. Peptide pools were loaded directly onto the analytical fused-silica micro-capillary column (75 µm i.d.× 250 mm) packed with 1.7 µm C18 reversed-phase material (Waters) applying a flow rate of 400 nL per minute. Subsequently, the peptides were separated using a two-step 180 minute-binary gradient from 10% to 33% B at a flow rate of 300 nL per minute. The gradient was composed of Solvent A (0.1% formic acid in water) and solvent B (0.1% formic acid in acetonitrile). A gold coated glass capillary (PicoTip, New Objective) was used for introduction into the nanoESI source. The LTQ-Orbitrap mass spectrometer was operated in the data-dependent mode using a TOPS strategy. In brief, a scan cycle was initiated with a full scan of high mass accuracy in the orbitrap (R=30 000), which was followed by MS/MS scans also in the orbitrap (R=7500) on the 5 most abundant precursor ions with dynamic exclusion of previously selected ions. Tandem mass spectra were interpreted by SEQUEST and additional manual control. The identified peptide sequence was assured by comparison of the generated natural peptide fragmentation pattern with the fragmentation pattern of a synthetic sequence-identical reference peptide. FIG. 1 shows an exemplary spectrum obtained from tumor tissue for the MHC class I associated peptide CDC2-001 and its elution profile on the UPLC system.

Example 2

Expression Profiling of Genes Encoding the Peptides of the Invention

Not all peptides identified as being presented on the surface of tumor cells by MHC molecules are suitable for immunotherapy, because the majority of these peptides are derived from normal cellular proteins expressed by many cell types. Only few of these peptides are tumor-associated and likely able to induce T cells with a high specificity of recognition for the tumor from which they were derived. In order to identify such peptides and minimize the risk for autoimmunity induced by vaccination the inventors focused on those peptides that are derived from proteins that are over-expressed on tumor cells compared to the majority of normal tissues.

The ideal peptide will be derived from a protein that is unique to the tumor and not present in any other tissue. To identify peptides that are derived from genes with an expression profile similar to the ideal one the identified peptides were assigned to the proteins and genes, respectively, from which they were derived and expression profiles of these genes were generated.
RNA Sources and Preparation Surgically removed tissue specimens were provided by different clinical sites (see Example 1) after written informed consent had been obtained from each patient. Tumor tissue specimens were snap-frozen in liquid nitrogen immediately after surgery and later homogenized with mortar and pestle under liquid nitrogen. Total RNA was prepared from these samples using TRI Reagent (Ambion, Darmstadt, Germany) followed by a cleanup with RNeasy (QIAGEN, Hilden, Germany); both methods were performed according to the manufacturer's protocol.

Total RNA from healthy human tissues was obtained commercially (Ambion, Huntingdon, UK; Clontech, Heidelberg, Germany; Stratagene, Amsterdam, Netherlands; BioChain, Hayward, Calif., USA). The RNA from several individuals (between 2 and 123 individuals) was mixed such that RNA from each individual was equally weighted. Leukocytes were isolated from blood samples of 4 healthy volunteers.

Quality and quantity of all RNA samples were assessed on an Agilent 2100 Bioanalyzer (Agilent, Waldbronn, Germany) using the RNA 6000 Pico LabChip Kit (Agilent).

Microarray Experiments

Gene expression analysis of all tumor and normal tissue RNA samples was performed by Affymetrix Human Genome (HG) U133A or HG-U133 Plus 2.0 oligonucleotide microarrays (Affymetrix, Santa Clara, Calif., USA). All steps were carried out according to the Affymetrix manual. Briefly, double-stranded cDNA was synthesized from 5-8 µg of total RNA, using SuperScript RTII (Invitrogen) and the oligo-dT-T7 primer (MWG Biotech, Ebersberg, Germany) as described in the manual. In vitro transcription was performed with the BioArray High Yield RNA Transcript Labelling Kit (ENZO Diagnostics, Inc., Farmingdale, N.Y., USA) for the U133A arrays or with the GeneChip IVT Labelling Kit (Affymetrix) for the U133 Plus 2.0 arrays, followed by cRNA fragmentation, hybridization, and staining with streptavidin-phycoerythrin and biotinylated anti-streptavidin antibody (Molecular Probes, Leiden, Netherlands). Images were scanned with the Agilent 2500A GeneArray Scanner (U133A) or the Affymetrix Gene-Chip Scanner 3000 (U133 Plus 2.0), and data were analyzed with the GCOS software (Affymetrix), using default settings for all parameters. For normalisation, 100 housekeeping genes provided by Affymetrix were used. Relative expression values were calculated from the signal log ratios given by the software and the normal kidney sample was arbitrarily set to 1.0.

Figure 2:
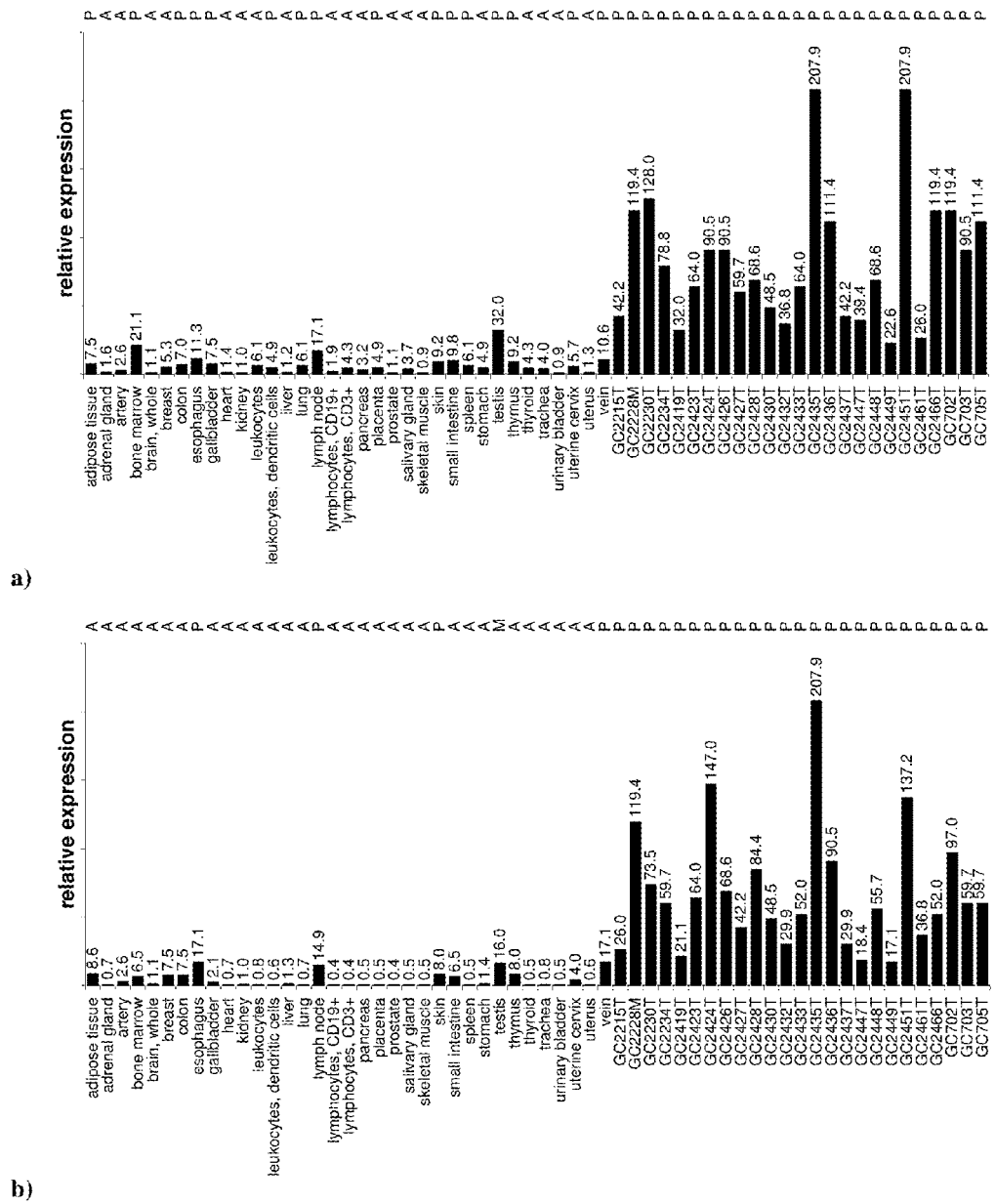
FIG. 2: Expression profiles of mRNA of selected proteins in normal tissues and in 25 gastric cancer samples
a) CDC2 (Probeset ID: 203213_at)
b) ASPM (Probeset ID: 219918_s_at)

The expression profiles of source genes of the present invention that are highly over-expressed in gastric cancer are shown in FIG. 2.

Example 3

In Vitro Immunogenicity for IMA941 MHC Class I Presented Peptides

In order to obtain information regarding the immunogenicity of the TUMAPs of the present invention, we performed investigations using a well established in vitro stimulation platform already described by (Walter, S, Herrgen, L, Schoor, O, Jung, G, Wernet, D, Buhring, H J, Rammensee, H G, and Stevanovic, S; 2003, Cutting edge: predetermined avidity of human CD8 T cells expanded on calibrated MHC/anti-CD28-coated microspheres, J. Immunol., 171, 4974-4978). With this system we could show positive immunogenicity (i. e. expansion of specific T cells) results for 47 of 54 tested HLA-A*2402 restricted TUMAPs and for 3 of 3 tested HLA-A*0201 restricted TUMAPs of the invention, demonstrating that these peptides are T-cell epitopes against which CD8+ precursor T cells exist in humans (Table 4).

In Vitro Priming of CD8+ T Cells

In order to perform in vitro stimulations by artificial antigen presenting cells (aAPC) loaded with peptide-MHC complex (pMHC) and anti-CD28 antibody, we first isolated CD8 T cells from fresh HLA-A*24 leukapheresis products or from HLA-A*2 buffy coats of healthy donors obtained from the Blood Bank Tuebingen.

CD8 T cells were either directly enriched or PBMCs (peripheral blood mononuclear cells) were isolated first by using standard gradient separation medium (PAA, Cölbe, Germany). Isolated CD8 lymphocytes or PBMCs were incubated until use in T-cell medium (TCM) consisting of RPMI-Glutamax (Invitrogen, Karlsruhe, Germany) supplemented with 10% heat inactivated human AB serum (PAN-Biotech, Aidenbach, Germany), 100 U/ml Penicillin/100 µg/ml Streptomycin (Cambrex, Cologne, Germany), 1 mM sodium pyruvate (CC Pro, Oberdorla, Germany), 20 µg/ml Gentamycin (Cambrex). 2.5 ng/ml IL-7 (PromoCell, Heidelberg, Germany) and 10 U/ml IL-2 (Novartis Pharma, Nürnberg, Germany) cytokines were added to the TCM for this culture step. Isolation of CD8+ lymphocytes was performed by positive selection using CD8 MicroBeads (Miltenyi Biotec, Bergisch-Gladbach, Germany).

Generation of pMHC/anti-CD28 coated beads, T-cell stimulations and readout was performed as described before (Walter et al. 4974-78) with minor modifications. Briefly, biotinylated peptide-loaded recombinant HLA-A*2402 and HLA-A*0201 molecules lacking the transmembrane domain and biotinylated at the carboxy terminus of the heavy chain were produced. The purified costimulatory mouse IgG2a anti human CD28 Ab 9.3 (Jung, Ledbetter, and Muller-Eberhard 4611-15) was chemically biotinylated using Sulfo-N-hydroxysuccinimidobiotin as recommended by the manufacturer (Perbio, Bonn, Germany). Beads used were 5.6 µm large streptavidin coated polystyrene particles (Bangs Laboratories, Illinois, USA). pMHC used as high and low immunogenic controls were A*0201/MLA-001 (peptide ELAGIGILTV from modified Melan-A/MART-1) and A*0201/DDX5-001 (YLLPAIVHI from DDX5), respectively.

800.000 beads/200 µl were coated in 96-well plates in the presence of 600 ng biotin-anti-CD28 plus 200 ng relevant biotin-pMHC (high density beads). Stimulations were initiated in 96-well plates by co-nincubating 1×106 CD8+ T cells with 2×105 washed coated beads in 200 µl TCM supplemented with 5 ng/ml IL-12 (PromoCell) for 3-4 days at 37° C., 5% CO2 and 95% relative humidity. Half of the medium was then exchanged by fresh TCM supplemented with 80 U/ml IL-2 and incubation was continued for 3-4 days at 37° C. This stimulation cycle was performed for a total of three times.

Finally, multimer analyses were performed by staining cells with fluorescent A*0201 or A*2402 HLA multimers (produced as described by {Altman, 1996 ALTMAN1996/id}) and CD8-FITC antibody clone SK1 (BD, Heidelberg, Germany) or additionally with a viability marker (Live/dead-Aqua or -Violet dye (Invitrogen, Karlsruhe, Germany)), and were conducted on a four-color FACSCalibur (BD) or a LSRII SORP cytometer (BD; eighteen color, equipped with a blue (488 nm), violet (405 nm), red (640 nm) and green (532 nm), respectively. Peptide specific cells were calculated as percentage of total CD8+ T cells. Evaluation of multimer analysis was done using the FCSExpress or FlowJo software (Tree Star, Oregon, USA). In vitro priming of specific multimer+ CD8+ lymphocytes was detected by appropriate gating and by comparing to negative control stimulations. Immunogenicity for a given antigen was detected if at least one evaluable in vitro stimulated well of one healthy donor was found to contain specific CD8+ T-cells after in vitro stimulation (i.e. the fraction of multimer+ cell population within this well constituted at least 1% of the CD8+ cells, the frequency was at least 10-fold over the median of the respective negative controls (stimulation with irrelevant and staining with relevant multimer) and the cells were not located on the diagonal of the plot).

In Vitro Immunogenicity for IMA941 Peptides

For 47 of 54 tested HLA-A*2402 peptides and for 3 of 3 tested HLA-A*0201 peptides, in vitro immunogenicity could be demonstrated by generation of peptide specific T-cell lines. Exemplary flow cytometry results after TUMAP-specific multimer staining for two peptides of the invention are shown in FIG. 3 together with a corresponding negative control. Results for 54 A*2402 and 3 A*0201 peptides of the invention are summarized in Table 4.

TABLE 4

In vitro immunogenicity of HLA class I peptides of the invention Results of in vitro immunogenicity experiments conducted by Immatics are showing the percentage of positive tested donors and wells among evaluable. At least four donors and 48 wells were evaluable for each peptide.

| SEQ ID NO: | Antigen | Donors positive/evaluable [%] | Wells positive/evaluable [%] |
|---|---|---|---|
| 1 | CDC2-001 | 83 | 28 |
| 2 | ASPM-002 | 67 | 32 |
| 18 | MMP3-001 | 11 | 1 |
| 4 | MET-006 | 67 | 21 |
| 3 | UCHL5-001 | 75 | 12 |
| 7 | MST1R-001 | 50 | 13 |
| 33 | KIF2C-001 | 17 | 2 |
| 9 | SMC4-001 | 73 | 10 |
| 17 | EPHA2-005 | 0 | 0 |
| 5 | PROM1-001 | 83 | 26 |
| 6 | MMP11-001 | 33 | 11 |
| 8 | NFYB-001 | 50 | 7 |
| 16 | ASPM-001 | 17 | 3 |
| 20 | PLK4-001 | 60 | 5 |
| 14 | ABL1-001 | 83 | 18 |
| 26 | ATAD2-001 | 33 | 3 |
| 21 | ATAD2-002 | 17 | 1 |
| 27 | ATAD2-003 | 0 | 0 |
| 12 | AVL9-001 | 100 | 31 |
| 22 | COL12A1-001 | 0 | 0 |
| 23 | COL6A3-001 | 0 | 0 |
| 24 | FANCI-001 | 17 | 1 |
| 28 | HSP90B1-001 | 50 | 7 |
| 15 | MUC6-001 | 83 | 22 |
| 13 | NUF2-001 | 100 | 50 |
| 19 | NUF2-002 | 50 | 6 |
| 11 | PPAP2C-001 | 83 | 29 |
| 25 | RPS11-001 | 17 | 3 |
| 29 | SIAH2-001 | 50 | 8 |
| 30 | SLC6A6-001 | 17 | 1 |
| 10 | UQCRB-001 | 83 | 24 |
| 31 | IQGAP3-001 | 100 | 24 |
| 32 | ERBB3-001 | 83 | |
| | CCDC88A-001 | 0 | 0 |
| | CCNB1-003 | 33 | 3 |
| | CCND2-001 | 17 | 10 |
| | CCNE2-001 | 0 | 0 |
| | CEA-010 | 40 | 3 |
| | CLCN3-001 | 33 | 6 |
| | DNAJC10-001 | 50 | 15 |
| | DNAJC10-002 | 33 | 3 |
| | EIF2S3-001 | 17 | 1 |
| | EIF3L-001 | 100 | 29 |
| | EPPK1-001 | 17 | 1 |
| | GPR39-001 | 50 | 6 |
| | ITGB4-001 | 67 | 20 |
| | LCN2-001 | 17 | 1 |
| | SDHC-001 | 33 | 3 |
| | PBK-001 | 0 | 0 |
| | POLD3-001 | 67 | 7 |
| | PSMD14-001 | 17 | 1 |
| | PTK2-001 | 17 | 4 |
| | TSPAN1-002 | 17 | 1 |
| | ZNF598-001 | 83 | 17 |

The following peptides were already described in other applications by immatics and included in the vaccines IMA901 (MET-001 and TOP-001), IMA910 (MET-001 and TOP-001) and IMA950 (IGF2BP3-001). As for example MET-001 leads to extremely good in vivo reactions, the data can be seen as an indication for the clinical usefulness of the peptides of the invention,

| SEQ ID NO: | Antigen | Donors positive/evaluable [%] | Wells positive/evaluable [%] |
|---|---|---|---|
| | IGF2BP3-001 | 50 | 21 |
| | MET-001 | 67 | 42 |
| | TOP-001 | 40 | 10 |

REFERENCE LIST

Ahmed, A. U., et al. "Effect of disrupting seven-in-absentia homolog 2 function on lung cancer cell growth." *J Natl. Cancer Inst.* 100.22 (2008): 1606-29.

Allison, J. P. and M. F. Krummel. "The Yin and Yang of T cell costimulation." *Science* 270.5238 (1995): 932-33.

Altmeyer, A., et al. "Tumor-specific cell surface expression of the-KDEL containing, endoplasmic reticular heat shock protein gp96." *Int J Cancer* 69.4 (1996): 340-49.

Appay, V., et al. "Decreased specific CD8+ T cell cross-reactivity of antigen recognition following vaccination with Melan-A peptide." *Eur. J Immunol.* 36.7 (2006): 1805-14.

Banerjee, S. K., et al. "Expression of cdc2 and cyclin B1 in *Helicobacter pylori*-associated gastric MALT and MALT lymphoma: relationship to cell death, proliferation, and transformation." *Am J Pathol.* 156.1 (2000): 217-25.

Bartman, A. E., et al. "Aberrant expression of MUC5AC and MUC6 gastric mucin genes in colorectal polyps." *Int J Cancer* 80.2 (1999): 210-18.

Basu, S., et al. "Necrotic but not apoptotic cell death releases heat shock proteins, which deliver a partial maturation signal to dendritic cells and activate the NF-kappa B pathway." *Int Immunol.* 12.11 (2000): 1539-46.

Bauer, B., S. Bartfeld, and T. F. Meyer. "*H. pylori* selectively blocks EGFR endocytosis via the non-receptor kinase c-Abl and CagA." *Cell Microbiol.* 11.1 (2009): 156-69.

Benatti, P., et al. "A balance between NF-Y and p53 governs the pro- and anti-apoptotic transcriptional response." *Nucleic Acids Res* 36.5 (2008): 1415-28.

Bertolini, G., et al. "Highly tumorigenic lung cancer CD133+ cells display stein-like features and are spared by cisplatin treatment." *Proc Natl. Acad. Sci. U.S.A* 106.38 (2009): 16281-86.

Bierie, B. and H. L. Moses. "TGF-beta and cancer." *Cytokine Growth Factor Rev.* 17.1-2 (2006): 29-40.

Bitoun, E. and K. E. Davies. "The robotic mouse: unravelling the function of AF4 in the cerebellum." *Cerebellum.* 4.4 (2005): 250-60.

Bolhassani, A. and S. Rafati. "Heat-shock proteins as powerful weapons in vaccine development." *Expert. Rev. Vaccines.* 7.8 (2008): 1185-99.

Borset, M., et al. "The role of hepatocyte growth factor and its receptor c-Met in multiple myeloma and other blood malignancies." *Leuk. Lymphoma* 32.3-4 (1999): 249-56.

Bradbury, P. A., et al. "Matrix metalloproteinase 1, 3 and 12 polymorphisms and esophageal adenocarcinoma risk and prognosis." *Carcinogenesis* 30.5 (2009): 793-98.

Brown, C. E., et al. "Recognition and killing of brain tumor stein-like initiating cells by CD8+ cytolytic T cells." *Cancer Research* 69.23 (2009): 8886-93.

Bruckdorfer, T., O. Marder, and F. Albericio. "From production of peptides in milligram amounts for research to multi-tons quantities for drugs of the future." *Curr. Pharm. Biotechnol.* 5.1 (2004): 29-43.

Brunsvig, P. F., et al. "Telomerase peptide vaccination: a phase I/II study in patients with non-small cell lung cancer." *Cancer Immunol. Immunother.* 55.12 (2006): 1553-64.

Cabanes, D., et al. "Gp96 is a receptor for a novel *Listeria monocytogenes* virulence factor, Vip, a surface protein." *EMBO J* 24.15 (2005): 2827-38.

Calzado, M. A., et al. "An inducible autoregulatory loop between HIPK2 and Siah2 at the apex of the hypoxic response." *Nat. Cell Biol.* 11.1 (2009): 85-91.

Castelli, C., et al. "Heat shock proteins: biological functions and clinical application as personalized vaccines for human cancer." *Cancer Immunol. Immunother.* 53.3 (2004): 227-33.

Castriconi, R., et al. "Both CD133+ and C." *Eur. J Immunol.* 37.11 (2007): 3190-96.

Chanock, S. J., et al. "HLA-A, -B, -Cw, -DQA1 and -DRB1 Alleles in a Caucasian Population from Bethesda, USA." *Hum. Immunol.* 65 (2004): 1211-23.

Chen, C. H., et al. "Inhibition of heregulin signaling by an aptamer that preferentially binds to the oligomeric form of human epidermal growth factor receptor-3." *Proc Natl. Acad. Sci. U.S.A* 100.16 (2003): 9226-31.

Chen, Z. and J. J. O'Shea. "Regulation of IL-17 production in human lymphocytes." *Cytokine* 41.2 (2008): 71-78.

Cho, S. O., et al. "*Helicobacter pylori* in a Korean Isolate Expressed Proteins Differentially in Human Gastric Epithelial Cells." *Dig. Dis. Sci.* (2009).

Christianson, J. C., et al. "OS-9 and GRP94 deliver mutant alpha1-antitrypsin to the Hrd1-SEL1L ubiquitin ligase complex for ERAD." *Nat. Cell Biol.* 10.3 (2008): 272-82.

Cisek, L. J. and J. L. Corden. "Phosphorylation of RNA polymerase by the murine homologue of the cell-cycle control protein cdc2." *Nature* 339.6227 (1989): 679-84.

Colombetti, S., et al. "Prolonged TCR/CD28 engagement drives IL-2-independent T cell clonal expansion through signaling mediated by the mammalian target of rapamycin." *J Immunol.* 176.5 (2006): 2730-38.

Confalonieri, S., et al. "Alterations of ubiquitin ligases in human cancer and their association with the natural history of the tumor." *Oncogene* 28.33 (2009): 2959-68.

Corso, S., et al. "Silencing the MET oncogene leads to regression of experimental tumors and metastases." *Oncogene* 27.5 (2008): 684-93.

Cox, C. V., et al. "Expression of CD133 on leukemia-initiating cells in childhood ALL." *Blood* 113.14 (2009): 3287-96.

Cunha-Ferreira, I., et al. "The SCF/Slimb ubiquitin ligase limits centrosome amplification through degradation of SAK/PLK4." *Curr. Biol.* 19.1 (2009): 43-49.

DeLuca, J. G., et al. "Hec1 and nuf2 are core components of the kinetochore outer plate essential for organizing microtubule attachment sites." *Mol. Biol. Cell* 16.2 (2005): 519-31.

Deng, H., et al. "Matrix metalloproteinase 11 depletion inhibits cell proliferation in gastric cancer cells." *Biochem. Biophys. Res Commun.* 326.2 (2005): 274-81.

Dengjel, J., et al. "Unexpected Abundance of HLA Class II Presented Peptides in Primary Renal Cell Carcinomas." *Clin Cancer Res.* 12.14 (2006): 4163-70.

Deremer, D. L., C. Ustun, and K. Natarajan. "Nilotinib: a second-generation tyrosine kinase inhibitor for the treatment of chronic myelogenous leukemia." *Clin Ther.* 30.11 (2008): 1956-75.

Di Renzo, M. F., et al. "Overexpression and amplification of the met/HGF receptor gene during the progression of colorectal cancer." *Clin. Cancer Res.* 1.2 (1995): 147-54.

Dong, G., et al. "Hepatocyte growth factor/scatter factor-induced activation of MEK and PI3K signal pathways contributes to expression of proangiogenic cytokines interleukin-8 and vascular endothelial growth factor in head and neck squamous cell carcinoma." *Cancer Res.* 61.15 (2001): 5911-18.

Dudley, M. E., et al. "Cancer regression and autoimmunity in patients after clonal repopulation with antitumor lymphocytes." *Science* 298.5594 (2002): 850-54.

Dudley, M. E., et al. "Adoptive cell transfer therapy following non-myeloablative but lymphodepleting chemotherapy for the treatment of patients with refractory metastatic melanoma." *J. Clin. Oncol.* 23.10 (2005): 2346-57.

Duong, C., et al. "Pretreatment gene expression profiles can be used to predict response to neoadjuvant chemoradiotherapy in esophageal cancer." *Ann Surg Oncol* 14.12 (2007): 3602-09.

Egland, K. A., et al. "High expression of a cytokeratin-associated protein in many cancers." *Proc Natl. Acad. Sci. U.S.A* 103.15 (2006): 5929-34.

Eramo, A., et al. "Identification and expansion of the tumorigenic lung cancer stem cell population." *Cell Death Differ* 15.3 (2008): 504-14.

Esashi, F., et al. "CDK-dependent phosphorylation of BRCA2 as a regulatory mechanism for recombinational repair." *Nature* 434.7033 (2005): 598-604.

Escobar, M. A., et al. "Profiling of nuclear extract proteins from human neuroblastoma cell lines: the search for fingerprints." *J Pediatr. Surg* 40.2 (2005): 349-58.

Ferracini, R., et al. "The Met/HGF receptor is over-expressed in human osteosarcomas and is activated by either a paracrine or an autocrine circuit." *Oncogene* 10.4 (1995): 739-49.

Fischer, J., et al. "Duplication and overexpression of the mutant allele of the MET proto-oncogene in multiple hereditary papillary renal cell tumours." *Oncogene* 17.6 (1998): 733-39.

Flanagan, J. M., et al. "Genomics screen in transformed stem cells reveals RNASEH2A, PPAP2C, and ADARB1 as putative anticancer drug targets." *Mol. Cancer Ther.* 8.1 (2009): 249-60.

Fong, L., et al. "Altered peptide ligand vaccination with Flt3 ligand expanded dendritic cells for tumor immunotherapy." *Proc. Natl. Acad. Sci. U.S.A* 98.15 (2001): 8809-14.

Frasor, J., et al. "Estrogen down-regulation of the corepressor N-CoR: mechanism and implications for estrogen derepression of N-CoR-regulated genes." *Proc Natl. Acad. Sci. U.S.A* 102.37 (2005): 13153-57.

Frew, I. J., et al. "Generation and analysis of Siah2 mutant mice." *Mol. Cell Biol.* 23.24 (2003): 9150-61.

Fu, Y. and A. S. Lee. "Glucose regulated proteins in cancer progression, drug resistance and immunotherapy." *Cancer Biol. Ther.* 5.7 (2006): 741-44.

Furge, K. A., et al. "Suppression of Ras-mediated tumorigenicity and metastasis through inhibition of the Met receptor tyrosine kinase." *Proc. Natl. Acad. Sci. U.S.A* 98.19 (2001): 10722-27.

Furge, K. A., Y. W. Zhang, and G. F. Vande Woude. "Met receptor tyrosine kinase: enhanced signaling through adapter proteins." *Oncogene* 19.49 (2000): 5582-89.

Gattinoni, L., et al. "Adoptive immunotherapy for cancer: building on success." *Nat. Rev. Immunol.* 6.5 (2006): 383-93.

Gherardi, E. and M. Stoker. "Hepatocyte growth factor—scatter factor: mitogen, motogen, and met." *Cancer Cells* 3.6 (1991): 227-32.

Glen, A., et al. "iTRAQ-facilitated proteomic analysis of human prostate cancer cells identifies proteins associated with progression." *J Proteome. Res* 7.3 (2008): 897-907.

Gnjatic, S., et al. "NY-CO-58/KIF2C is overexpressed in a variety of solid tumors and induces frequent T cell responses in patients with colorectal cancer." *Int J Cancer* (2009).

Guo, W. C., et al. "Expression and its clinical significance of heat shock protein gp96 in human osteosarcoma." *Neoplasma* 57.1 (2010): 62-67.

Habelhah, H., et al. "Stress-induced decrease in TRAF2 stability is mediated by Siah2." *EMBO J* 21.21 (2002): 5756-65.

Hamamoto, A., et al. "Aberrant expression of the gastric mucin MUC6 in human pulmonary adenocarcinoma xenografts." *Int J Oncol* 26.4 (2005): 891-96.

Harada, T., et al. "Genome-wide analysis of pancreatic cancer using microarray-based techniques." *Pancreatology.* 9.1-2 (2009): 13-24.

Harper, L. J., et al. "Stem cell patterns in cell lines derived from head and neck squamous cell carcinoma." *J Oral Pathol. Med* 36.10 (2007): 594-603.

Hayama, S., et al. "Activation of CDCA1-KNTC2, members of centromere protein complex, involved in pulmonary carcinogenesis." *Cancer Research* 66.21 (2006): 10339-48.

Hayashi, M., et al. "High expression of HER3 is associated with a decreased survival in gastric cancer." *Clinical Cancer Research* 14.23 (2008): 7843-49.

Heike, M., et al. "Expression of stress protein gp96, a tumor rejection antigen, in human colorectal cancer." *Int J Cancer* 86.4 (2000): 489-93.

Hodorova, I., et al. "Gp96 and its different expression in breast carcinomas." *Neoplasma* 55.1 (2008): 31-35.

Horton, R. A., et al. "A substrate for deubiquitinating enzymes based on time-resolved fluorescence resonance energy transfer between terbium and yellow fluorescent protein." *Anal. Biochem.* 360.1 (2007): 138-43.

House, C. M., A. Moller, and D. D. Bowtell. "Siah proteins: novel drug targets in the Ras and hypoxia pathways." *Cancer Research* 69.23 (2009): 8835-38.

Howard, E. W., et al. "Decreased adhesiveness, resistance to anoikis and suppression of GRP94 are integral to the survival of circulating tumor cells in prostate cancer." *Clin Exp. Metastasis* 25.5 (2008): 497-508.

Hu, G. and E. R. Fearon. "Siah-1 N-terminal RING domain is required for proteolysis function, and C-terminal sequences regulate oligomerization and binding to target proteins." *Mol. Cell Biol.* 19.1 (1999): 724-32.

Huang, Y., et al. "Characterization of GPR56 protein and its suppressed expression in human pancreatic cancer cells." *Mol. Cell Biochem.* 308.1-2 (2008): 133-39.

Jansen, M. P., et al. "Downregulation of SIAH2, an ubiquitin E3 ligase, is associated with resistance to endocrine therapy in breast cancer." *Breast Cancer Res Treat.* 116.2 (2009): 263-71.

Jia, H. L., et al. "Gene expression profiling reveals potential biomarkers of human hepatocellular carcinoma." *Clinical Cancer Research* 13.4 (2007): 1133-39.

Jucker, M., et al. "The Met/hepatocyte growth factor receptor (HGFR) gene is overexpressed in some cases of human leukemia and lymphoma." *Leuk. Res.* 18.1 (1994): 7-16.

Jung, G., J. A. Ledbetter, and H. J. Muller-Eberhard. "Induction of cytotoxicity in resting human T lymphocytes bound to tumor cells by antibody heteroconjugates." *Proc Natl Acad Sci USA* 84.13 (1987): 4611-15.

Jung, H. M., S. J. Choi, and J. K. Kim. "Expression profiles of SV40-immortalization-associated genes upregulated in various human cancers." *J Cell Biochem.* 106.4 (2009): 703-13.

Kaneko, N., et al. "siRNA-mediated knockdown against CDCA1 and KNTC2, both frequently overexpressed in colorectal and gastric cancers, suppresses cell proliferation and induces apoptosis." *Biochem. Biophys. Res Commun.* 390.4 (2009): 1235-40.

Kang, H. M., et al. "Effects of *Helicobacter pylori* Infection on gastric mucin expression." *J Clin Gastroenterol.* 42.1 (2008): 29-35.

Ko, M. A., et al. "Plk4 haploinsufficiency causes mitotic infidelity and carcinogenesis." *Nat. Genet.* 37.8 (2005): 883-88.

Kobayashi, M., et al. "Activation of ErbB3-PI3-kinase pathway is correlated with malignant phenotypes of adenocarcinomas." *Oncogene* 22.9 (2003): 1294-301.

Koochekpour, S., et al. "Met and hepatocyte growth factor/scatter factor expression in human gliomas." *Cancer Res.* 57.23 (1997): 5391-98.

Korzeniewski, N., et al. "Cullin 1 functions as a centrosomal suppressor of centriole multiplication by regulating polo-like kinase 4 protein levels." *Cancer Research* 69.16 (2009): 6668-75.

Krieg, A. M. "Therapeutic potential of Toll-like receptor 9 activation." *Nat. Rev. Drug Discov.* 5.6 (2006): 471-84.

Kunimoto, K., et al. "Involvement of IQGAP3, a regulator of Ras/ERK-related cascade, in hepatocyte proliferation in mouse liver regeneration and development." *J Cell Physiol* 220.3 (2009): 621-31.

Kuriyama, R., et al. "Gamma-tubulin-containing abnormal centrioles are induced by insufficient Plk4 in human HCT116 colorectal cancer cells." *Cell Sci.* 122. Pt 12 (2009): 2014-23.

Lee, H. S., et al. "MUC1, MUC2, MUC5AC, and MUC6 expressions in gastric carcinomas: their roles as prognostic indicators." *Cancer* 92.6 (2001): 1427-34.

Leivo, I., et al. "Characterization of gene expression in major types of salivary gland carcinomas with epithelial differentiation." *Cancer Genet. Cytogenet.* 156.2 (2005): 104-13.

Lemmel, C., et al. "Differential quantitative analysis of MHC ligands by mass spectrometry using stable isotope labeling." *Nat. Biotechnol.* 22.4 (2004): 450-54.

Li, G., et al. "Downregulation of E-cadherin and Desmoglein 1 by autocrine hepatocyte growth factor during melanoma development." *Oncogene* 20.56 (2001): 8125-35.

Lim, S. O., et al. "Expression of heat shock proteins (HSP27, HSP60, HSP70, HSP90, GRP78, GRP94) in hepatitis B virus-related hepatocellular carcinomas and dysplastic nodules." *World J Gastroenterol.* 11.14 (2005): 2072-79.

Lin, W., et al. "Tyrosine kinases and gastric cancer." *Oncogene* 19.49 (2000): 5680-89.

Liu, B. and Z. LI. "Endoplasmic reticulum HSP90b1 (gp96, grp94) optimizes B-cell function via chaperoning integrin and TLR but not immunoglobulin." *Blood* 112.4 (2008): 1223-30.

Liu, S. Y., et al. "Requirement of MMP-3 in anchorage-independent growth of oral squamous cell carcinomas." *J Oral Pathol. Med* 36.7 (2007): 430-35.

Lochter, A., et al. "The significance of matrix metalloproteinases during early stages of tumor progression." *Ann N.Y. Acad. Sci.* 857 (1998): 180-93.

Lund, C. V., et al. "Zinc finger transcription factors designed for bispecific coregulation of ErbB2 and ErbB3 receptors: insights into ErbB receptor biology." *Mol. Cell Biol.* 25.20 (2005): 9082-91.

Ma, S., et al. "Identification and characterization of tumorigenic liver cancer stem/progenitor cells." *Gastroenterology* 132.7 (2007): 2542-56.

MacLeod, R. J., M. Hayes, and I. Pacheco. "Wnt5a secretion stimulated by the extracellular calcium-sensing receptor inhibits defective Wnt signaling in colon cancer cells." *Am J Physiol Gastrointest. Liver Physiol* 293.1 (2007): G403-G411.

Macmillan, J. C., et al. "Comparative expression of the mitotic regulators SAK and PLK in colorectal cancer." *Ann Surg Oncol* 8.9 (2001): 729-40.

Maney, T., et al. "The kinetochore of higher eucaryotes: a molecular view." *Int Rev. Cytol.* 194 (2000): 67-131.

Martin, C. M., et al. "Gene expression profiling in cervical cancer: identification of novel markers for disease diagnosis and therapy." *Methods Mol. Biol.* 511 (2009): 333-59.

Matsukita, S., et al. "Expression of mucins (MUC1, MUC2, MUC5AC and MUC6) in mucinous carcinoma of the breast: comparison with invasive ductal carcinoma." *Histopathology* 42.1 (2003): 26-36.

Maulik, G., et al. "Role of the hepatocyte growth factor receptor, c-Met, in oncogenesis and potential for therapeutic inhibition." *Cytokine Growth Factor Rev.* 13.1 (2002): 41-59.

Mizrak, D., M. Brittan, and M. Alison. "CD133: molecule of the moment." *J Pathol.* 214.1 (2008): 3-9.

Montesano, R., et al. "Differential effects of hepatocyte growth factor isoforms on epithelial and endothelial tubulogenesis." *Cell Growth Differ.* 9.5 (1998): 355-65.

Monzani, E., et al. "Melanoma contains CD133 and ABCG2 positive cells with enhanced tumourigenic potential." *Eur. J Cancer* 43.5 (2007): 935-46.

Moore, A. and L. Wordeman. "The mechanism, function and regulation of depolymerizing kinesins during mitosis." *Trends Cell Biol.* 14.10 (2004): 537-46.

Morgan, R. A., et al. "Cancer Regression in Patients After Transfer of Genetically Engineered Lymphocytes." *Science* (2006).

Mori, M., et al. "HLA gene and haplotype frequencies in the North American population: the National Marrow Donor Program Donor Registry." *Transplantation* 64.7 (1997): 1017-27.

Murray, G. I., et al. "Matrix metalloproteinases and their inhibitors in gastric cancer." *Gut* 43.6 (1998): 791-97.

Murshid, A., J. Gong, and S. K. Calderwood. "Heat-shock proteins in cancer vaccines: agents of antigen cross-presentation." *Expert. Rev. Vaccines.* 7.7 (2008): 1019-30.

Nakaigawa, N., et al. "Inactivation of von Hippel-Lindau gene induces constitutive phosphorylation of MET protein in clear cell renal carcinoma." *Cancer Res.* 66.7 (2006): 3699-705.

Nakamura, Y., et al. "Clinicopathological and biological significance of mitotic centromere-associated kinesin overexpression in human gastric cancer." *Br. J Cancer* 97.4 (2007): 543-49.

Nakayama, K., J. Qi, and Z. Ronai. "The ubiquitin ligase Siah2 and the hypoxia response." *Mol. Cancer Res* 7.4 (2009): 443-51.

Naldini, L., et al. "Hepatocyte growth factor (HGF) stimulates the tyrosine kinase activity of the receptor encoded by the proto-oncogene c-MET." *Oncogene* 6.4 (1991): 501-04.

Nguyen, Q. N., et al. "Light controllable siRNAs regulate gene suppression and phenotypes in cells." *Biochim. Biophys. Acta* 1758.3 (2006): 394-403.

Nishio, K., et al. "Crystal structure of the de-ubiquitinating enzyme UCH37 (human UCH-L5) catalytic domain." *Biochem. Biophys. Res Commun.* 390.3 (2009): 855-60.

Nojima, H., et al. "IQGAP3 regulates cell proliferation through the Ras/ERK signalling cascade." *Nat. Cell Biol.* 10.8 (2008): 971-78.

Nomura, H., et al. "Enhanced production of matrix metalloproteinases and activation of matrix metalloproteinase 2 (gelatinase A) in human gastric carcinomas." *Int J Cancer* 69.1 (1996): 9-16.

Nomura, H., et al. "Network-based analysis of calcium-binding protein genes identifies Grp94 as a target in human oral carcinogenesis." *Br. J Cancer* 97.6 (2007): 792-801.

Ohnuma, S., et al. "Cancer-associated splicing variants of the CDCA1 and MSMB genes expressed in cancer cell lines and surgically resected gastric cancer tissues." *Surgery* 145.1 (2009): 57-68.

Park, Y. H., et al. "Capecitabine in combination with Oxaliplatin (XELOX) as a first-line therapy for advanced gastric cancer." *Cancer Chemother. Pharmacol.* (2007).

Pascolo, S., et al. "The non-classical HLA class I molecule HFE does not influence the NK-like activity contained in fresh human PBMCs and does not interact with NK cells." *Int. Immunol.* 17.2 (2005): 117-22.

Peel, N., et al. "Overexpressing centriole-replication proteins in vivo induces centriole overduplication and de novo formation." *Curr. Biol.* 17.10 (2007): 834-43.

Pereira, M. B., et al. "Immunohistochemical study of the expression of MUC5AC and MUC6 in breast carcinomas and adjacent breast tissues." *J Clin Pathol.* 54.3 (2001): 210-13.

Pietra, G., et al. "Natural killer cells kill human melanoma cells with characteristics of cancer stem cells." *Int Immunol.* 21.7 (2009): 793-801.

Poller, D. N., et al. "Production and characterization of a polyclonal antibody to the c-erbB-3 protein: examination of c-erbB-3 protein expression in adenocarcinomas." *J Pathol.* 168.3 (1992): 275-80.

Pons, E., C. C. Uphoff, and H. G. Drexler. "Expression of hepatocyte growth factor and its receptor c-met in human leukemia-lymphoma cell lines." *Leuk. Res.* 22.9 (1998): 797-804.

Ponzetto, C., et al. "A novel recognition motif for phosphatidylinositol 3-kinase binding mediates its association with the hepatocyte growth factor/scatter factor receptor." *Mol. Cell Biol.* 13.8 (1993): 4600-08.

Poppe, M., et al. "Phosphorylation of *Helicobacter pylori* CagA by c-Abl leads to cell motility." *Oncogene* 26.24 (2007): 3462-72.

Pytel, D., et al. "Tyrosine kinase blockers: new hope for successful cancer therapy." *Anticancer Agents Med Chem.* 9.1 (2009): 66-76.

Qi, J., et al. "The ubiquitin ligase Siah2 regulates tumorigenesis and metastasis by HIF-dependent and -independent pathways." *Proc Natl. Acad. Sci. U.S.A* 105.43 (2008): 16713-18.

Qian, C. N., et al. "Met protein expression level correlates with survival in patients with late-stage nasopharyngeal carcinoma." *Cancer Res.* 62.2 (2002): 589-96.

Qian, Z., et al. "Cytogenetic and genetic pathways in therapy-related acute myeloid leukemia." *Chem. Biol. Interact.* (2009).

Ramirez, R., et al. "Over-expression of hepatocyte growth factor/scatter factor (HGF/SF) and the HGF/SF receptor (cMET) are associated with a high risk of metastasis and recurrence for children and young adults with papillary thyroid carcinoma." *Clin Endocrinol.(Oxf)* 53.5 (2000): 635-44.

Rammensee, H. G., et al. "SYFPEITHI: database for MHC ligands and peptide motifs." *Immunogenetics* 50.3-4 (1999): 213-19.

Rammensee, H. G., J. Bachmann, and S. Stevanovic. *MHC Ligands and Peptide Motifs*. Springer-Verlag, Heidelberg, Germany, 1997.

Rappa, G., O. Fodstad, and A. Lorico. "The stem cell-associated antigen CD133 (Prominin-1) is a molecular therapeutic target for metastatic melanoma." *Stem Cells* 26.12 (2008): 3008-17.

Richardson, G. D., et al. "CD133, a novel marker for human prostatic epithelial stein cells." *J Cell Sci.* 117. Pt 16 (2004): 3539-45.

Rini, B. I., et al. "Combination immunotherapy with prostatic acid phosphatase pulsed antigen-presenting cells (provenge) plus bevacizumab in patients with serologic progression of prostate cancer after definitive local therapy." *Cancer* 107.1 (2006): 67-74.

Rodrigues-Martins, A., et al. "Revisiting the role of the mother centriole in centriole biogenesis." *Science* 316.5827 (2007): 1046-50.

Rosenberg, S. A., et al. "A progress report on the treatment of 157 patients with advanced cancer using lymphokine-activated killer cells and interleukin-2 or high-dose interleukin-2 alone." *N. Engl. J. Med.* 316.15 (1987): 889-97.

Rosenberg, S. A., et al. "Use of tumor-infiltrating lymphocytes and interleukin-2 in the immunotherapy of patients with metastatic melanoma. A preliminary report." *N. Engl. J Med* 319.25 (1988): 1676-80.

Rott, R., et al. "Monoubiquitylation of alpha-synuclein by seven in absentia homolog (SIAH) promotes its aggregation in dopaminergic cells." *J Biol. Chem.* 283.6 (2008): 3316-28.

Rutella, S., et al. "Cells with characteristics of cancer stem/progenitor cells express the CD133 antigen in human endometrial tumors." *Clinical Cancer Research* 15.13 (2009): 4299-311.

Saiki, R. K., et al. "Primer-directed enzymatic amplification of DNA with a thermostable DNA polymerase." *Science* 239.4839 (1988): 487-91.

Samant, G. V. and P. W. Sylvester. "gamma-Tocotrienol inhibits ErbB3-dependent PI3K/Akt mitogenic signalling in neoplastic mammary epithelial cells." *Cell Prolif.* 39.6 (2006): 563-74.

Sanidas, E. E., et al. "Expression of the c-erbB-3 gene product in gastric cancer." *Int J Cancer* 54.6 (1993): 935-40.

Scott, G. K., et al. "Coordinate suppression of ERBB2 and ERBB3 by enforced expression of micro-RNA miR-125a or miR-125b." *J Biol. Chem.* 282.2 (2007): 1479-86.

Sergina, N. V., et al. "Escape from HER-family tyrosine kinase inhibitor therapy by the kinase-inactive HER3." *Nature* 445.7126 (2007): 437-41.

Shah, M., et al. "Inhibition of Siah2 ubiquitin ligase by vitamin K3 (menadione) attenuates hypoxia and MAPK signaling and blocks melanoma tumorigenesis." *Pigment Cell Melanoma Res* 22.6 (2009): 799-808.

Shapiro, G. I. "Cyclin-dependent kinase pathways as targets for cancer treatment." *J Clin Oncol* 24.11 (2006): 1770-83.

Sherman-Baust, C. A., et al. "Remodeling of the extracellular matrix through overexpression of collagen VI contributes to cisplatin resistance in ovarian cancer cells." *Cancer Cell* 3.4 (2003): 377-86.

Sheu, M. L., S. H. Liu, and K. H. Lan. "Honokiol induces calpain-mediated glucose-regulated protein-94 cleavage and apoptosis in human gastric cancer cells and reduces tumor growth." *PLoS. ONE.* 2.10 (2007): e1096.

Shimo, A., et al. "Involvement of kinesin family member 2C/mitotic centromere-associated kinesin overexpression in mammary carcinogenesis." *Cancer Sci.* 99.1 (2008): 62-70.

Singh, S. K., et al. "Identification of a cancer stem cell in human brain tumors." *Cancer Res.* 63.18 (2003): 5821-28.

Singh, S. K., et al. "Identification of human brain tumour initiating cells." *Nature* 432.7015 (2004): 396-401.

Sithanandam, G. and L. M. Anderson. "The ERBB3 receptor in cancer and cancer gene therapy." Cancer *Gene Ther.* 15.7 (2008): 413-48.

Sithanandam, G., et al. "Inactivation of ErbB3 by siRNA promotes apoptosis and attenuates growth and invasiveness of human lung adenocarcinoma cell line A549." *Oncogene* 24.11 (2005): 1847-59.

Skawran, B., et al. "Gene expression profiling in hepatocellular carcinoma: upregulation of genes in amplified chromosome regions." *Mod. Pathol.* 21.5 (2008): 505-16.

Slesak, B., et al. "Expression of epidermal growth factor receptor family proteins (EGFR, c-erbB-2 and c-erbB-3) in gastric cancer and chronic gastritis." *Anticancer Res* 18.4A (1998): 2727-32.

Small, E. J., et al. "Placebo-controlled phase III trial of immunologic therapy with sipuleucel-T (APC8015) in patients with metastatic, asymptomatic hormone refractory prostate cancer." *J Clin Oncol.* 24.19 (2006): 3089-94.

Smith, L. M., et al. "CD133/prominin-1 is a potential therapeutic target for antibody-drug conjugates in hepatocellular and gastric cancers." *Br. J Cancer* 99.1 (2008): 100-09.

Smith, M. J., et al. "Analysis of differential gene expression in colorectal cancer and stroma using fluorescence-activated cell sorting purification." *Br. J Cancer* 100.9 (2009): 1452-64.

Smogorzewska, A., et al. "Identification of the FANCI protein, a monoubiquitinated FANCD2 paralog required for DNA repair." *Cell* 129.2 (2007): 289-301.

Staehler, M., Stenzl, A., Dietrich, P. Y., Eisen, T., Haferkamp, A., Beck, J., Mayer, A., Walter, S., Singh-Jasuja, H., and Stief, C. A phase I study to evaluate safety, immunogenicity and anti-tumor activity of the multipeptide vaccine IMA901 in renal cell carcinoma patients (RCC). Journal of Clinical Oncology, 2007 ASCO Annual Meeting Proceedings Part I Vol 25, No. 18S (June 20 Supplement), 2007: 5098. 6-20-2007. Ref Type: Abstract Steinmann, O., et al. "Dual inhibition of sister chromatid separation at metaphase." *Cell* 107.6 (2001): 715-26.

Suetsugu, A., et al. "Characterization of CD133+ hepatocellular carcinoma cells as cancer stem/progenitor cells." *Biochem. Biophys. Res. Commun.* 351.4 (2006): 820-24.

Suva, M. L., et al. "Identification of Cancer Stein Cells in Ewing's Sarcoma." *Cancer Research* (2009).

Swallow, C. J., et al. "Sak/Plk4 and mitotic fidelity." *Oncogene* 24.2 (2005): 306-12.

Szczepanowski, M., et al. "Regulation of repp86 stability by human Siah2." *Biochem. Biophys. Res Commun.* 362.2 (2007): 485-90.

Tajima, Y., et al. "Gastric and intestinal phenotypic marker expression in early differentiated-type tumors of the stomach: clinicopathologic significance and genetic background." *Clinical Cancer Research* 12.21 (2006): 6469-79.

Takaishi, S., et al. "Identification of gastric cancer stem cells using the cell surface marker CD44." *Stein Cells* 27.5 (2009): 1006-20.

Takayama, H., et al. "Diverse tumorigenesis associated with aberrant development in mice overexpressing hepatocyte growth factor/scatter factor." *Proc. Natl. Acad. Sci. U.S.A* 94.2 (1997): 701-06.

Teofili, L., et al. "Expression of the c-met proto-oncogene and its ligand, hepatocyte growth factor, in Hodgkin disease." *Blood* 97.4 (2001): 1063-69.

Thorsen, K., et al. "Alternative splicing in colon, bladder, and prostate cancer identified by exon array analysis." *Mol. Cell Proteomics.* 7.7 (2008): 1214-24.

Tirino, V., et al. "The role of CD133 in the identification and characterisation of tumour-initiating cells in non-small-cell lung cancer." *Eur. J Cardiothorac. Surg* 36.3 (2009): 446-53.

Todaro, M., et al. "Colon cancer stem cells dictate tumor growth and resist cell death by production of interleukin-4." *Cell Stein Cell* 1.4 (2007): 389-402.

Topol, L., et al. "Wnt-5a inhibits the canonical Wnt pathway by promoting GSK-3-independent beta-catenin degradation." *J Cell Biol.* 162.5 (2003): 899-908.

Toribara, N. W., et al. "Human gastric mucin. Identification of a unique species by expression cloning." *J Biol. Chem.* 268.8 (1993): 5879-85.

Tsan, M. F. and B. Gao. "Heat shock protein and innate immunity." *Cell Mol. Immunol.* 1.4 (2004): 274-79.

Tuck, A. B., et al. "Coexpression of hepatocyte growth factor and receptor (Met) in human breast carcinoma." *Am. J. Pathol.* 148.1 (1996): 225-32.

Vairaktaris, E., et al. "Association of −1171 promoter polymorphism of matrix metalloproteinase-3 with increased risk for oral cancer." *Anticancer Res* 27.6B (2007): 4095-100.

Vandenbroeck, K., E. Martens, and I. Alloza. "Multi-chaperone complexes regulate the folding of interferon-gamma in the endoplasmic reticulum." *Cytokine* 33.5 (2006): 264-73.

Walter, S., et al. "Cutting edge: predetermined avidity of human CD8 T cells expanded on calibrated MHC/anti-CD28-coated microspheres." *J. Immunol.* 171.10 (2003): 4974-78.

Wang, Q., et al. "Overexpression of endoplasmic reticulum molecular chaperone GRP94 and GRP78 in human lung cancer tissues and its significance." *Cancer Detect. Prev.* 29.6 (2005): 544-51.

Wang, R., et al. "Activation of the Met receptor by cell attachment induces and sustains hepatocellular carcinomas in transgenic mice." *J. Cell Biol.* 153.5 (2001): 1023-34.

Wang, R. Q. and D. C. Fang. "Effects of *Helicobacter pylori* infection on mucin expression in gastric carcinoma and pericancerous tissues." *J Gastroenterol. Hepatol.* 21.2 (2006): 425-31.

Wang, S., et al. "IQGAP3, a novel effector of Rac1 and Cdc42, regulates neurite outgrowth." *J Cell Sci.* 120. Pt 4 (2007): 567-77.

Wang, X., et al. "Immunolocalisation of heat shock protein 72 and glycoprotein 96 in colonic adenocarcinoma." *Acta Histochem.* 110.2 (2008): 117-23.

Wang, X. P., et al. "Expression and significance of heat shock protein 70 and glucose-regulated protein 94 in human esophageal carcinoma." *World J Gastroenterol.* 11.3 (2005): 429-32.

Wang, X. P., et al. "Correlation between clinicopathology and expression of heat shock protein 70 and glucose-regulated protein 94 in human colonic adenocarcinoma." *World J Gastroenterol.* 11.7 (2005): 1056-59.

Wang, X. P., Q. X. Wang, and X. P. Ying. "Correlation between clinicopathology and expression of heat shock protein 72 and glycoprotein 96 in human gastric adenocarcinoma." *Tohoku J Exp. Med* 212.1 (2007): 35-41.

Weinschenk, T., et al. "Integrated functional genomics approach for the design of patient-individual antitumor vaccines." *Cancer Res.* 62.20 (2002): 5818-27.

White, C. D., M. D. Brown, and D. B. Sacks. "IQGAPs in cancer: a family of scaffold proteins underlying tumorigenesis." *FEBS Lett.* 583.12 (2009): 1817-24.

Wicks, S. J., et al. "Reversible ubiquitination regulates the Smad/TGF-beta signalling pathway." *Biochem. Soc Trans.* 34. Pt 5 (2006): 761-63.

Wicks, S. J., et al. "The deubiquitinating enzyme UCH37 interacts with Smads and regulates TGF-beta signalling." *Oncogene* 24.54 (2005): 8080-84.

Yajima, S., et al. "Expression profiling of fecal colonocytes for RNA-based screening of colorectal cancer." *Int J Oncol* 31.5 (2007): 1029-37.

Yang, L., et al. "IL-21 and TGF-beta are required for differentiation of human T(H)17 cells." *Nature* (2008).

Yang, S., et al. "Molecular basis of the differences between normal and tumor tissues of gastric cancer." *Biochim. Biophys. Acta* 1772.9 (2007): 1033-40.

Yao, D. F., et al. "Abnormal expression of HSP gp96 associated with HBV replication in human hepatocellular carcinoma." *Hepatobiliary. Pancreat. Dis. Int* 5.3 (2006): 381-86.

Yasui, W., et al. "Increased expression of p34cdc2 and its kinase activity in human gastric and colonic carcinomas." *Int J Cancer* 53.1 (1993): 36-41.

Yee, C., et al. "Adoptive T cell therapy using antigen-specific CD8+ T cell clones for the treatment of patients with metastatic melanoma: in vivo persistence, migration, and antitumor effect of transferred T cells." *Proc. Natl. Acad. Sci. U.S.A* 99.25 (2002): 16168-73.

Yin, S., et al. "CD133 positive hepatocellular carcinoma cells possess high capacity for tumorigenicity." *Int. J Cancer* 120.7 (2007): 1444-50.

Yokozaki, H., W. Yasui, and E. Tahara. "Genetic and epigenetic changes in stomach cancer." *Int Rev. Cytol.* 204 (2001): 49-95.

Yuan, W., et al. "Expression of EphA2 and E-cadherin in gastric cancer: correlated with tumor progression and lymphogenous metastasis." *Pathol. Oncol Res* 15.3 (2009): 473-78.

Yuan, W. J., et al. "Over-expression of EphA2 and EphrinA-1 in human gastric adenocarcinoma and its prognostic value for postoperative patients." *Dig. Dis. Sci.* 54.11 (2009): 2410-17.

Zaremba, S., et al. "Identification of an enhancer agonist cytotoxic T lymphocyte peptide from human carcinoembryonic antigen." *Cancer Res.* 57.20 (1997): 4570-77.

Zhang, X., R. M. Kedl, and J. Xiang. "CD40 ligation converts TGF-beta-secreting tolerogenic CD4-8-dendritic cells into IL-12-secreting immunogenic ones." *Biochem. Biophys. Res Commun.* 379.4 (2009): 954-58.

Zhang, X. L., et al. "Comparative study on overexpression of HER2/neu and HER3 in gastric cancer." *World J Surg* 33.10 (2009): 2112-18.

Zhao, C., et al. "Hedgehog signalling is essential for maintenance of cancer stem cells in myeloid leukaemia." *Nature* (2009).

Zheng, H., et al. "Cell surface targeting of heat shock protein gp96 induces dendritic cell maturation and antitumor immunity." *J Immunol.* 167.12 (2001): 6731-35.

Zheng, H., et al. "MUC6 down-regulation correlates with gastric carcinoma progression and a poor prognosis: an immunohistochemical study with tissue microarrays." *Cancer Res Clin Oncol* 132.12 (2006): 817-23.

Zheng, H. C., et al. "Overexpression of GRP78 and GRP94 are markers for aggressive behavior and poor prognosis in gastric carcinomas." *Hum. Pathol.* 39.7 (2008): 1042-49.

Zhou, G., et al. "2D differential in-gel electrophoresis for the identification of esophageal scans cell cancer-specific protein markers." *Mol. Cell Proteomics.* 1.2 (2002): 117-24.

Zhou, L., et al. "TGF-beta-induced Foxp3 inhibits T(H)17 cell differentiation by antagonizing RORgammat function." *Nature* 453.7192 (2008): 236-40.

Zhu, K. J., et al. "Imiquimod inhibits the differentiation but enhances the maturation of human monocyte-derived dendritic cells." *Int Immunopharmacol.* 9.4 (2009): 412-17.

The invention claimed is:

1. A method of treating a patient who has gastric cancer, gastrointestinal cancer, colorectal cancer, pancreatic cancer, lung cancer, and/or renal cancer, comprising administering to said patient a composition comprising a population of activated T cells that selectively recognize cells in the patient that aberrantly express a peptide, wherein said peptide consists of the amino acid sequence of LYQILQGIVF (SEQ ID NO: 1), wherein the peptide is in a complex with an MHC molecule.

2. The method of claim 1, wherein the T cells are autologous to the patient.

3. The method of claim 1, wherein the T cells are obtained from a healthy donor.

4. The method of claim 1, wherein the T cells are derived from tumor infiltrating lymphocytes or peripheral blood mononuclear cells.

5. The method of claim 1, further comprising expanding T cells in vitro.

6. The method of claim 1, wherein the MHC molecule is a class I molecule.

7. The method of claim 1, wherein the composition further comprises an adjuvant.

8. The method of claim 7, wherein the adjuvant is selected from the group consisting of anti-CD40 antibody, imiquimod, resiquimod, GM-CSF, cyclophosphamide, Sunitinib, bevacizumab, interferon-alpha, interferon-beta, CpG oligonucleotides and derivatives, poly-(I:C) and derivatives, RNA, sildenafil, and particulate formations with poly(lactide co-glycolide) (PLG), virosomes, interleukin (IL)-1, IL-2, IL-4, IL-7, IL-12, IL-13, IL-15, IL-21, and IL-23.

9. The method of claim 1, wherein the activated T cells are cytotoxic T cells produced by contacting T cells, in vitro, with an antigen presenting cell that expresses the peptide in a complex with an MHC class I molecule on the surface of the antigen presenting cell, for a period of time sufficient to activate said T cell specifically against the peptide.

10. The method of claim 9, further comprising stimulating the activated T cells in the presence of an anti-CD28 antibody and IL-12 to clonally expand the T cells.

11. The method of claim 1, wherein the patient has gastric cancer.

12. The method of claim 1, wherein the patient has gastrointestinal cancer.

13. The method of claim 1, wherein the patient has colorectal cancer.

14. The method of claim 1, wherein the patient has pancreatic cancer.

15. The method of claim 1, wherein the MEW molecule is HLA-A*024.

* * * * *